(12) United States Patent
Carlson et al.

(10) Patent No.: US 10,822,318 B2
(45) Date of Patent: Nov. 3, 2020

(54) LACTONE-BASED PROBES AND METHODS OF USE THEREOF

(71) Applicants: REGENTS OF THE UNIVERSITY OF MINNESOTA, Minneapolis, MN (US); Indiana University Research and Technology Corporation, Indianapolis, IN (US)

(72) Inventors: Erin Elizabeth Carlson, Minneapolis, MN (US); Shabnam Sharifzadeh, Minneapolis, MN (US); Alireza Shokri, Minneapolis, MN (US); Ozden Kocaoglu, Fremont, CA (US); Clayton L. Brown, Jr., Evansville, IN (US)

(73) Assignees: Regents of the University of Minnesota, Minneapolis, MN (US); Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 15/988,986

(22) Filed: May 24, 2018

(65) Prior Publication Data
US 2018/0339972 A1  Nov. 29, 2018

Related U.S. Application Data

(60) Provisional application No. 62/510,663, filed on May 24, 2017.

(51) Int. Cl.
| | |
|---|---|
| *C07D 305/12* | (2006.01) |
| *C07D 407/12* | (2006.01) |
| *G01N 33/68* | (2006.01) |
| *G07F 5/02* | (2006.01) |
| *C07D 405/12* | (2006.01) |
| *G01N 33/58* | (2006.01) |
| *G01N 33/573* | (2006.01) |
| *C07F 5/02* | (2006.01) |

(52) U.S. Cl.
CPC ......... *C07D 305/12* (2013.01); *C07D 405/12* (2013.01); *C07D 407/12* (2013.01); *C07F 5/022* (2013.01); *G01N 33/573* (2013.01); *G01N 33/582* (2013.01); *G01N 33/68* (2013.01); *G01N 2333/948* (2013.01); *G01N 2415/00* (2013.01)

(58) Field of Classification Search
CPC .. C07D 305/12; C07D 405/12; C07D 407/12; C07F 5/022; G01N 33/573; G01N 33/582; G01N 33/68
USPC ...................................................... 549/328
See application file for complete search history.

(56) References Cited

U.S. PATENT DOCUMENTS

| 9,521,845 B2 | 12/2016 | Sieber et al. |
| 2010/0069294 A1* | 3/2010 | Petter .................... A61K 47/64 514/1.1 |
| 2010/0311711 A1* | 12/2010 | Piomelli .............. A61K 31/165 514/210.02 |
| 2014/0193831 A1 | 7/2014 | Van Der Hoorn et al. |
| 2016/0221977 A1 | 8/2016 | Sello et al. |
| 2018/0292387 A1 | 10/2018 | Carlson et al. |

FOREIGN PATENT DOCUMENTS

| WO | WO-2015035278 A1 * | 3/2015 | .......... C07D 401/14 |
| WO | WO-2016069542 A2 * | 5/2016 | .......... A61K 31/337 |

OTHER PUBLICATIONS

Wang; Nature Chemical Biology 2008, 4, 557-563, with supplemental material. (Year: 2008).*
Pu; J. Org. Chem. 1994, 59, 3642-3655. (Year: 1994).*
Garner; Chem. Commun., 2013, 49, 1515-1517. (Year: 2013).*
Kocaoglu, Ozden, PhD Thesis Indiana University: "Activity-based probes for selective penicillin-binding protein visualization" UMI No. 3669379, Published by ProQuest LLC (2014). (Year: 2014).*
Indiana University, Calendar announcement of Ph.D. Defense of Ozden Kocaoglu on Tuesday, Dec. 9, 2014, Downloaded on Jan. 18, 2019 from: https://onestart.iu.edu/ccl-prd/EventMaintenance.do?methodToCall=viewEvent&eventId=10951377& pubCallId=GRP1342. (Year: 2014).*
Indiana University, The University Graduate School, thesis guidelines, Downloaded on Jan. 21, 2019 from: https://graduate.indiana.edu/thesis-dissertation/subnmission/doctoral.html. (Year: 2019).*
Aubry; Org. Biomol. Chem., 2011, 9, 7134-7143. (Year: 2011).*
Kluge; Current Opinion in Chemical Biology 2010, 14, 421-427. (Year: 2010).*

(Continued)

*Primary Examiner* — Daniel R Carcanague
(74) *Attorney, Agent, or Firm* — Viksnins Harris Padys Malen LLP

(57) ABSTRACT

The invention provides a compound of formula I:

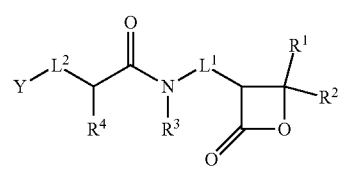

or a salt thereof, wherein $R^1$, $R^2$, $R^3$, $R^4$, $L^1$, $L^2$ and Y have any of the values described in the specification, as well as compositions comprising a compound of formula I. The compounds are useful for labeling penicillin-binding proteins (PBPs).

10 Claims, 9 Drawing Sheets

(56) References Cited

OTHER PUBLICATIONS

Lavis; Annu. Rev. Biochem. 2017, 86, 825-843. DOI: 10.1146/annurev-biochem-061516-044839 (Year: 2017).*
Sharifzadeh; ACS Chem. Biol. 2020, 15, 5, 1242-1251. DOI: 10.1021/acschembio.9b00977 (Year: 2020).*
Sharifzadeh; Current Topics in Microbiology and Immunology 2019, 420, 23-48. DOI: 10.1007/82_2018_135 (Year: 2019).*
Sharifzadeh; Methods in Enzymology 2020, 638, 27-55. DOI: 10.1016/bs.mie.2020.02.015 (Year: 2020).*
Sharifzadeh, et al., "Activity-Based Probes For Selective Penicillin-Binding Protein Visualization", International Chemical Biology Symposium, Madison, WI, Oct. 24-26, 2016.
Sharifzadeh, et al., "Novel Electrophilic Scaffold for Imaging of Essential Penicillin-Binding Proteins in Streptococcus pneumoniae", ACS Chem Biol 12(11), 2849-2857 (2017).
Sharifzadeh, et al., "Profiling of β-Lactam Selectivity for Penicillin-Binding Proteins in Bacillus subtilis and Methicillin-Sensitive and -Resistant Staphylococcus aureus", Poster, Chemical Biology Training Grant Symposium, 7 pages, May 25, 2016.
Sharifzadeh, et al., "Visualization of Penicillin-Binding Proteins in Streptococcus pneumoniae Using a Variety of Activity-Based Probes", Poster, MIKI Conference, 7 pages, Apr. 8, 2017.
Shieh, et al., "Imaging bacterial peptidoglycan with near-infrared fluorogenic azide probes", Proc Natl Acad Sci 111, 5456-5461 (2014).
Siegrist, et al., "(D)-Amino acid chemical reporters reveal peptidoglycan dynamics of an intracellular pathogen", ACS Chem Biol 8, 500-503 (2013).
Speers, et al., "Profiling enzyme activities in vivo using click chemistry methods", Chem Biol 11, 535-546 (2004).
Spratt, et al., "Penicillin-binding proteins and cell shape in E. coli", Nature 254, 516-517 (1975).
Staub, et al., "β-Lactams as Selective Chemical Probes for the in Vivo Labeling of Bacterial Enzymes Involved in Cell Wall Biosynthesis, Antibiotic Resistance, and Virulence", J Am Chem Soc 130, 13400-13409 (2008).
Swulius, et al., "The Helical MreB Cytoskeleton in Escherichia coil MC1000/pLE7 Is an Artifact of the N-Terminal Yellow Fluorescent Protein Tag", J Bacteriol 194(23), 6382-6386 (2012).
Tiyanont, et al., "Imaging peptidoglycan biosynthesis in Bacillus subtilis with fluorescent antibiotics", Proc Natl Acad Sci U S A 103, 11033-11038 (2006).
Tsien, "The green fluorescent protein", Annu Rev Biochem 67, 509-544 (1998).
Tsui, et al., "Pbp2x localizes separately from Pbp2b and other peptidoglycan synthesis proteins during later stages of cell division of Streptococcus pneumoniae D39", Mol Microbiol 94, 21-40 (2014).
Tymiak, et al., "Structure of obafluorin: an antibacterial .beta.-lactone from Pseudomonas fluorescens", J Org Chem 50(26), 5491-5495 (1985).
Venukadasula, et al., "A Concise, Phosphate-Mediated Approach to the Total Synthesis of (−)-Tetrahydrolipstatin", Org Lett 12, 1556-1559 (2010).
Vollmer, et al., "Peptidoglycan structure and architecture", FEMS Microbiol Rev 32, 149-167 (2008).
Waxman, et al., "Penicillin-binding proteins and the mechanism of action of beta-lactam antibiotics", Annu Rev Biochem 52, 825-869 (1983).
Wells, et al., "Distribution of β-Lactam and β-Lactone Producing Bacteria in Nature", J Antibiot (Tokyo) 35, 814-821 (1982).
Wells, et al., "Obafluorin, a novel beta-lactone produced by Pseudomonas fluorescens. Taxonomy, fermentation and biological properties", J Antibiot (Tokyo) 37, 802-803 (1984).
Zeiler, et al., "Vibralactone as a Tool to Study the Activity and Structure of the ClpP1P2 Complex from Listeria monocytogenes", Angew Chem Int Ed Engl 50, 11001-11004 (2011).

Zhao, et al., "Bocillin FL, a sensitive and commercially available reagent for detection of penicillin-binding proteins", Antimicrob Agents Chemother 43, 1124-1128 (1999).
Zhao, et al., "Mechanistic analysis of aliphatic β-lactones in Vibrio harveyi reveals a quorum sensing independent mode of action", Chem Commun 52, 11971-11974 (2016).
Aldridge, et al., "Antibiotic 1233A: a fungal-lactone", J Chem Soc Perkin 1, 23, 3888-3891 (1971).
Bisson-Filho, et al., "Treadmilling by FtsZ filaments drives peptidoglycan synthesis and bacterial cell division", Science 355, 739-743 (2017).
Blumberg, et al., "Isolation by Covalent Affinity Chromatography of the Penicillin-Binding Components from Membranes of Bacillus subtilis", Proc Natl Acad Sci U S A 69, 3751-3755 (1972).
Boersma, et al., "Minimal Peptidoglycan (PG) Turnover in Wild-Type and PG Hydrolase and Cell Division Mutants of Streptococcus pneumoniae D39 Growing Planktonically and in Host-Relevant Biofilms", J Bacteriol 197, 3472-3485 (2015).
Bottcher, et al., "β-Lactams and β-lactones as activity-based probes in chemical biology", Med. Chem. Commun. 3, 408-417 (2012).
Bottcher, et al., "β-Lactones as Privileged Structures for the Active-Site Labeling of Versatile Bacterial Enzyme Classes", Angew Chem Int Ed 47, 4600-4603 (2008).
Bottcher, et al., "β-Lactones as Specific Inhibitors of ClpP Attenuate the Production of Extracellular Virulence Factors of Staphylococcus aureus", J Am Chem Soc 130, 14400-14401 (2008).
Bush, et al., "Improved sensitivity in assays for binding of novel beta-lactam antibiotics to penicillin-binding proteins of Escherichia coli", Antimicrobial Agents Chemother 31(8), 1271-1273 (1987).
Carlson, "Imaging of Penicillin-Binding Protein Activity in Streptococcus pneumoniae", Presentation at American Chemical Society, 21 pages, Mar. 28, 2017.
Clatworthy, et al., "Targeting virulence: a new paradigm for antimicrobial therapy", Nat Chem Biol 3, 541-548 (2007).
Compton, et al., "Antibacterial Activity of and Resistance to Small Molecule Inhibitors of the ClpP Peptidase", ACS Chem Biol 8(12), 2669-2677 (2013).
Daniel, et al., "Control of cell morphogenesis in bacteria: two distinct ways to make a rod-shaped cell", Cell 113, 767-776 (2003).
Dargis, et al., "Use of Biotinylated r-Lactams and Chemiluminescence for Study and Purification of Penicillin-Binding Proteins in Bacteria", Antimicrob Agents Ch 8, 973-980 (1994).
Dominguez-Escobar, et al., "Processive movement of MreB-associated cell wall biosynthetic complexes in bacteria", Science 333, 225-228 (2011).
Falconer, et al., "Antibiotics as probes of biological complexity", Nat. Chem. Biol. 7, 415-423 (2011).
Fisher, et al., "Bacterial resistance to beta-lactam antibiotics: compelling opportunism, compelling opportunity", Chem. Rev. 105, 395-424 (2005).
Fleurie, et al., "Interplay of the Serine/Threonine-Kinase StkP and the Paralogs DivIVA and GpsB in Pneumococcal Cell Elongation and Division", PloS Genet 10(4), e1004275, 18 pages (2014).
Foss, et al., "Chemical-Biological Studies of Subcellular Organization in Bacteria", Biochemistry 50, 7719-7734 (2011).
Garner, et al., "Coupled, circumferential motions of the cell wall synthesis machinery and MreB filaments in B. subtilis", Science 333, 222-225 (2011).
Goffin, et al., "Biochemistry and Comparative Genomics of SxxK Superfamily Acyltransferases Offer a Clue to the Mycobacterial Paradox: Presence of Penicillin-Susceptible Target Proteins versus Lack of Efficiency of Penicillin as Therapeutic Agent", Microb Mol Biol Rev 66, 702-738 (2002).
Gordon, et al., "The crystal structure of the penicillin-binding protein 2x from Streptococcus pneumoniae and its acyl-enzyme form: implication in drug resistance", J Mol Biol 299, 477-485 (2000).
Hakenbeck, et al., "Molecular mechanisms of β-lactam resistance in Streptococcus pneumoniae", Future Microbiol 7, 395-410 (2012).
Kim, et al., "Cleavage of beta-lactone ring by serine protease. Mechanistic implications", Bioorg Med Chem 10, 2553-2560 (2002).
Kocaoglu, "Activity-Based Probes for Selective Penicillin-Binding Protein Visualization", Thesis submitted in partial fulfillment of the

(56) References Cited

OTHER PUBLICATIONS requirements for degree, Doctor of Philosophy in the Dept. of Molecular and Cellular Biochemistry Indiana University, Dec. 2014, 239 pages (sequestered through Dec. 22, 2016.).

Kocaoglu, et al., "Activity-Based Probes For Selective Penicillin-Binding Protein Visualization", Bioorganic Gordon Research Conference, Andover, NH, Jun. 5-10, 2016.

Kocaoglu, et al., "Profiling of β-Lactam Selectivity for Penicillin-Binding Proteins in *Escherichia coli* Strain DC2", Antimicrob. Agents Chemother. 59, 2785-2790 (2015).

Kocaoglu, et al., "Profiling of β-Lactam Selectivity for Penicillin-Binding Proteins in *Streptococcus pneumoniae* D39", Antimicrob. Agents Chemother. 59, 3548-3555 (2015).

Kocaoglu, et al., "Progress and prospects for small-molecule probes of bacterial imaging", Nat. Chem. Bio. 12, 472-478 (2016).

Kocaoglu, et al., "Selective Penicillin-Binding Protein Imaging Probes Reveal Substructure in Bacterial Cell Division", ACS Chem Biol 7, 1746-1753 (2012).

Krysiak, et al., "Quantitative Map of β-Lactone-Induced Virulence Regulation", J Proteome Res 16(3), 1180-1192 (2017).

Kuru, et al., "In Situ probing of newly synthesized peptidoglycan in live bacteria with fluorescent D-amino acids", Angew Chem Int Ed Engl 51, 12519-12523 (2012).

Lakaye, et al., "Synthesis, purification and kinetic properties of fluorescein-labelled penicillins", Biochem. J. 300 (Pt 1), 141-145 (1994).

Land, et al., "Requirement of Essential Pbp2x and GpsB for Septal Ring Closure in *Streptococcus pneumoniae* D39", Mol Microbiol 90, 939-955 (2013).

Landgraf, et al., "Segregation of molecules at cell division reveals native protein localization", Nat Methods 9, 480-482 (2012).

Lebar, et al., "Reconstitution of Peptidoglycan Cross-Linking Leads to Improved Fluorescent Probes of Cell Wall Synthesis", J Am Chem Soc 136, 10874-10877 (2014).

Li, et al., "Scaling Proteome-Wide Reactions of Activity-Based Probes", Anal Chem 89, 6295-6299 (2017).

Liechti, et al., "A new metabolic cell-wall labelling method reveals peptidoglycan in Chlamydia trachomatis", Nature 506, 507-510 (2014).

Liu, et al., "Activity-based protein profiling: the serine hydrolases", Proc Natl Acad Sci U S A 96, 14694-14699 (1999).

Macheboeuf, et al., "Penicillin binding proteins: key players in bacterial cell cycle and drug resistance processes", FEMS Microbiol Rev 30, 673-691 (2006).

Margolin, et al., "The Price of Tags in Protein Localization Studies", J Bacteriol 194, 6369-6371 (2012).

Massidda, et al., "From models to pathogens: how much have we learned about *Streptococcus pneumoniae* cell division?", Environ Microbiol 15, 3133-3157 (2013).

McPherson, et al., "Two Class A High-Molecular-Weight Penicillin-Binding Proteins of Bacillus subtilis Play Redundant Roles in Sporulation", J. Bacteriol. 183, 6046-6053 (2001).

Oh, et al., "Potential pharmacological chaperones targeting cancer-associated MCL-1 and Parkinson disease-associated α-synuclein", PNAS 111(30), 11007-11012 (2014).

Parker, et al., "SQ 26,517—A beta-Lactone Produced by a *bacillus* Species", J Antibiot 35, 900-902 (1982).

Pidgeon, et al., "Metabolic Profiling of Bacteria by Unnatural C-terminated D-Amino Acids", Angew Chem Int Ed Engl 54, 6158-6162 (2015).

Rowley, et al., "The site of action of penicillin. 1. Uptake of penicillin on bacteria", Biochem J 46, 157-161 (1950).

Rued, et al., "Suppression and Synthetic-Lethal Genetic Relationships of ΔgpsB Mutations Indicate That GpsB Mediates Protein Phosphorylation and Penicillin-Binding Protein Interactions in *Streptococcus pneumoniae* D39", Mol Microbiol 103, 931-97 (2017).

Sauvage, et al., "The penicillin-binding proteins: structure and role in peptidoglycan biosynthesis", Fems Microbiol Rev 32, 234-258 (2008).

Sauvage, et al., "The penicillin-binding proteins: structure and role in peptidoglycan biosynthesis", FEMS Microbiology Reviews 32(3), 556 (2008).

Scheffers, et al., "Several distinct localization patterns for penicillin-binding proteins in Bacillus subtilis", Mol Microbiol 51, 749-764 (2004).

\* cited by examiner

* protein concentration ~ 4.0 mg/ml

LACTONE-BASED PROBES AND METHODS OF USE THEREOF

PRIORITY

This application claims priority to U.S. Provisional Patent Application No. 62/510,663, filed 24 May 2017. The entire content of this United States Provisional patent application is hereby incorporated herein by reference.

GOVERNMENT FUNDING

This invention was made with government support under DP2OD008592-02, R01 AI107075, and R01 GM113172 awarded by the National Institutes of Health. The government has certain rights in the invention.

BACKGROUND

The cell wall integrity of most bacteria is dependent upon a complex polymeric structure, the peptidoglycan (PG) (Vollmer, W., et al. (2008) *FEMS Microbiol. Rev.* 32, 149-167). Inhibition of PG biosynthesis has yielded many antibacterial agents and although resistance has become a significant factor in antibiotic efficacy, it is clear that opportunities remain for the identification of novel antibiotic targets through a more complete understanding of the multiprotein molecular machines that dictate cell wall construction (Sauvage, E., et al. (2008) *FEMS Microbiol. Rev.* 32, 556-556). One of the major mechanisms by which existing antibacterial agents act is inhibition of the penicillin-binding proteins (PBPs), membrane-anchored enzymes involved in the PG polymerization (transglycosylation) and crosslinking (transpeptidation) steps required for cell wall synthesis and structural integrity (FIG. 1a) (Sauvage, E., et al. (2008) *FEMS Microbiol. Rev.* 32, 556-556). As the targets of the β-lactam antibiotics, which inhibit their transpeptidase activity, the PBPs have been therapeutically significant for many decades. Despite this importance, the discrete functions of individual PBP homologs have been difficult to determine because each enzyme is often dispensable for growth, possibly due to functional redundancy, and due to a lack of tools to assess the functional state of the PBPs in live bacterial cells (Sauvage, E., et al. (2008) *FEMS Microbiol. Rev.* 32, 556-556).

The PBPs are categorized into three classes based on their functional capacity. Class A high molecular weight (HMW) PBPs are bifunctional proteins with transglycosylase (TG) and transpeptidase (TP) activities. Class B HMW PBPs are monofunctional TPs. Class C or low molecular weight (LMW) PBPs are D,D-carboxypeptidase or D,D-endopeptidases (Macheboeuf, P., et al. (2006) *FEMS Microbiol. Rev.* 30, 673-691) that play a major role in regulation of crosslinking between glycan chains (McPherson, D. C., et al. (2001) *J. Bacteriol.* 183, 6046-6053). All PBPs possess a catalytic serine in their peptidase domain, which is required for substrate turnover and is the site for covalent modification by the β-lactam antibiotics (FIGS. 1b and 1c) (Waxman, D. J., et al. (1983) *Annu. Rev. Biochem.* 52, 825-869). Because the hydrolysis of the β-lactam complex is slow, these molecules occupy the active site for extended periods, thus preventing the enzyme from catalyzing further reactions and often leading to cell lysis (Gordon, E., et al. (2000) *J. Mol. Biol.* 299, 477-485; and Goffin, C., et al. (2002) *Microb. Mol. Biol. Rev.* 66, 702-738).

Since it was determined that penicillin V acts as a global PBP inhibitor, β-lactams have been used as probes to gain insight into bacterial physiology (Falconer, S. B., et al. (2011) *Nat. Chem. Biol.* 7, 415-423; and Böttcher, T., et al. (2012) *Med. Chem. Commun.* 3, 408-417). A standard strategy for profiling of PBP activity is tagging with a radiolabeled penicillin, separation by gel electrophoresis (SDS-PAGE) and detection by fluorography (Spratt, B. G., et al. (1975) *Nature* 254, 516-517). Although not a direct quantitative measure of PBP activity, this suicide inhibitor provides information about the catalytic activity state of these proteins, since inactive PBPs are not acylated, and V-based penicillins can be used in kinetic binding and inhibitor assays to determine PBP concentration (Waxman, D. J., et al. (1983) *Annu. Rev. Biochem.* 52, 825-869; and Bush, K., et al. (1987) *Agents Chemother.* 31, 1271-1273). However, radioactive compounds cannot be used for in vivo visualization, and penicillin V-based compounds label all PBPs, preventing discrete characterization of each homolog.

Single PBPs can be studied with fluorescently-labeled protein constructs, however, artificial fusions can perturb protein concentration, function, or localization (Scheffers, D. J., et al. (2004) *Mol. Microbiol.* 51, 749-764; Landgraf, D., et al. (2012) *Nat. Methods* 9, 480-482; Margolin, W. (2012) *J. Bacteriol.* 194, 6369-6371; Dominguez-Escobar, J., et al. (2011) *Science* 333, 225-228; Garner, E. C., et al. (2011) *Science* 333, 222-225; and Swulius, M. T., et al. (2012) *J. Bacteriol.* 194, 6382-6386). Moreover, PBP protein localization does not provide information about activity state. Alternatively, small molecule-conjugated fluorophores can provide temporal resolution without genetic manipulation. Several strategies have been reported for imaging nascent PG including fluorophore-conjugated vancomycin (Van-FL) and ramoplanin, which label PG biosynthetic precursors in various Gram-positive bacteria (Daniel, R. A., et al. (2003) *Cell* 113, 767-776; and Tiyanont, K., et al. (2006) *Proc. Natl. Acad. Sci. USA* 103, 11033-11038). In addition, D-amino acid analogs that either bear a fluorophore or a bioorthogonal handle have been incorporated into the stem peptide during PG synthesis (fluorescent D-amino acids; FDAAs) (Kuru, E., et al. (2012) *Angew. Chem. Int. Ed. Engl.* 51, 12519-12523; Siegrist, M. S., et al. (2013) *ACS Chem. Biol.* 8, 500-503; Shieh, P., et al. (2014) *Iproc. Natl. Acad. Sci. USA* 111, 5456-5461; Lebar, M. D., et al. (2014) *J. Am. Chem. Soc.* 136, 10874-10877; and Pidgeon, S. E., et al. (2015) *Angew Chem Int Ed Engl* 54, 6158-6162). FDAAs are being used in many investigations (Bisson-Filho, A. W., et al. (2017) *Science* 355, 739-743; Liechti, G. W., et al. (2014) *Nature* 506, 507-510; and Fleurie, A., et al. (2014) *PloS Genet.* 10, e1004275), and we have used them extensively to study aspects of *Streptococcus pneumoniae* PG biosynthesis, including the spatial separation of the PG synthesis machines (Tsui, H. C., et al. (2014) *Mol. Microbiol.* 94, 21-40; and Rued, B. E., et al. (2017) *Mol. Microbiol.* 103, 931-957) and lack of PG turnover and recycling (Boersma, M. J., et al. (2015) *J. Bacteriol.* 197, 3472-3485). While FDAA probes are powerful tools, their non-specificity for individual PBPs can only indicate regions of the cell where there is TP activity (Boersma, M. J., et al. (2015) *J. Bacteriol.* 197, 3472-3485). Likewise, although an important research tool, the commercially available fluorophore-conjugated penicillin V analog, BOCILLIN-BODIPY FL (Boc-FL; 1 in FIG. 2a) (Zhao, G., et al. (1999) *Antimicrob. Agents Chemother.* 43, 1124-1128; and Lakaye, B., et al. (1994) *Biochem. J.* 300, 141-145) is non-specific and labels all PBPs.

To enable dissection of the distinct roles played by the enzymes responsible for PG synthesis, small molecules that selectively target individual PBPs in an activity-dependent fashion are required. Several groups have synthesized β-lactam-based probes for in vitro protein labeling, largely yielding compounds that label both PBPs and other bacterial proteins (Staub, I., et al. (2008) *J. Am. Chem. Soc.* 130, 13400-13409; Dargis, M., et al. (1994) *Antimicrob Agents Ch* 38, 973-980). Currently, one third of *S. pneumoniae* strains are found to be resistant to at least one of the prescribed antibiotics. This resistance often occurs by mutations in genes encoding PBPs. In addition to being a clinically significant organism, *S. pneumoniae* is an important model in which to study PG biosynthesis as it possesses a relatively simple PBP complement with three class A PBPs (PBP1a, PBP1b, and PBP2a), two class B PBPs (PBP2x and PBP2b), and one class C PBP (PBP3 or DacA; D,D-carboxypeptidase) (Land, A. D., et al. (2013) *Mol. Microbiol.* 90, 939-955; Massidda, O., et al. (2013) *Environ. Microbiol.* 15, 3133-3157; and Hakenbeck, R., et al. (2012) *Future Microbiol.* 7, 395-410). Molecules based on cephalosporin C were utilized in combination with Boc-FL to separate the catalytic activity of PBP1b from that of PBP1a, PBP2x, PBP2a and PBP2b. Intriguingly, these studies indicate that different populations of PBPs may be active at discrete locations during division. Clearly, tools that facilitate deeper examination of this issue will be instrumental in teasing apart the complex biology of the PBP family.

Design of probes to target individual PBP homologs requires the identification of scaffolds that selectively inhibit each enzyme. The evaluation of 20 commercially available β-lactams from the five classes of clinically utilized compounds for selective PBP inhibition in *S. pneumoniae* and *Escherichia coli*. Was recently reported (Kocaoglu, O., and et al. (2015) *Antimicrob. Agents Chemother.* 59, 2785-2790; and Kocaoglu, O., et al. (2015) *Antimicrob. Agents Chemother.* 59, 3548-3555). Several compounds may provide the foundation for generation of selective probes; however, many PBPs are poorly inhibited by existing β-lactams.

Lactones are biologically active compounds that have been shown to covalently modify enzymes (Kim, D. H., et al. (2002) *Bioorg. Med. Chem.* 10, 2553-2560), such as tetrahydrolipstatin (Orlistat), the long-term anti-obesity drug that functions by inhibition of a lipase, which is the only Food and Drug Administration approved β-lactone (Venukadasula, P. K. M., et al. (2010) *Org. Lett.* 12, 1556-1559). Despite their structural similarity to the β-lactams, β-lactones (2-oxetanones) have garnered significantly less attention for the treatment of infectious disease. Natural products containing this moiety were first reported ~50 years ago (Wells, J. S., et al. (1982) *J. Antibiot.* (Tokyo) 35, 814-821; and Aldridge, D. C., et al. (1971) *J. Chem. Soc. Perkin* 1 23, 3888-3891) and only a small number of β-lactones are known to possess antibiotic activity, including obafluorin (Tymiak, A. A., et al. (1985) *J. Org. Chem.* 50, 5491-5495), SQ 26,517 (Wells, J. S., et al. (1982) *J. Antibiot.* (Tokyo) 35, 814-821; and Parker, W. L., et al. (1982) *J. Antibiot.* 35, 900-902), and hymeglusin (Aldridge, D. C., et al. (1971) *J. Chem. Soc. Perkin* 1 23, 3888-3891) (FIG. 2a). Obafluorin provides protection in mice infected with *S. pyogenes* and causes cell elongation in *E. coli*, perhaps suggesting inhibition of cell wall biosynthesis. It was also the first example of a β-lactone substrate of a β-lactamase enzyme (Wells, J. S., et al. (1984) *J. Antibiot.* 37, 802-803). However, the targets of the β-lactones that yield their antibacterial activity remain undetermined. More recently, synthetic β-lactones were shown to inhibit proteins involved in primary and secondary metabolism, antibiotic resistance, an additional β-lactamase, PBP4* in *Bacillus subtilis*, and a virulence-associated protein, caseinolytic protease P (ClpP) (Bottcher, T., et al. (2008) *Angewandte Chemie* 47, 4600-4603; Böttcher, T., et al. (2008) *J. Am. Chem. Soc.* 130, 14400-14401; Böttcher, T., et al. (2008) *Angew. Chem. Int. Ed. Engl.* 47, 4600-4603; Zeiler, E., et al. (2011) *Angew. Chem. Int. Ed. Engl.* 50, 11001-11004; Zhao, W., et al. (2016) *Chem. Commun.* 52, 11971-11974; Compton, C. L., et al. (2013) *ACS Chem. Biol.* 8, 2669-2677; and Krysiak, J., et al. (2017) *J. Proteome Res.*. Doi: 10.1021/acs.jproteome.6b00705).

Currently, there is a need for new agents that are useful for detecting PBPs.

SUMMARY

In one aspect the present invention provides conjugates having affinity for one or more PBPs that are useful for detecting PBPs in a cell or in a cell fraction comprising one or more PBPs.

Accordingly, the invention provides a conjugate of formula I:

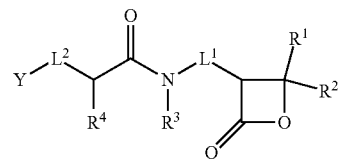

or a salt thereof, wherein:

$R^1$ is H, $(C_1-C_6)$alkyl, $(C_1-C_6)$alkoxyl, aryl, heteroaryl, or 4-8 membered heterocycle; wherein the $(C_1-C_6)$alkyl is optionally substituted with one or more groups independently selected from halo, —$OR^a$, —CN, —$NO_2$, -oxo-, —$N(R^a)_2$, —$CO_2R^a$, aryl, heteroaryl, or 4-8 membered heterocycle, wherein any aryl, heteroaryl, and 4-8 membered heterocycle is optionally substituted with one or more groups independently selected from halo, —$OR^a$, —CN, —$NO_2$, -oxo-, —$N(R^a)_2$, or —$CO_2R^a$;

$R^2$ is H or $(C_1-C_6)$alkyl;

$R^3$ is H or $(C_1-C_6)$alkyl;

$R^4$ is H, $(C_1-C_6)$alkyl, $(C_1-C_6)$alkoxyl, aryl, heteroaryl, or 4-8 membered heterocycle; wherein the $(C_1-C_6)$alkyl is optionally substituted with one or more groups independently selected from halo, —$OR^b$, —CN, —$NO_2$, -oxo-, —$N(R^b)_2$, —$CO_2R^b$, aryl, heteroaryl, or 4-8 membered heterocycle, wherein any aryl, heteroaryl, and 4-8 membered heterocycle is optionally substituted with one or more groups independently selected from halo, —$OR^b$, —CN, —$NO_2$, -oxo-, —$N(R^b)_2$, or —$CO_2R^b$;

$L^1$ is absent or $(C_1-C_4)$alkylene;

$L^2$ is absent or a linking group;

Y is —$N_3$, $(C_2-C_6)$alkynyl, 3-8 membered cycloalkyl comprising at least one triple bond, 1,2,4,5-tetrazinyl which is optionally substituted with $(C_1-C_6)$alkyl, biotin, or a detectable group;

each $R^a$ is independently hydrogen or $C_{1-4}$ alkyl; or two $R^a$ groups taken together with the nitrogen to which they are attached form pyrrolidinyl, piperidinyl, piperazinyl or morpholinyl; and each $R^b$ is independently hydrogen or $C_{1-4}$ alkyl; or two $R^b$ groups taken together with the nitrogen to which they are attached form pyrrolidinyl, piperidinyl, piperazinyl or morpholinyl.

The invention also provides a composition comprising a compound of formula I or a salt thereof, and an excipient.

The invention also provides a pharmaceutical composition comprising a compound of formula I or a pharmaceutically acceptable salt thereof, and a pharmaceutically acceptable excipient.

The invention also provides a method for labeling one or more PBPs comprising contacting the one or more PBPs with a compound of formula I or a salt thereof to provide one or more labeled PBPs, wherein the compound binds to the one or more PBPs.

The invention also provides processes and intermediates disclosed herein that are useful for preparing a compound of formula I or a salt thereof.

BRIEF DESCRIPTION OF THE FIGURES

FIG. 1a shows transglycosylase and transpeptidase reactions are catalyzed by the PBPs. The PG is comprised of lipid II subunits, which are linked together through the actions of these proteins. FIG. 1b shows mechanism of transpeptidation; PBPs form an acyl-enzyme intermediate, resulting in cleavage of a D-Ala residue of the first stem peptide. Next, a neighboring group intercepts this activated intermediate to yield cross-linked peptidoglycan. FIG. 1c shows active site serine attacks the β-lactam ring found in this class of antibiotics, leading to covalent modification of the PBP and preventing further catalysis.

FIG. 2a shows structures of BOCILLIN-FL and three lactone-containing molecules previously found to possess activity in bacteria. FIG. 2b shows lactone probes bearing one of three fluorophores: 5-carboxytetramethylrhodamine (TAMRA, T), 5-fluorescein (FL), and boron-dipyrromethene (BODIPY, B). These probes include a stereochemical mimic of biologically-active β-lactams (2S,3R-β-lactone; 2T, FL, B), the opposite isomer (2R,3S-β-lactone; 3T, B) and a five-membered ring δ-lactone (4FL). FIG. 2c shows amino acid components were incorporated to yield a diverse pool of probes including those with functional groups found in the natural peptidoglycan substrate, D-Ala (5) and the opposite stereoisomer L-Ala (6), or in β-lactam antibiotics, L-Phe (7), D-Phe (8) and L-Tyr (9), and Gly to assess the importance of the side chain (10). Finally, two additional hydrophobic amino acids were incorporated, L-Val (11) and L-Trp (12).

FIG. 3a shows TAMRA-functionalized probes. (2S, 3R)-β-lactone (2T) and (2R, 3S)-β-lactone (3T) showed dramatically different labeling profiles with the former tagging PBP1a, PBP1b, PBP2x and PBP2a and the later labeling nothing. Addition of a glycine residue between the lactone and fluorophore group (10T) altered the labeling profile to include PBP2b, but not PBP2a. Marked differences in selectivity were noted with alanine-functionalized compounds. The D-Ala-based probe (amino acid stereochemistry found in stem peptide; 5T) labeled all HMW PBPs, while the L-Ala-functionalized molecule was more selective (6T; PBP1b and PBP2x). FIG. 3b shows fluorescein-functionalized probes. PBP labeling with 2FL and 6FL is comparable to the TAMRA probes. However, the D-Ala-based probe (5FL; PBP1b and PBP2x) tagged dramatically fewer PBPs than the TAMRA analog (5T). All probes were assessed at 5 μg/ml.

DETAILED DESCRIPTION

Figure 1A:
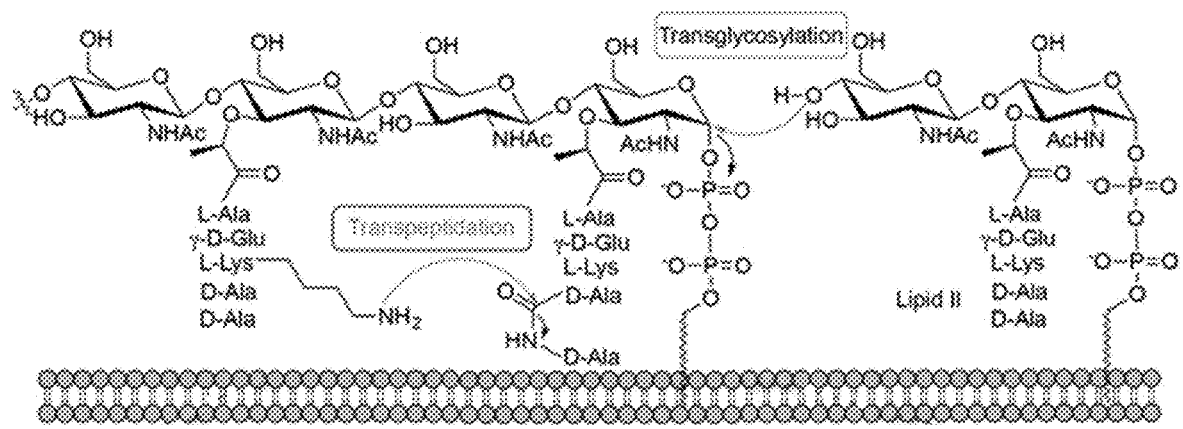
FIGS. 1a-1c show bacterial cell wall biosynthesis requires the actions of the penicillin-binding proteins.
Figure 1B:
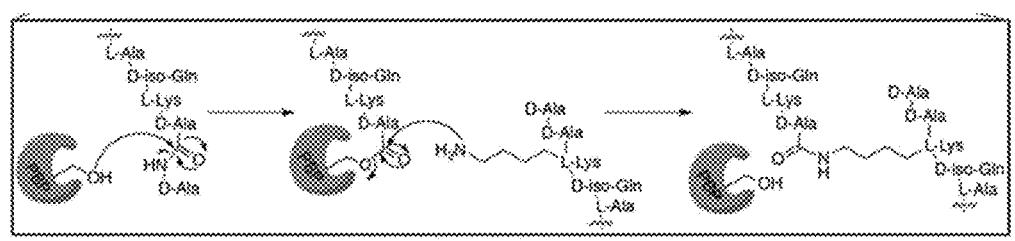
Figure 1C:
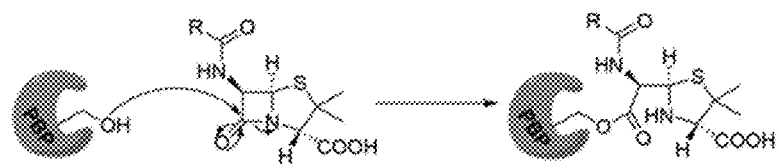

The following definitions are used, unless otherwise described: halo or halogen is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples include ($C_1$-$C_8$)alkyl, ($C_2$-$C_8$)alkyl, $C_1$-$C_6$)alkyl, ($C_2$-$C_6$)alkyl and ($C_3$-$C_6$)alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and and higher homologs and isomers.

The term "alkynyl" refers to an unsaturated alkyl radical having one or more triple bonds. Examples of such unsaturated alkyl groups ethynyl, 1- and 3-propynyl, 3-butynyl, and higher homologs and isomers.

The term "alkylene" by itself or as part of another substituent means a divalent radical derived from an alkane (including straight and branched alkanes), as exemplified by —$CH_2$—, —$CH_2CH_2CH_2CH_2$— and —$CH(CH_3)CH_2CH_2$—.

The term "alkoxy" refers to an alkyl group attached to the remainder of the molecule via an oxygen atom ("oxy"). Examples of "alkoxy" include methoxy, ethoxy, propoxy, isopropoxy, butoxy, iso-butoxy, sec-butoxy, pentoxy, 3-pentoxy, or hexyloxy.

The term "cycloalkyl" refers to a saturated or partially unsaturated all carbon ring having 3 to 8 carbon atoms (i.e., ($C_3$-$C_8$)carbocycle). The term also includes multiple condensed, saturated or partially unsaturated all carbon ring systems (e.g., ring systems comprising 2, 3 or 4 carbocyclic rings). Accordingly, carbocycle includes multicyclic carbocyles such as a bicyclic carbocycles (e.g., bicyclic carbocycles having about 3 to 15 carbon atoms, about 6 to 15 carbon atoms, or 6 to 12 carbon atoms such as pneumon [3.1.0]hexane and pneumon[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, pneumon [2.2.2]octane, etc). Non-limiting examples of cycloalkyls include cyclopropyl, cyclobutyl, cyclopentyl, cyclohexyl, pneumon[2.2.1]heptane, pneumo, and *pneumoniae*.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., cycloalkyl. Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, indanyl, naphthyl, 1, 2, 3, 4-tetrahydronaphthyl, anthracenyl, and the like.

The term "heterocycle" refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from cycloalkyl, aryl, and heterocycle to form the multiple condensed ring system. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. In one embodiment the term heterocycle includes a 3-15 membered heterocycle. In one embodiment the term heterocycle includes a 3-8 membered heterocycle. In one embodiment the term heterocycle includes a 3-6 membered heterocycle. In one embodiment the term heterocycle includes a 4-6 membered heterocycle. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one imidazolidine, pyrazolidine, butyrolactam, valerolactam, imidazolidinone, hydantoin, dioxolane, phthalimide, and 1,4-dioxane.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such heteroaryl ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from cycloalkyl, aryl, heterocycle and heteroaryl It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, triazolyl, tetrazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, and quinazolyl.

As used herein a wavy line " " that intersects a bond in a chemical structure indicates the point of attachment of the bond that the wavy bond intersects in the chemical structure to the remainder of a molecule.

The compounds disclosed herein can also exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —CH$_3$ group may be substituted with —CD$_3$.

The compositions of the invention can comprise one or more excipients. When used in combination with the compositions of the invention the term "excipients" refers generally to an additional ingredient that is combined with the compound of formula (I) or salt thereof to provide a corresponding composition. For example, when used in combination with the compositions of the invention the term "excipients" includes, but is not limited to: carriers, binders, disintegrating agents, lubricants, sweetening agents, flavoring agents, coatings, preservatives, and dyes.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

A detectable group includes, but is not limited to, a fluorescent group and a chelating group, which may be labeled with radionuclides.

In certain embodiments, the detectable group comprises a chelating group, which may be labeled with a radionuclide. Any suitable chelating group can be employed. Suitable chelating groups are disclosed, e.g., in Rockey et al., Bioorganic & Medicinal Chemistry 19 (2011) 4080-4090; Poster Sessions, Proceedings of the 46$^{th}$ Annual Meeting, J. Nuc. Med., p. 316, No. 1386; Scientific Papers, Proceedings of the 46$^{th}$ Annual Meeting, J. Nuc. Med., p. 123, No. 499; Scientific Papers, Proceedings of the 46$^{th}$ Annual Meeting, J. Nuc. Med., p. 102, No. 413; Scientific Papers, Proceedings of the 46$^{th}$ Annual Meeting, J. Nuc. Med., p. 102, No. 414; Scientific Papers, Proceedings of the 46$^{th}$ Annual Meeting, J. Nuc. Med., p. 103, No. 415; Poster Sessions, Proceedings of the 46$^{th}$ Annual Meeting, J. Nuc. Med., p. 318, No. 1396; Poster Sessions, Proceedings of the 46$^{th}$ Annual Meeting, J. Nuc. Med., p. 319, No. 1398; M. Moi et al., J. Amer. Chem., Soc., 49, 2639 (1989); S. V. Deshpande et al., J. Nucl. Med., 31, 473 (1990); G. Kuser et al., Bioconj. Chem., 1, 345 (1990); C. J. Broan et al., J. C. S. Chem. Comm., 23, 1739 (1990); C. J. Anderson et al., J. Nucl. Med. 36, 850 (1995); U.S. Pat. No. 5,739,313; and U.S. Pat. No. 6,004,533.

In certain embodiments, the detectable group comprises a fluorescent group. A fluorescent group is also called a "fluorescent tag" or a "fluorophore". A fluorophore is a molecule that absorbs light (i.e., excites) at a characteristic wavelength and emits light (i.e. fluoresces and emits a signal) at a second lower-energy wavelength. The detectable agent may include, but is not limited to, one or more of the following fluorescent groups: fluorescein, tetrachlorofluorescein, hexachlorofluorescein, tetramethylrhodamine, rhodamine, cyanine-derivative dyes, Texas Red, Bodipy, and Alexa dyes. Examples of certain fluorophores are listed at www.researchservices.umn.edu/sites/researchservices.umn-.edu/files/configuration-lsrfortessa-h0081.pdf, which is incorporated by reference herein, which includes, e.g., FITC, GFP, 488 B, Brilliant Blue 515, CFSE, 7-AAD, PerCP, PerCP-Cy5-5, 488 A, PerCP-eFluor 710, SSC, APC-Cy7, APC-H7, 640A, APC-Alexa Fluor 750, APC-eFluor 780, Alexa Fluor 647, APC, 640 C, Sytox Red, Alexa Fluor 700, 640 B, Qdot 705, 405 B, Brilliant Violet 711, Qdot 605, 405 D, Brilliant Violet 605, eFluor 605, Pacific Blue, 405 F, Brilliant Violet 421, DyeCycle Violet, eFluor 450, Horizon v450, Qdot 800, 405 A, Brilliant Violet 786, Qdot 655, 405 C, Brilliant Violet 650, eFluor 650, Pacific Orange, 405 E, Brilliant Violet 510, Horizon v500, L/D Fixable Aqua, PE-Cy7, 561 A, DsRed, PE, 561 C, Cy3, tdTomato, PE-CF594, PE-Texas Red, PI, 561 B, mCherry, PE-Alexa Fluor, 355 B, Brilliant Ultraviolet 737, Alexa Fluor 350, 355 D, Brilliant Ultraviolet 395, 355 A, Brilliant Ultraviolet 805, 355 C and Brilliant Ultraviolet 496. Characteristic absorption and emission wavelengths for each of these are well known to those of skill in the art.

In certain embodiments, the fluorophore is one or more of the fluorophores listed in Table 1.

TABLE 1

| Probe | Excitation (nm) | Emission (nm) |
|---|---|---|
| Hydroxycoumarin | 325 | 386 |
| Alexa fluor | 325 | 442 |
| Aminocoumarin | 350 | 445 |
| Methoxycoumarin | 360 | 410 |
| Cascade Blue | (375); 401 | 423 |
| Pacific Blue | 403 | 455 |
| Pacific Orange | 403 | 551 |
| Lucifer yellow | 425 | 528 |
| Alexa fluor 430 | 430 | 545 |
| NBD | 466 | 539 |
| R-Phycoerythrin (PE) | 480; 565 | 578 |
| PE-Cy5 conjugates | 480; 565; 650 | 670 |
| PE-Cy7 conjugates | 480; 565; 743 | 767 |
| Red 613 | 480; 565 | 613 |
| PerCP | 490 | 675 |
| Cy2 | 490 | 510 |
| TruRed | 490, 675 | 695 |
| FluorX | 494 | 520 |
| Fluorescein | 495 | 519 |
| FAM | 495 | 515 |
| BODIPY-FL | 503 | 512 |
| TET | 526 | 540 |
| Alexa fluor 532 | 530 | 555 |
| HEX | 535 | 555 |
| TRITC | 547 | 572 |
| Cy3 | 550 | 570 |
| TMR | 555 | 575 |
| Alexa fluor 546 | 556 | 573 |
| Alexa fluor 555 | 556 | 573 |
| Tamara | 565 | 580 |
| X-Rhodamine | 570 | 576 |
| Lissamine Rhodamine B | 570 | 590 |
| ROX | 575 | 605 |
| Alexa fluor 568 | 578 | 603 |
| Cy3.5 581 | 581 | 596 |
| Texas Red | 589 | 615 |
| Alexa fluor 594 | 590 | 617 |
| Alexa fluor 633 | 621 | 639 |
| LC red 640 | 625 | 640 |
| Allophycocyanin (APC) | 650 | 660 |
| Alexa fluor 633 | 650 | 688 |
| APC-Cy7 conjugates | 650; 755 | 767 |
| Cy5 | 650 | 670 |
| Alexa fluor 660 | 663 | 690 |
| Cy5.5 | 675 | 694 |
| LC red 705 | 680 | 710 |
| Alexa fluor 680 | 679 | 702 |
| Cy7 | 743 | 770 |
| IRDye 800 CW | 774 | 789 |
| Alexa Fluor 488 | 490 | 525 |
| Alexa Fluor 647 | 650 | 665 |
| Brilliant Violet 421 | 405 | 421 |

In certain in vivo embodiments, the fluorophore emits in the near infrared range, such as in the 650-900 nm range. (Weissleder et al., "Shedding light onto live molecular targets, *Nature Medicine,* 9:123-128 (2003)).

Compounds

In one embodiment, $R^1$ and $L^1$ are in (cis)-configuration.

In one embodiment, $R^1$ and $L^1$ are in (trans)-configuration.

In one embodiment, the compound of invention has the following formula Ia:

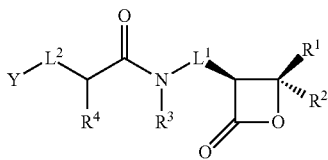

Ia or a salt thereof.

In one embodiment, $R^1$ is H, $(C_1-C_6)$alkyl, or phenyl; wherein the $(C_1-C_6)$alkyl is optionally substituted with one or more groups independently selected from halo, —$OR^a$, or phenyl, wherein any phenyl is optionally substituted with one or more groups independently selected from halo, —$OR^a$, —CN, —$NO_2$, -oxo-, —$N(R^a)_2$, or —$CO_2R^a$.

In one embodiment, $R^1$ is H, methyl, trifluoromethyl, methoxymethyl, phenyl, benzyl, or 4-nitrobenzyl.

In one embodiment, $R^1$ is methyl

In one embodiment, $R^2$ is H or methyl.

In one embodiment, $R^2$ is H.

In one embodiment, $L^1$ is absent or methylene.

In one embodiment, the group

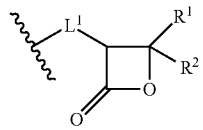

is selected from the group consisting of:

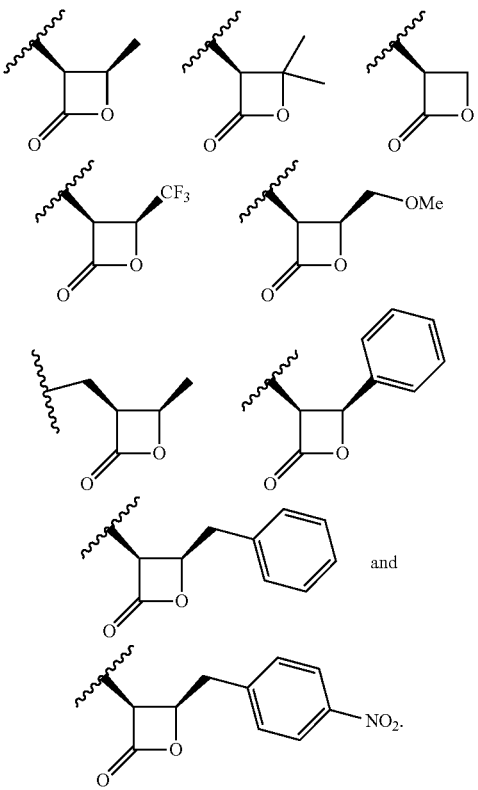

and

In one embodiment, $R^3$ is H.

In one embodiment, $R^4$ is H or $(C_1-C_6)$alkyl; wherein the $(C_1-C_6)$alkyl is optionally substituted with one or more groups independently selected from halo, —$OR^b$, —CN, —$NO_2$, -oxo-, —$N(R^b)_2$, —$CO_2R^b$, aryl, heteroaryl, or 4-8 membered heterocycle, wherein any aryl, heteroaryl, and 4-8 membered heterocycle is optionally substituted with one or more groups independently selected from halo, —$OR^b$, —CN, —$NO_2$, -oxo-, —$N(R^b)_2$, or —$CO_2R^b$.

In one embodiment, $R^4$ is H or $(C_1-C_6)$alkyl; wherein the $(C_1-C_6)$alkyl is optionally substituted with one or more groups independently selected from halo, —$OR^b$, —CN, —$NO_2$, -oxo-, —$N(R^b)_2$, or —$CO_2R^b$.

In one embodiment, $R^4$ is H, methyl, isopropyl,

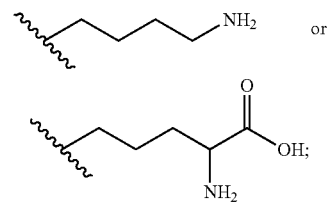

or a salt thereof.

In one embodiment, $R^4$ is $(C_1-C_6)$alkyl which is substituted with one or more groups independently selected from aryl, heteroaryl, or 4-8 membered heterocycle, wherein any aryl, heteroaryl, and 4-8 membered heterocycle is optionally substituted with one or more groups independently selected from halo, —$OR^b$, —CN, —$NO_2$, -oxo-, —$N(R^b)_2$, or —$CO_2R^b$.

In one embodiment, $R^4$ is

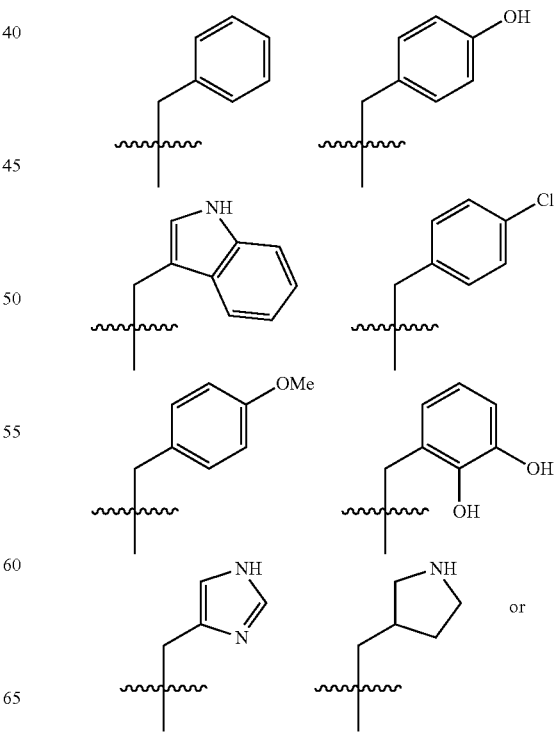

-continued

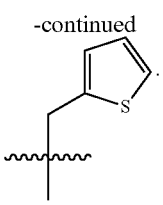

In one embodiment, $L^2$ has a molecular weight of from about 20 daltons to about 600 daltons.

In one embodiment, $L^2$ has a molecular weight of from about 50 daltons to about 300 daltons.

In another embodiment, $L^2$ has a length of about 5 angstroms to about 60 angstroms.

In another embodiment, $L^2$ separates Y from the remainder of the compound of formula I by about 5 angstroms to about 40 angstroms, inclusive, in length.

In one embodiment, $L^2$ is a divalent, branched or unbranched, saturated or unsaturated, hydrocarbon chain, having from 1 to 20 carbon atoms, wherein one or more of the carbon atoms in the hydrocarbon chain is optionally replaced by —O—, —$NR^L$—, or —S—; wherein the hydrocarbon chain is optionally substituted with one or more substituents selected from halo, oxo, —$OR^L$, —$N(R^L)_2$, or —$CO_2R^L$; wherein each $R^L$ is independently hydrogen or $(C_1$-$C_6)$alkyl.

In one embodiment, $L^2$ is

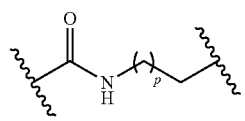

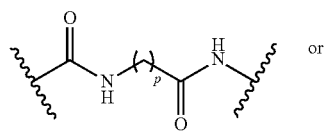

or

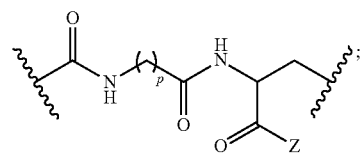

wherein Z is OH or $NH_2$; and
each p is independently 1, 2, 3, 4, 5, 6, 7, 8, 9 or 10.
In one embodiment, $L^2$ is

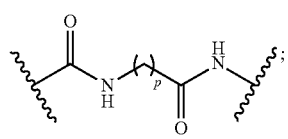

wherein p is 3, 4, 5, 6, 7, or 8.

In one embodiment, $L^2$ is —C(=O)NH(CH$_2$)$_3$CH$_2$— or —C(=O)NH(CH$_2$)$_5$C(=O)NH—.

In one embodiment, $L^2$ is —C(=O)NH—.

In one embodiment, Y is a fluorescent group; wherein Y is linked to $L^2$ at any synthetically feasible position of Y.

In one embodiment, Y comprises a core structure selected from the group consisting of coumarin, hydroxyphenylquinazolinone (HPQ), dicyanomethylenedihydrofuran (DCDHF), fluorescein, carboxyfluorescein, rhodol, rhodamine, carboxytetramethylrhodamine (TAMRA), rosamine, boron-dipyrromethene (BODIPY), fluorescein (FL), resorufin, acridinone, and indocarbocyanine, and an analog thereof.

In one embodiment, Y is

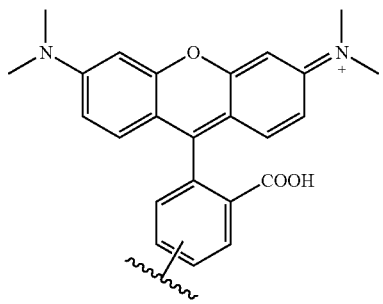

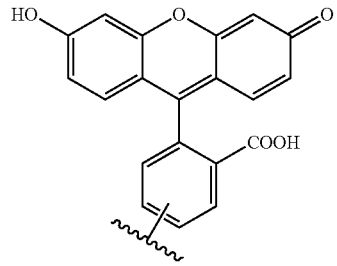

or

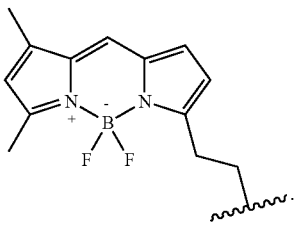

One embodiment of the invention provides a compound of formula I, which is selected from the group consisting of:

2FL
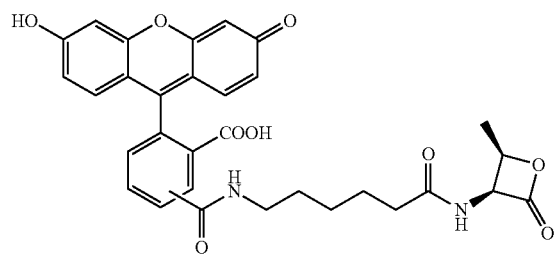
2B
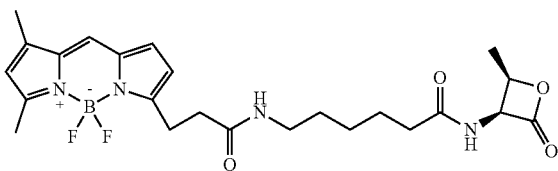
2T
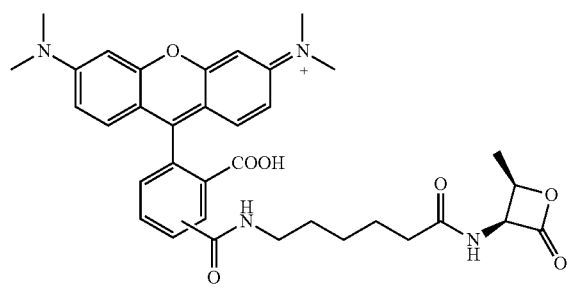
3T
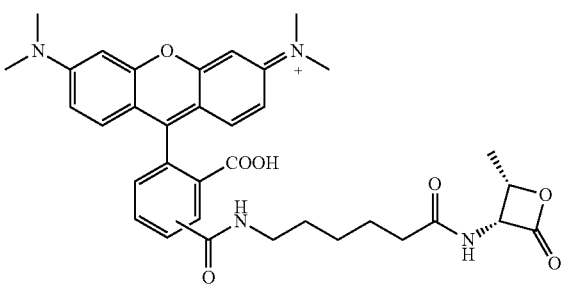
5T
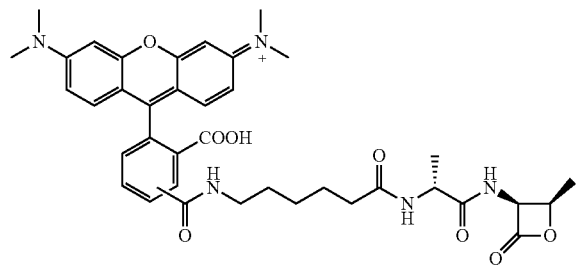
5FL
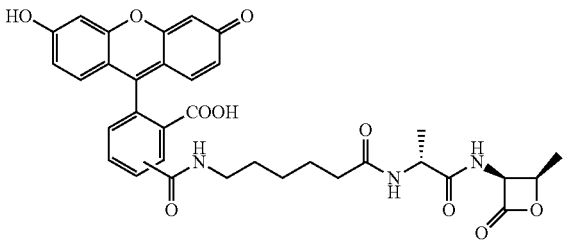
5B
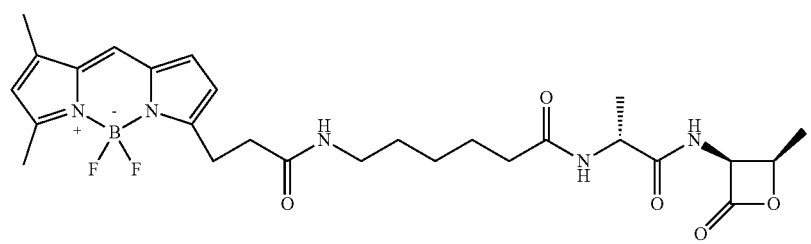
6T
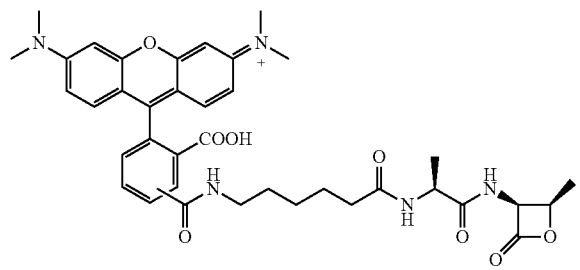
6FL
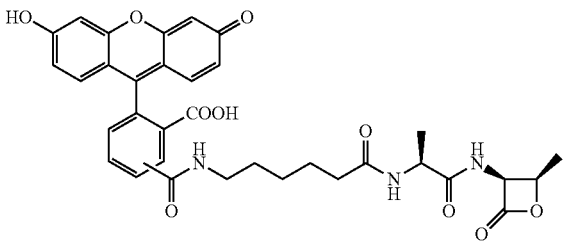

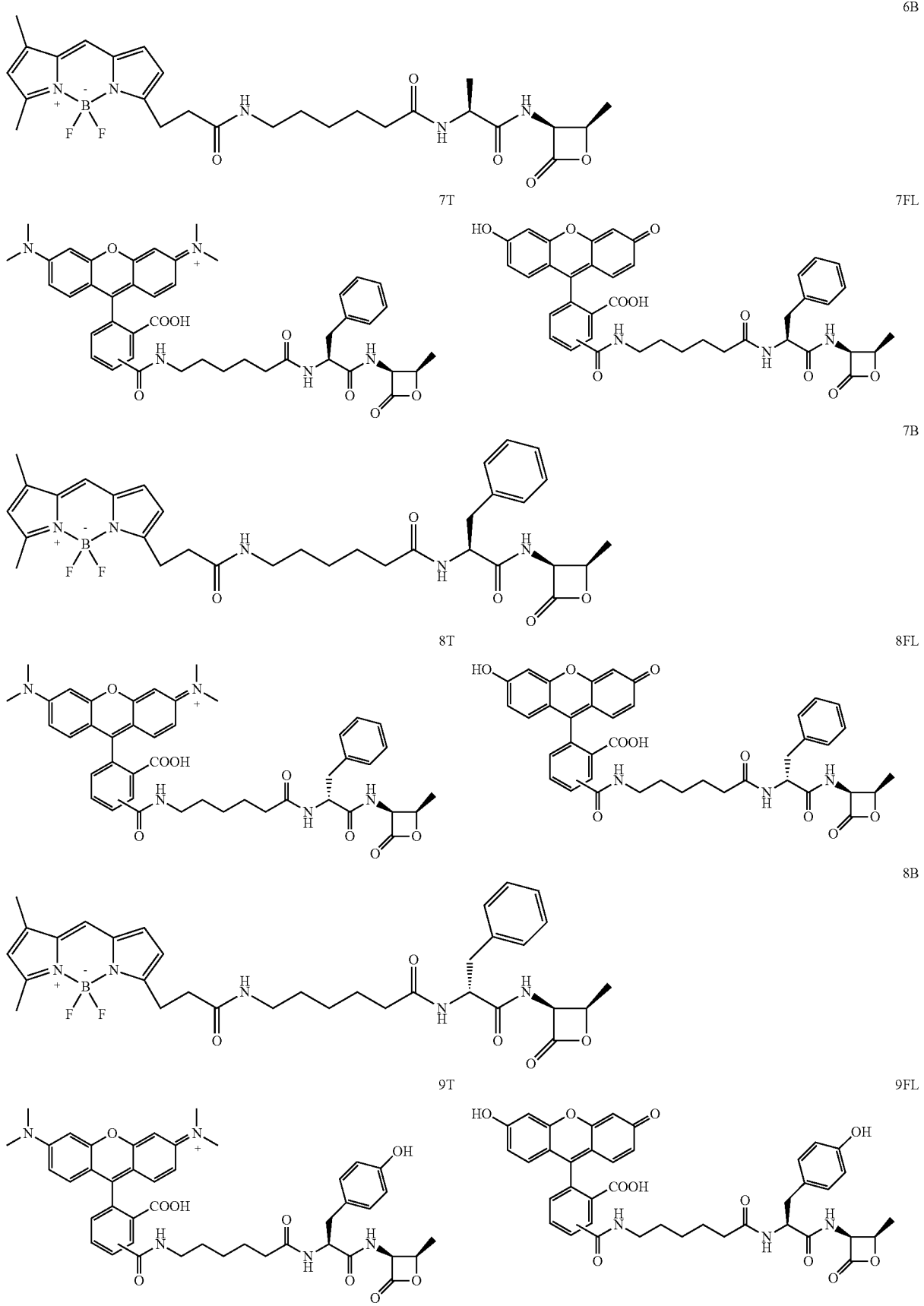

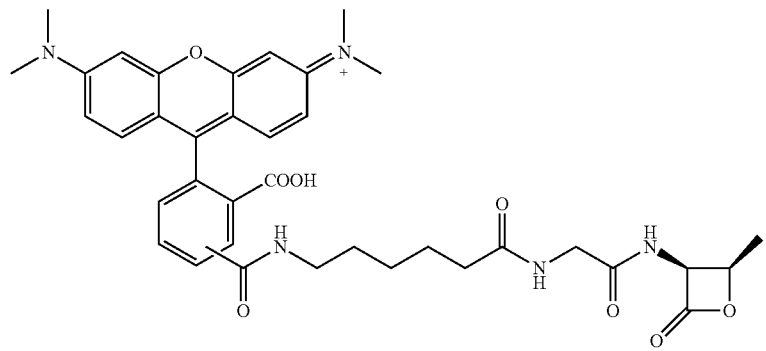
10T
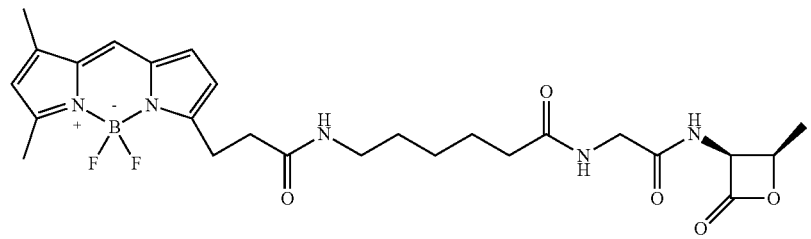
10B
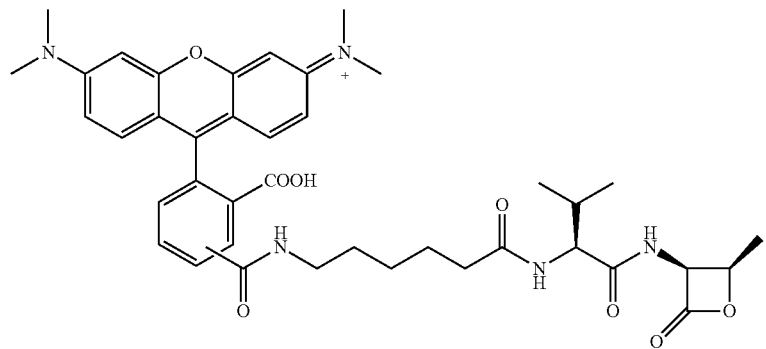
11T
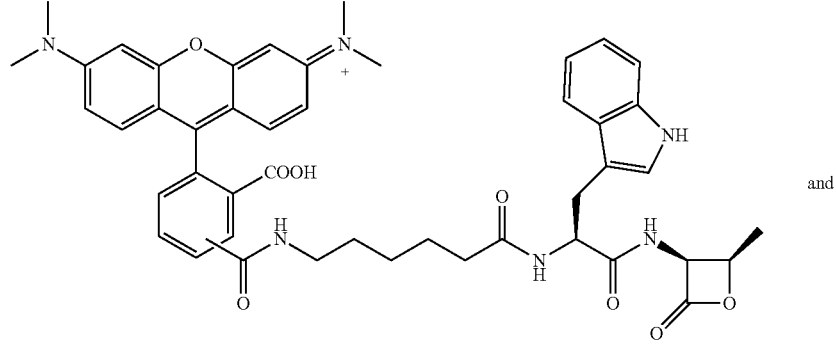
12T
and
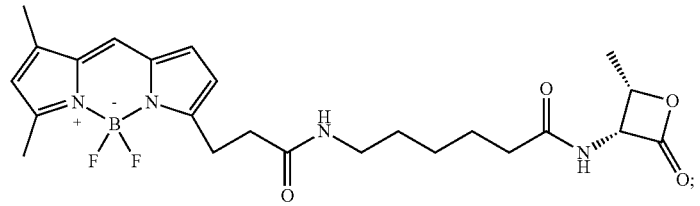
3B
or a salt thereof.

One embodiment of the invention provides a compound of formula I, which is selected from the group consisting of:
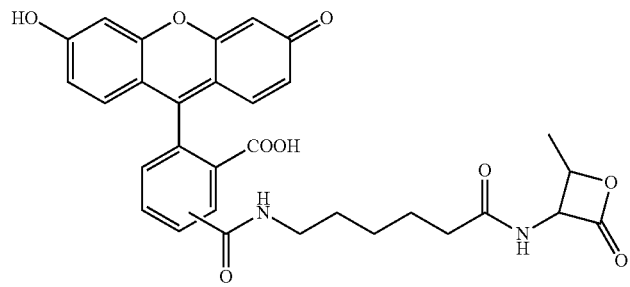
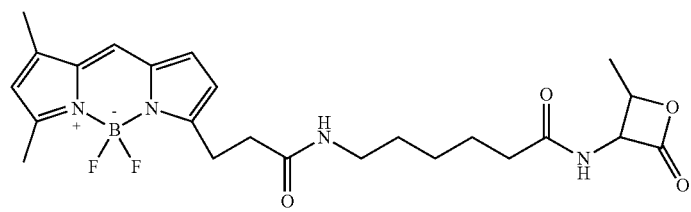
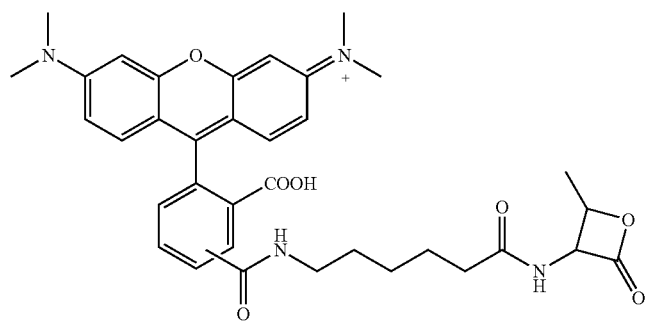
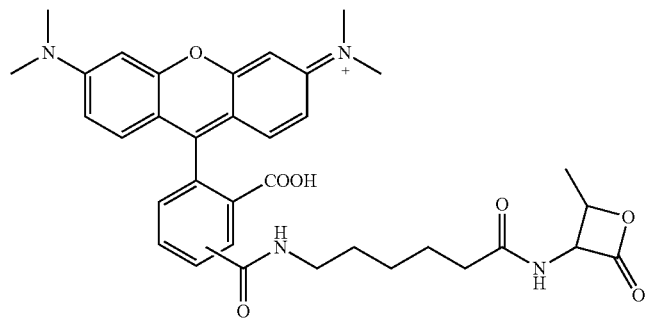
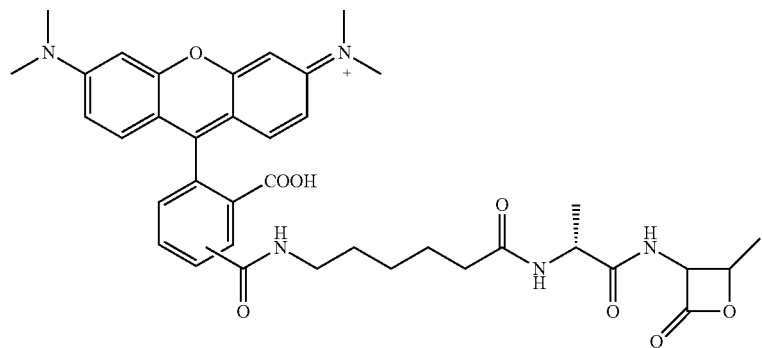

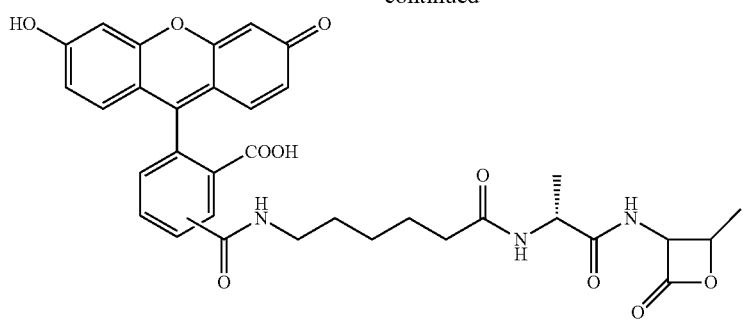
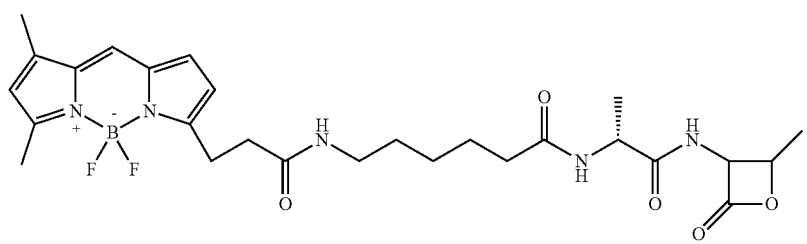
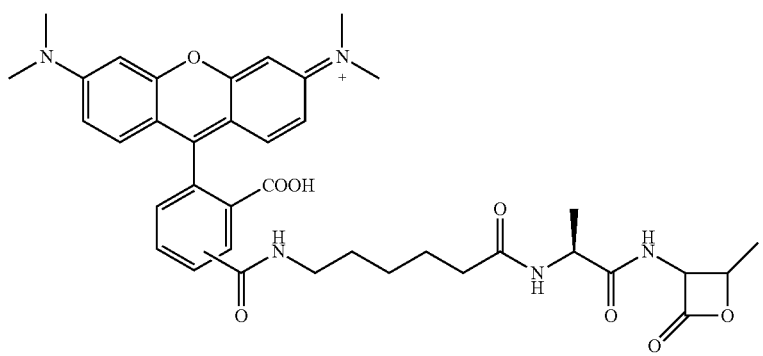
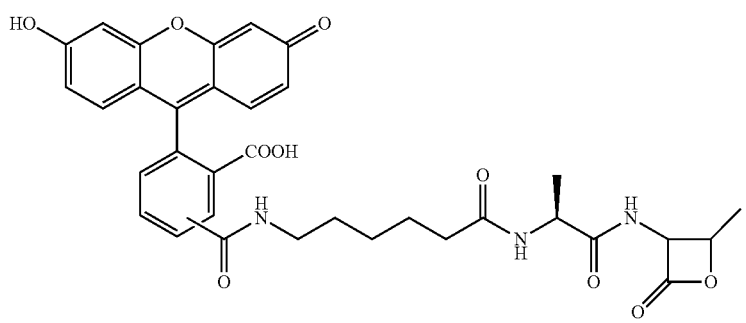
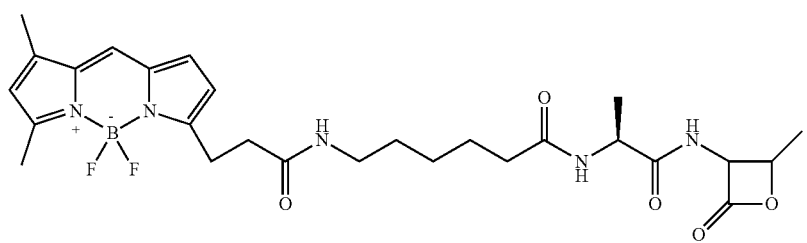

-continued
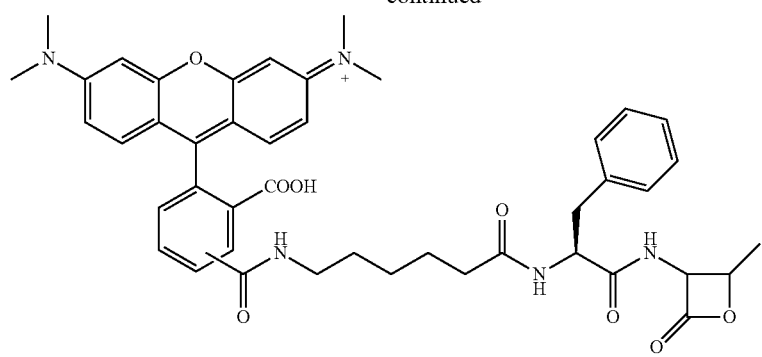
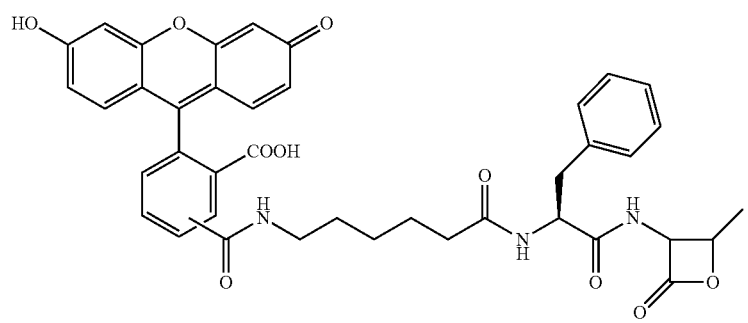
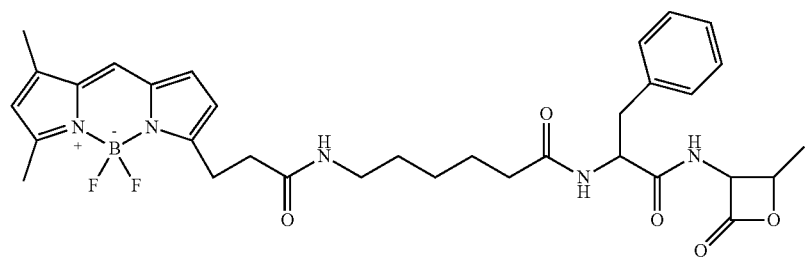
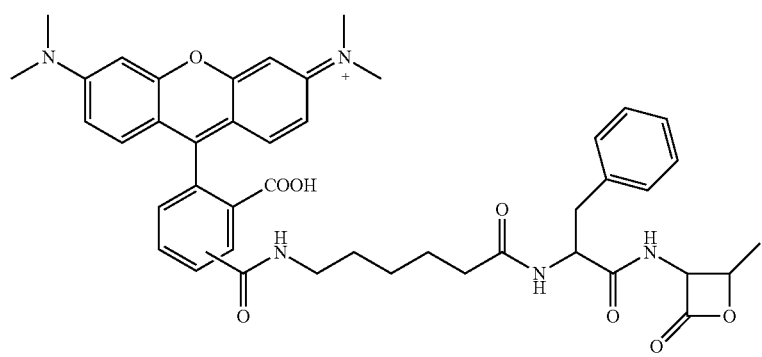
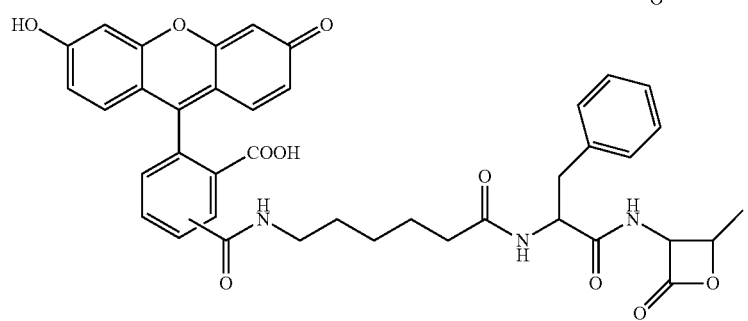

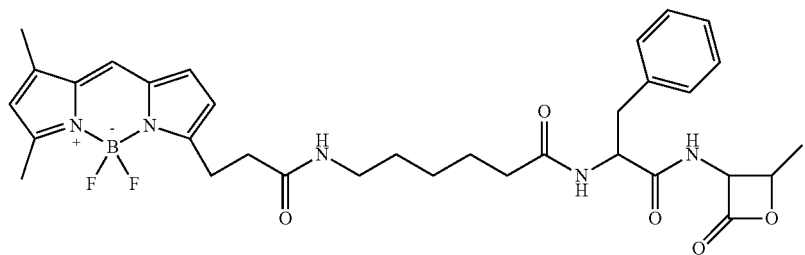
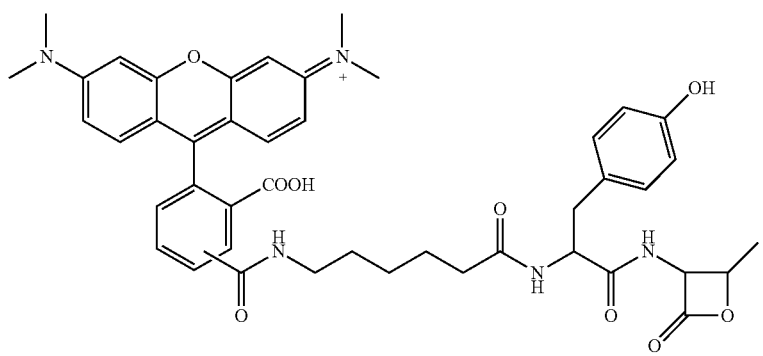
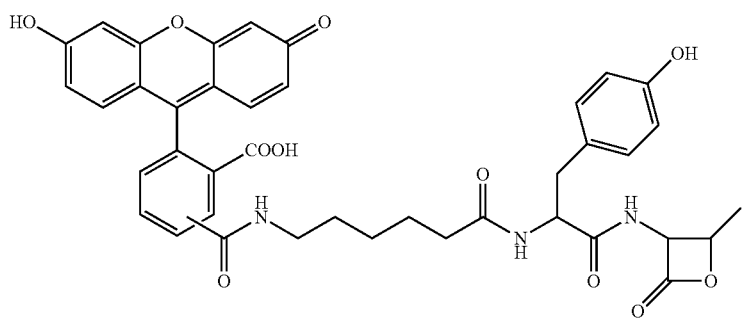
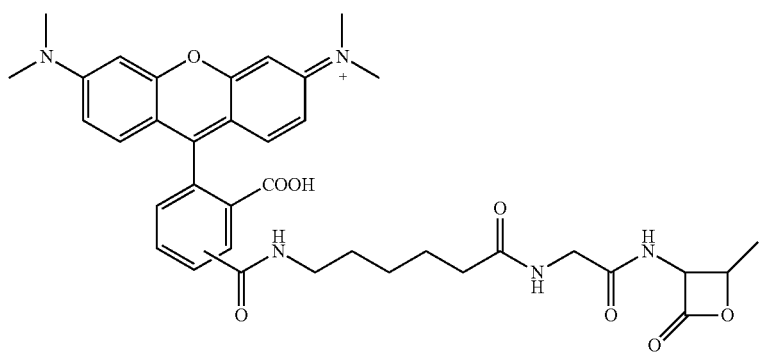
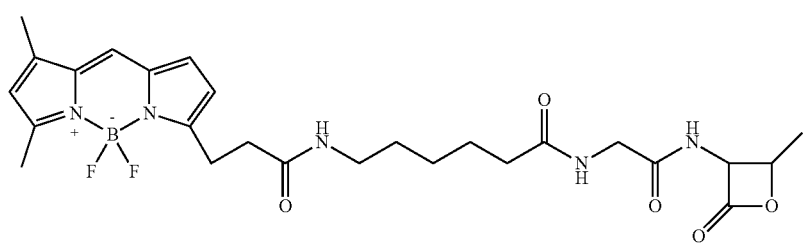

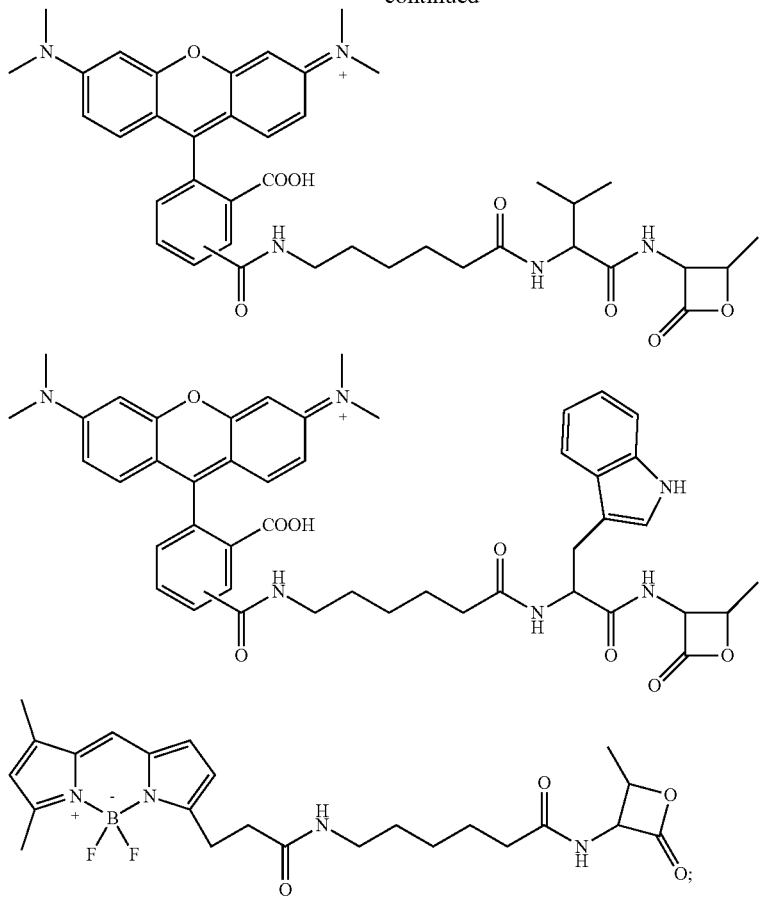

or a salt thereof.

Methods of Use

Certain embodiments of the invention provide a method for labeling one or more penicillin-binding proteins (PBPs), comprising contacting the one or more PBPs with a compound of formula I or a salt thereof to provide one or more labeled PBPs, wherein the compound binds to the one or more PBPs.

Certain embodiments of the invention provide a method for labeling one or more penicillin-binding proteins (PBPs) comprising contacting a cell with a compound of formula I or a salt thereof to provide one or more labeled PBPs, wherein the compound binds to the one or more PBPs.

Certain embodiments of the invention provide a method for labeling one or more penicillin-binding proteins (PBPs) comprising contacting a cell fraction comprising one or more PBPs with a compound of formula I or a salt thereof to provide one or more labeled PBPs, wherein the compound binds to the one or more PBPs.

In one embodiment, more than one PBPs are labeled.

In one embodiment, the labeled PBPs are different.

In one embodiment, the cell fraction is purified cell membranes.

In one embodiment, the one or more PBPs are labeled in vivo.

In one embodiment, the one or more PBPs are labeled in vitro.

In one embodiment, the one or more PBPs are selectively labeled.

In one embodiment, the compound selectively binds to the one or more PBPs.

Certain embodiments of the invention provide a method for labeling one or more penicillin-binding proteins (PBPs) comprising contacting a cell or a cell fraction comprising one or more PBPs with a compound of formula I or a salt thereof and detecting the one or more labeled PBPs, wherein the compound binds to the one or more PBPs.

In one embodiment, the one or more labeled PBPs are detected by SDS-PAGE.

In one embodiment, the one or more labeled PBPs are detected by microscopy.

In one embodiment, the one or more labeled PBPs are detected by flow cytometry.

Certain embodiments of the invention provide a method for labeling one or more penicillin-binding proteins (PBPs) comprising contacting a cell or a cell fraction comprising one or more PBPs with a compound of formula I or a salt thereof, isolating and/or identifying the one or more labeled PBPs, wherein the compound binds to the one or more PBPs.

In one embodiment, the one or more labeled PBPs are identified by liquid chromatography-mass spectrometry (LC-MS).

In one embodiment, the one or more PBPs are selected from the group consisting of class A high molecular weight PBPs, class B high molecular weight PBPs and low molecular weight PBPs.

In one embodiment, the one or more PBPs are selected from the group consisting of PBP1a, PBP1b, PBP2a, PBP2b, PBP2x.

In one embodiment, the one PBP or one of the more PBPs is PBP1b or PBP2x.

In one embodiment, the cell or cell fraction is a gram positive bacteria cell or a gram positive bacteria cell fraction.

In one embodiment, the gram positive bacteria is selected from the group consisting of *Staphylococcus aureus, Staphylococcus epidermidis, Staphylococcus saprophyticus, Streptococcus pyogenes, Streptococcus faecalis, Enterococcusfaecalis, Enterococcus faecium, Bacillus subtilis, Micrococcus luteus, Mycobacterium tuberculosis, Bacillus anthracis, Bacillus cereus, Clostridium difficile, Propionibacterium acnes, Streptococcus mutans, Actinomyces viscosus, Actinomyces naeslundii, Streptococcus sanguis, Streptococcus pneumoniae, Listeria monocytogenes* and *Streptococcus salivarius*.

In one embodiment, the cell or cell fraction is a gram negative bacteria cell or a gram negative bacteria cell fraction.

In one embodiment, the gram negative bacteria is selected from the group consisting of *Escherchia coli, Caulobacter crescentus, Pseudomonas aeruginosa, Agrobacterium tumefaciens, Branhamella catarrhalis, Citrobacter diversus, Enterobacter aerogenes, Enterobacter cloacae, Enterobacter sakazakii, Enterobacter asburiae, Pantoea agglomerans, Klebsiella pneumoniae, Klebsiella oxytoca, Klebsiella rhinoscleromatis, Proteus mirabilis, Salmonella typhimurium, Salmonella enteriditis, Serratia marcescens, Shigella sonnei, Neisseria gonorrhoeae, Acinetobacter baumannii, Acinetobacter calcoaceticus, Acinetobacter lwoffi, Salmonella enteriditis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Borrelia burgdorferi, Neisseria pneumoniaes* and *Haemophilus pneumoniae*.

In one embodiment, the cell or cell fraction is *S. pneumoniae* cell or *S. pneumoniae* cell fraction.

Certain embodiments of the invention provides a method for visualizing the locations of one or more penicillin-binding proteins (PBPs) in a divisional cell comprising:

1) contacting the divisional cell with a compound of formula I or a salt thereof to provide one or more labeled PBPs, wherein the compound binds to the one or more PBPs; and 2) detecting the one or more labeled PBPs by microscopy.

In one embodiment, one PBP is labeled.

In one embodiment, the one labeled PBP is PBP2x.

In one embodiment, the compound is:

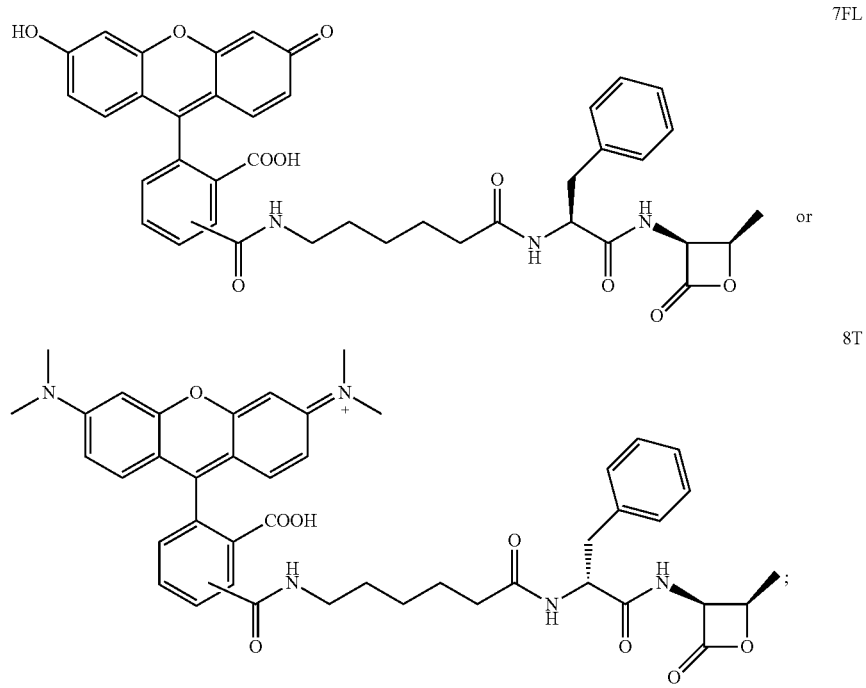

or a salt thereof.

In one embodiment, the divisional cell is wild type *S. pneumoniae* cell.

In one embodiment, the divisional cell is Δpbp1b mutant *S. pneumoniae* cell.

Certain embodiments of the invention provides a method for visualizing the locations of two or more penicillin-binding protein (PBP) in a divisional cell comprising:

1) contacting the divisional cell with a first compound of formula I or a salt thereof, and a second compound of formula I or a salt thereof to provide two or more labeled PBPs, wherein the first compound and the second compound bind to different types of PBPs; and 2) detecting the labeled PBPs by microscopy.

In one embodiment, the labeled PBPs are PBP2x and PBP2b.

Certain embodiments of the invention provide a method for inhibiting one or more PBPs, comprising contacting one or more PBPs with a compound of formula I, or a salt thereof.

Kits

Certain embodiments of the invention provide a kit comprising:

1) one or more compounds of formula I, or salts thereof;
2) instructions for contacting one or more penicillin-binding protein (PBPs) with the one or more compounds sequentially to provide one or more labeled PBPs; and
3) instructions for detecting the labeled PBPs.

Certain embodiments of the invention provide a kit comprising:
1) a compound of formula I, or a salt thereof;
2) instructions for contacting one or more penicillin-binding protein (PBPs) with the compound to provide one or more labeled PBPs; and
3) instructions for detecting the labeled PBPs.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of invention can be prepared using known methods or using procedures analogous to those described in the examples herein. For example, compounds of invention can be prepared as illustrated in the following scheme.

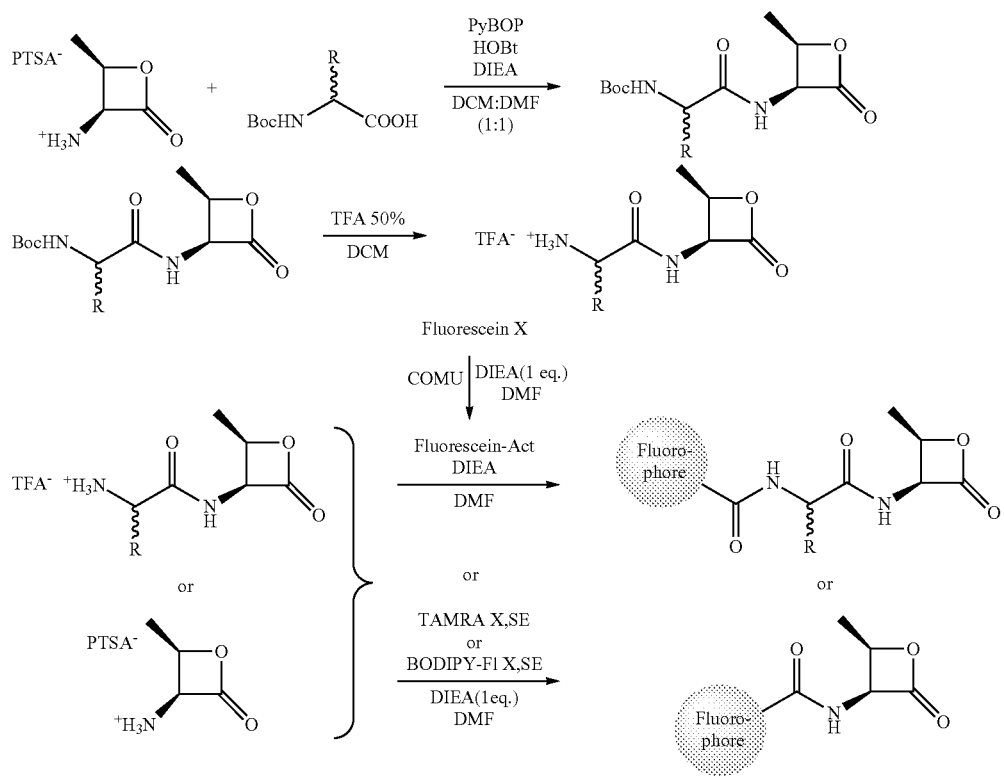

Scheme 1. Synthesis of representative conjugates

Certain embodiments of the invention provide a kit comprising:
1) a compound of formula I, or a salt thereof;
2) instructions for contacting a cell or a cell fraction comprising one or more penicillin-binding protein (PBPs) with the compound to provide one or more labeled PBPs; and
3) instructions for detecting the labeled PBPs.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

The invention will now be illustrated by the following non-limiting Examples.

EXAMPLES

Example 1. Design and Synthesis of Lactone-Based Probes

Figure 2A:
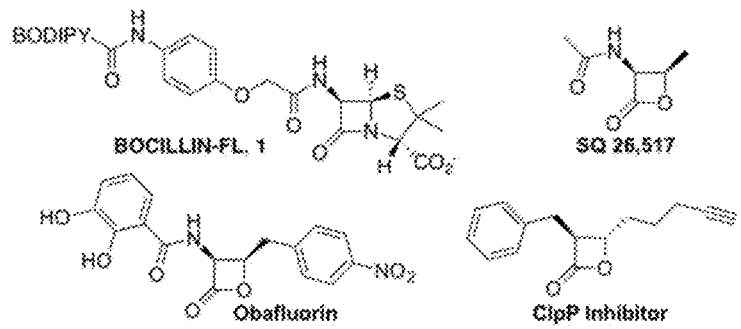
FIGS. 2a-2c show β-lactone-based probe library.
Figure 2B:
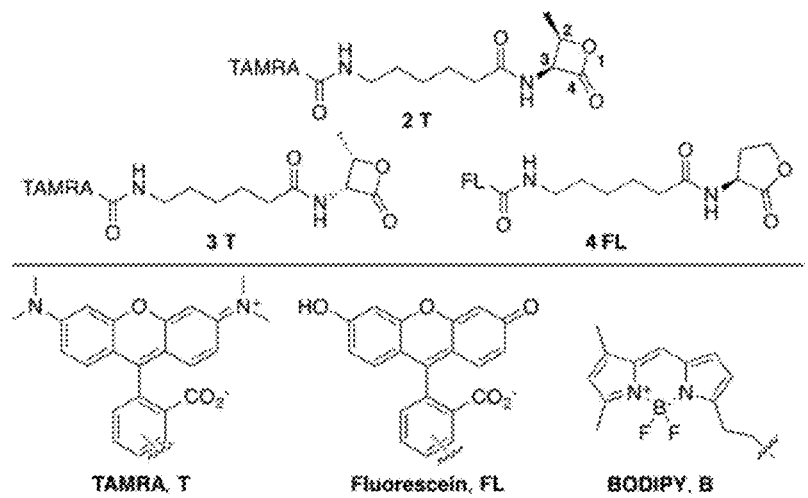
Figure 2C:
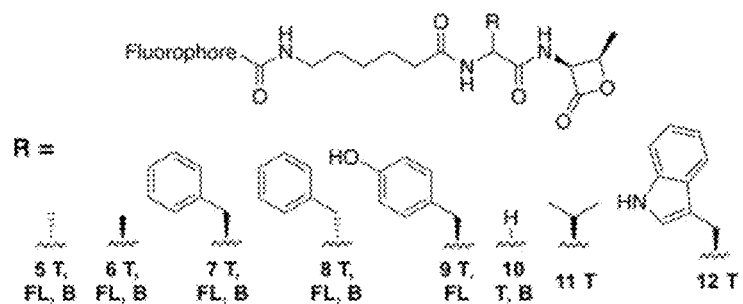

Given the potential of the β-lactone to interact with active site serine residues, including in β-lactamases and a carboxypeptidase (Wells, J. S., et al. (1984) *J. Antibiot.* 37, 802-803; Böttcher, T., et al. (2008) *Angew. Chem. Int. Ed. Engl.* 47, 4600-4603; and Compton, C. L., et al. (2013) *ACS Chem. Biol.* 8, 2669-2677), and the structural similarity of several of these compounds to the β-lactam antibiotics, it is postulated that this scaffold could be optimized to create PBP-selective probes. Inspired by the simple structure of SQ 26,517, lactone-based probes were designed, with an amide group proximal to the electrophilic carbonyl and the ring substituents in the cis conformation, as in β-lactam antibiotics, obafluorin, and SQ 26,517 (FIG. 2a and 2T in FIG. 2b;

lactone ring numbering indicated). For diversification, an amino acid moiety was appended, such as D-Ala to mimic the natural substrate or Phe to mimic the side chain of penicillin, onto this core and a fluorophore to label and visualize PBPs in *S. pneumoniae* (FIG. 2c). Probes were synthesized by adaptation of a known solution phase route (Wang, Z., et al. (2008) *Nat. Chem. Biol.* 4, 557-563). Briefly, threonine was cyclized to form the β-lactone followed by sequential coupling to an amino acid and a fluorophore. The library contained 24 molecules, six that display a lactone directly coupled to a fluorophore [FIG. 2b; 2-4; TAMRA (T), BODIPY-FL (B) or fluorescein (FL)], six compounds with substrate-like sidechains (FIG. 2c; 5 and 6), eight compounds with sidechains to mimic groups found in β-lactam antibiotics (7-9), two functionalized with glycine to assess the significance of the amino acid side chain in protein labeling (10), and two with alternative hydrophobic side chains (L-Val and L-Trp, 11 and 12).

General Materials and Methods

All reactions were carried out in anhydrous solvents under Ar or $N_2$ atmosphere. Hydroxybenzotriazole (HOBt), (1-cyano-2-ethoxy-2-oxoethylidenaminooxy)dimethylamino-morpholino-carbenium hexafluorophosphate (COMU) and benzotriazol-1-yl-oxytripyrrolidinophosphonium hexafluorophosphate (PyBOP) were purchased from Chem-Impex international. BODIPY- and TAMRA-succinimidyl esters were purchased from ThermoFischer Company. Fluorescein was purchased from Sigma-Aldrich Company. All other reagents were purchased from Sigma-Aldrich and used without further purification, unless otherwise noted.

$^1$H and $^{13}$C NMR spectra were recorded on Varian VI-300, and VI-500 spectrometers and are reported in parts per million (δ). The following abbreviations were used to explain the multiplicities: s=singlet, d=doublet, t=triplet, q=quartet, m=multiplet, b=broad. BioTof II electrospray ionization-time-of-flight mass spectrometer with internal standard (Methanolic solution of PEG) or UPLC-ESI-TOF MS instrumentation (Agilent, 6220) were used to obtain accurate mass spectral data. HPLC purification was performed using an Agilent 1200 HPLC using a reverse phase column (Agilent ZORBAX C18, 5 μm, 250×21 mm) detected by diode array detector (200-600 nm). Gradients consisted of 5-100% B (A: $H_2O$, 0.1% formic acid (FA); B: $CH_3CN$, 0.1% FA) over 20-30 minutes.

(1) Lactonization

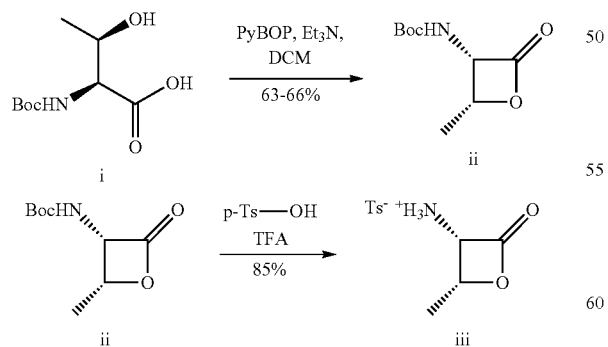

The para-toluenesulfonate (PTSA) salt of (2S,3R)-β-lactone was prepared as described previously (Wang, Z., et al. (2008) *Nat Chem Biol* 4, 557). Briefly, L-Thr-OH (I, 1 eq.), and PyBOP (1.2 eq.) were dissolved in anhydrous DCM at 0° C. and $Et_3N$ (3 eq.) was added dropwise. The reaction mixture was stirred for 30 min at 0° C. and then for 6 h at RT. Solvent was evaporated afterwards and the crude product was purified on silica gel column (ethyl acetate:hexanes 1:6). HRMS (ESI) calcd. For $C_9H_{15}NnaO_4$ [M+Na]+, 20224.0893, found 224.0916. Boc deprotection was performed by adding ii (1 eq.) dropwise to a mixture of p-toluenesulfonic acid (1.05 eq.) and dichloromethane/TFA (~35 eq.) at 0° C. The resulting mixture was stirred for 30 min at 0° C. followed by 30 min at RT. TFA/dichloromethane was subsequently removed in vacuo and residual TFA was co-evaporated with toluene. Iii was precipitated by addition of anhydrous THF followed by anhydrous ether (THF:ether; 1:4) and washed with anhydrous ether (2×) and was used in subsequent coupling reactions without further purification. HRMS (ESI) calcd. For $C_{11}H_{16}NO_5S$ [M+H]+, 274.0744, found 274.0747. The R,S isomer was prepared using the same procedures.

(2) Fluorophore Coupling to β-Lactones

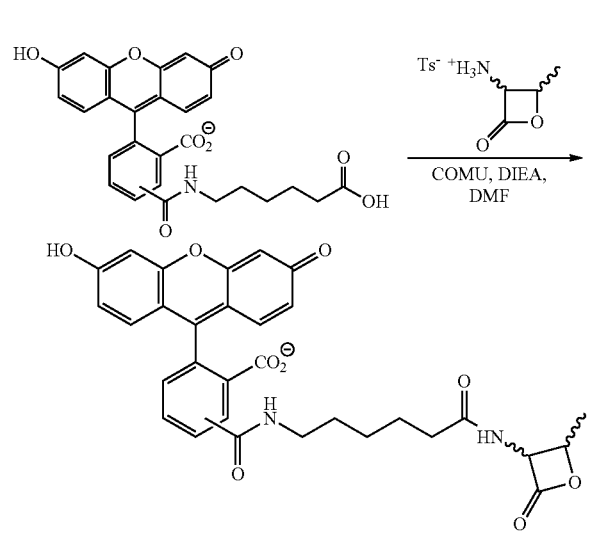

To a solution of 6-[Fluorescein-5(6)-carboxamido] hexanoic acid (0.02 mmol, 10.0 mg), COMU (0.022 mmol, 9.6 mg) in DMF (0.2 ml) at 0° C. DIEA (0.021, 3.7 μL) was added. After stirring for 15 min., premixed lactone (0.02 mmol, 5.5 mg) and DIEA (0.02, 3.5 μL) in DMF (0.1 ml) was added in small portions every 15-30 min to the reaction mixture. Once the reaction was completed (hours to days according to HPLC analysis), the solvent was evaporated and residue was purified by HPLC.

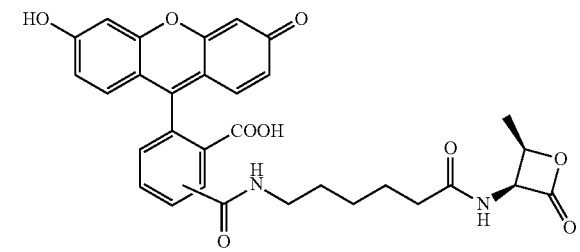

2FL

Reaction time: 1 day. Yield=12%, $^1$H NMR ($CD_3OD$, 500 MHz): δ=1.38 (d, J=6.3 Hz, 3H), 1.61 (m, 6H), 2.33 (t, J=6.3

Hz, 2H), 3.45 (t, J=5.9 Hz, 2H), 4.78-4.83 (m, 1H), 5.56 (d, J=6.0 Hz, 1H), 6.55 (td, J=8.3, 2.5 Hz, 2H), 6.67-6.70 (m, 4H), 7.31 (d, J=8.0 Hz, 1H), 7.61 (s, 1H), 8.08-8.13 (m, 1H), 8.16 (dd, J=8.0, 1.5 Hz, 1H), 8.42 (s, 1H), 8.50 (s, 1H), [M+H]$^+$=573.1873, calc for C$_{31}$H$_{29}$N$_2$O$_9$$^+$ (M+H)$^+$ 573.1868, found 573.1874.

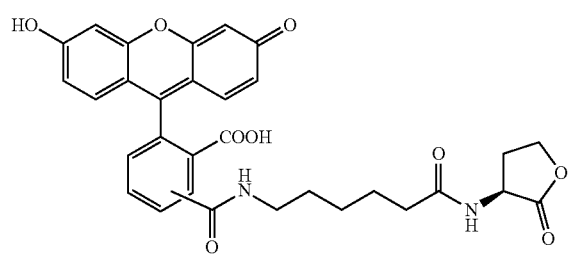

4FL

Yield=6%, $^1$H NMR (500 MHz, DMSO-d6): δ 1.23-1.34 (m, 2H), 1.41-1.47 (m, 2H), 1.50-1.56 (m, 2H), 1.94-2.01 (m, 1H), 2.06-2.16 (m, 2H), 2.32-2.38 (m, 1H), 3.12-3.15 (m, 2H), 4.13-4.20 (m, 1H), 4.26-4.33 (m, 1H), 4.46-4.54 (m, 1H), 5.28-5.31 (m, 1H), 6.49-6.58 (m, 4H), 6.64-6.71 (m, 2H), 7.31-7.36 (m, 1H), 8.17-8.22 (m, 1H), 8.28-8.33 (m, 2H), 8.35-8.44 (m, 1H), 8.78-8.81 (m, 1H); HRMS-ESI: calc for C$_{31}$H$_{29}$N$_2$O$_9$$^+$ (M+H)$^+$ 573.1873, found 573.1862.

(3) Amino Acid Coupling to β-Lactones

Method A:

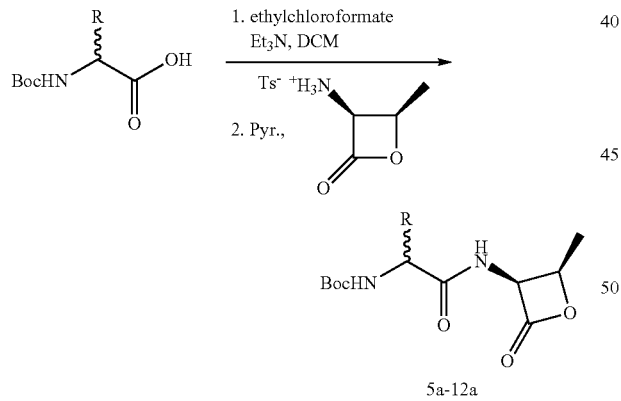

5a-12a

Method B:

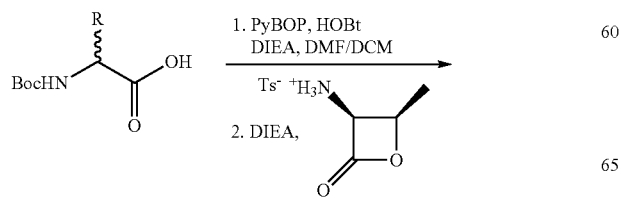

5a-12a

The lactones were coupled to various Boc-protected amino acids using ethylchloroformate (ECF; method A) or PyBOP/HOBt (method B) as described here. In method A, ethyl chloroformate is used as coupling reagent in presence of DIEA as base in anhydrous dichloromethane (DCM). Activation step is performed at −5° C. for 20 minutes, after which, lactone in from of PTSA salt is added plus 2 equivalents of pyridine as base for coupling step. Reaction mixture is stirred for 30 minutes, then warmed to room temperature and stirred overnight. The solvent is then removed and residue is dissolved in ethyl acetate, washed by water and dried over Na$_2$SO$_4$ or CaCl$_2$. Purification is done by silica gel chromatography, using ethyl acetate/hexane or cyclohexane (1:1) as eluting solvent. In Method B, the only variation is that PyBOP is used as the coupling reagent in DMF/DCM (1:1) as reaction solvent.

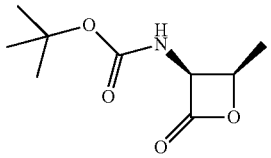

Boc-(2S, 3R)-β-lactone

Yield=63%, $^1$H NMR (300 MHz, CDCl$_3$): δ 1.45 (s, 12H), 4.85 (quin, J=6.2 Hz, 1H), 5.30 (d, J=7.7 Hz, NH), 5.41 (dd, J=8.6, 6.0 Hz, 1H); $^{13}$C NMR (CDCl$_3$): δ=169.3, 154.5, 81.3, 74.9, 60.1, 28.2, 15.0; HRMS-ESI: calc for C$_9$H$_{15}$NnaO$_4$$^+$ (M+Na)$^+$ 224.0893, found 224.0916.

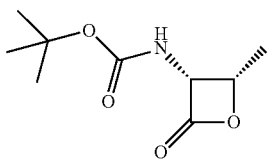

Boc-(2R, 3S)-β-lactone

Yield=66%, $^1$H NMR (300 MHz, CDCl$_3$): δ 1.45 (s, 12H), 4.85 (quin, J=6.2 Hz, 1H), 5.28 (d, J=7.7 Hz, NH), 5.42 (dd, J=8.6, 6.0 Hz, 1H); $^{13}$C NMR (CDCl$_3$): δ=169.3, 154.5, 81.3, 74.9, 60.1, 28.2, 15.0; HRMS-ESI: calc for C$_9$H$_{15}$NnaO$_4$$^+$ (M+Na)$^+$ 224.0893, found 224.0917.

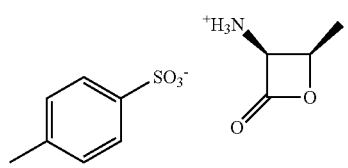

(2S, 3R)-β-lactone

Yield=85%, ¹H NMR (300 MHz, CD₃CN): δ 1.58 (d, J=6.5 Hz, 3H), 2.36 (s, 3H), 4.94 (quin, J=6.5 Hz, 1H), 5.10 (d, J=6.2 Hz, 1H), 7.23 (m, 2H), 7.65 (m, 2H), 8.35 (Br, 3H, NH); ¹³C NMR ((CD₃)₂SO): δ=166.0, 145.9, 138.2, 128.6, 125.9, 72.4, 57.7, 21.25, 14.41; HRMS-ESI: calc for $C_{11}H_{16}NO_5S^+$ (M+H)⁺ 274.0744, found 274.0747.

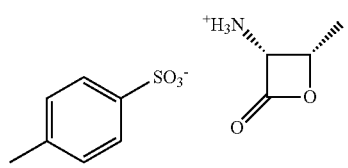

(2R, 3S)-β-lactone

Yield=85%, ¹H NMR (300 MHz, CD₃CN): δ 1.57 (d, J=6.5 Hz, 3H), 2.36 (s, 3H), 4.94 (quin, J=6.5 Hz, 1H), 5.10 (d, J=6.2 Hz, 1H), 7.21 (d, J=8.1 Hz, 2H), 7.65 (d, J=8.1 Hz, 2H), 8.35 (Br, 3H, NH); ¹³C NMR ((CD₃)₂SO): δ=166.0, 145.8, 138.3, 128.6, 125.9, 72.4, 57.7, 21.2, 14.4; HRMS-ESI: calc for $C_{11}H_{16}NO_5S^+$ (M+H)⁺ 274.0744, found 274.0748.

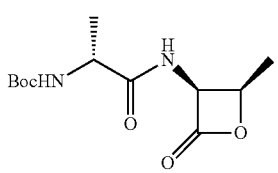 [SMILES: C[C@@H](NC(=O)OC(C)(C)C)C(=O)N[C@@H]1C(=O)O[C@@H]1C]

5a: Method A

Yield=75%, ¹H NMR (500 MHz, CD₃CN): δ 1.29 (d, J=7.0 Hz, 3H), 1.34 (s, 12H), 1.35 (d, J=6.0 Hz, 3H), 4.18 (m, 1H), 4.82 (quin, J=6.0 Hz, 1H), 5.58 (dd, J=8.0, 6.0 Hz, 1H), 8.01 (d, J=8.0 Hz, NH) HRMS-ESI: calc for $C_{12}H_{20}N_2NaO_5^+$ (M+Na)⁺ 295.1264, found 295.1271.

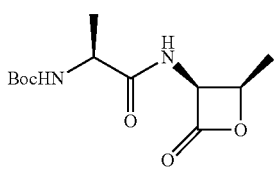 [SMILES: C[C@H](NC(=O)OC(C)(C)C)C(=O)N[C@@H]1C(=O)O[C@@H]1C]

6a: Method A

Yield=80%, ¹H NMR (500 MHz, CDCl₃): δ 1.36 (d, J=7.0 Hz, 3H), 1.38 (d, J=6.5 Hz, 3H), 1.42 (s, 12H), 4.23 (m, 1H), 4.87 (quin, J=6.2 Hz, 1H), 5.27 (d, J=4.5 Hz, NH), 5.59 (dd, J=8.5, 6.0 Hz, 1H), 7.74 (d, J=6.0 Hz, NH); HRMS-ESI: calc for $C_{12}H_{20}N_2NaO_5^+$ (M+Na)⁺ 295.1264, found 295.1269.

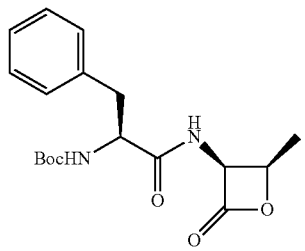 [SMILES: C[C@H]1OC(=O)[C@H]1NC(=O)[C@H](Cc1ccccc1)NC(=O)OC(C)(C)C]

7a: Method B

Yield=60%, ¹H NMR (300 MHz, CD₃CN): δ=1.36 (s, 9H), 1.37 (d, J=6.3 Hz, 3H), 2.87 (dd, J=13.9, 5.1 Hz, 1H), 3.15 (dd, J=13.9, 5.1 Hz, 1H), 4.31 (q, J=6.2 Hz, 1H), 4.84 (quin, J=6.2 Hz, 1H), 5.47 (dd, J=8.4, 6.2 Hz, 1H), 5.56 (d, J=7.3 Hz, 1H), 7.24-7.36 (m, 5H), 7.40 (d, J=8.1, 1H); HRMS-ESI: calc for $C_{18}H_{25}N_2O_5^+$ (M+H)⁺ 349.1758, found 349.1685.

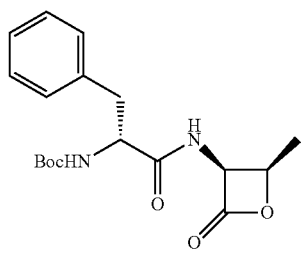 [SMILES: C[C@H]1OC(=O)[C@H]1NC(=O)[C@@H](Cc1ccccc1)NC(=O)OC(C)(C)C]

8a: Method B

Yield=55%, ¹H NMR (300 MHz, CD₃CN): δ=1.27 (d, J=6.3 Hz, 3H), 1.36 (s, 9H), 2.87 (dd, J=13.8, 9.5 Hz, 1H), 3.11 (dd, J=14.1, 5.7 Hz, 1H), 4.29 (dd, J=14.6, 8.5 Hz, 1H), 4.81 (quin, J=6.3 Hz, 1H), 5.47 (dd, J=8.4, 6.3 Hz, 1H), 5.57 (d, J=7.3 Hz, 1H), 7.26-7.33 (m, 5H), 7.42 (d, J=8.1, 1H); HRMS-ESI: calc for $C_{18}H_{25}N_2O_5^+$ (M+H)⁺ 349.1758, found 349.1759.

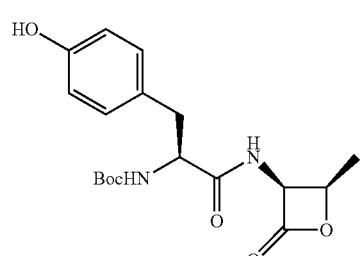

9a: Method A

Compound was obtained by in situ deprotection of benzyl protecting group on the phenolic group after amide bond formation via the following procedure: To a stirred solution of the protected tyrosine derivative, 5 mL of ethanol and 5 ml EtOAc in a 25 mL round-bottom flask charged with an atmospheric H₂ balloon was added 10 mol % Pd-carbon. The reaction mixture was allowed to stir overnight (18 h). Pd-carbon was removed by filtration and the product was concentrated under reduced pressure. Crude materials were purified using flash column chromatography with 1:1 hexanes:ethyl acetate to give the pure product. Yield=37% (two steps), $^1$H NMR (500 MHz, CD₃CN): δ 1.35 (s, 12H), 2.24 (br, 1H), 2.77 (dd, J=13.5, 8.5 Hz, 1H), 3.01 (dd, J=14.0, 5.0 Hz, 1H), 4.20-4.24 (m, 1H), 4.83 (quin, J=6.3 Hz, 1H), 5.43 (t, J=7.0 Hz, 1H), 5.52 (d, J=7.0 Hz, NH), 6.74 (d, J=8.5 Hz, 2H), 6.89 (s, 1H), 7.06 (d, J=8.0 Hz, 2H), 7.43 (d, J=8.5 Hz, NH); HRMS-ESI: calc for $C_{18}H_{25}N_2O_6^+$ (M+H)⁺ 365.1707, found 365.1698.

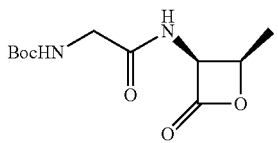 [SMILES: C[C@H]1OC(=O)[C@H]1NC(=O)CNC(=O)OC(C)(C)C]

10a: Method B

Yield=97%, $^1$H NMR (500 MHz, CD₃CN): δ 1.42 (s, 9H), 1.44 (d, J=6.5, 3H), 4.08-4.14 (m, 2H), 4.87 (q, J=6.4 Hz, 1H), 5.45 (dd, J=8.8, 6.0 Hz, 1H), 7.70 (d, J=6.3 Hz, 1H); HRMS-ESI: calc for $C_{11}H_{18}N_2NaO_5^+$ (M+Na)⁺ 281.1108, found 281.1077.

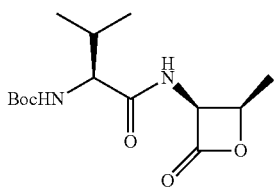 [SMILES: CC(C)[C@H](NC(=O)OC(C)(C)C)C(=O)N[C@@H]1C(=O)O[C@@H]1C]

11a: Method B

Yield=37%, $^1$H NMR (500 MHz, CD₃CN): δ 0.95 (dd, J=10, 6.5 Hz, 6H), 1.41 (s, 9H), 1.43 (d, J=6.5, 3H), 2.08-2.12 (m, 1H), 4.00 (t, J=7.7 Hz, 1H), 4.91 (quin, J=6.2 Hz, 1H), 5.65 (dd, J=8.5, 6.0 Hz, 1H), 6.08 (d, J=8.5 Hz, NH), 8.21 (d, J=7.0 Hz, NH); HRMS-ESI: calc for $C_{14}H_{24}N_2NaO_5^+$ (M+Na)⁺ 323.1577, found 323.1588.

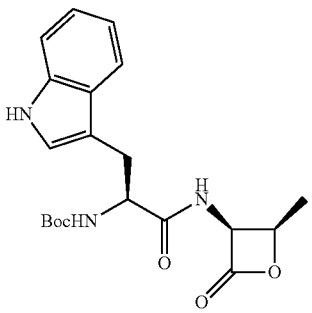 [SMILES: C[C@H]1OC(=O)[C@H]1NC(=O)[C@H](Cc1c[nH]c2ccccc12)NC(=O)OC(C)(C)C]

12a: Method B

Yield=100%, $^1$H NMR (500 MHz, CD₃CN): δ 1.30 (d, J=6.5 Hz, 3H), 1.37 (s, 9H), 3.11 (dd, J=14.3, 8.2 Hz, 1H), 3.27 (dd, J=14.7, 5.2 Hz, 1H), 4.42 (m, 1H), 4.79 (quin, J=6.3 Hz, 1H), 5.48 (t, J=7.5 Hz, 1H), 5.65 (d, J=7.0 Hz, NH), 7.07 (t, J=7.5 Hz, 1H), 7.15 (m, 2H), 7.41 (d, J=8.5 Hz, 1H), 7.61 (t, J=7.5 Hz, 2H), 9.30 (s, 1H); HRMS-ESI: calc for $C_{20}H_{25}NaO_5^+$ (M+Na)⁺ 410.1686, found 410.1645.

(4) Deprotection of Boc Group from Amino Acids Coupled to β-Lactone

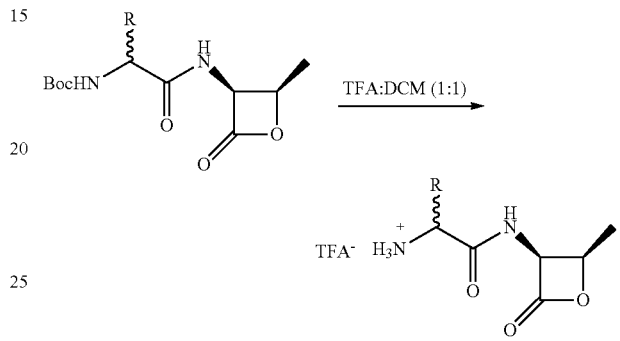

The β-lactone-amino acid conjugate (0.5 mmol) was dissolved in 0.8 ml of DCM and 0.8 ml of trifluoroacetic acid (9.2 mmol) was added to the solution. After completion of the reaction (usually less than 1 hour), solvent was removed in vacuo and the residue co-evaporated with toluene and diethyl ether three times. The crude amine salt was further purified by trituration from EtOAc:Et₂O or pentane.

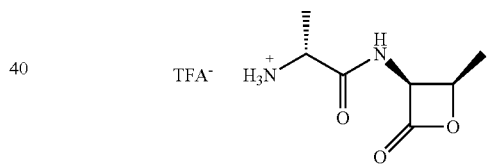

5b

Yield=32%, $^1$H NMR (500 MHz, CD₃CN): δ 1.40 (d, J=6.5 Hz, 3H), 1.50 (d, J=7.0 Hz, 3H), 4.16 (q, J=7.0 Hz, 1H), 4.84-4.89 (m, 1H), 5.50-5.53 (m, 1H), 7.83 (br, 3H), 8.24 (s, 1H); HRMS-ESI: calc for $C_7H_{13}N_2O_3^+$ (M+H)⁺ 173.0921, found 173.0941.

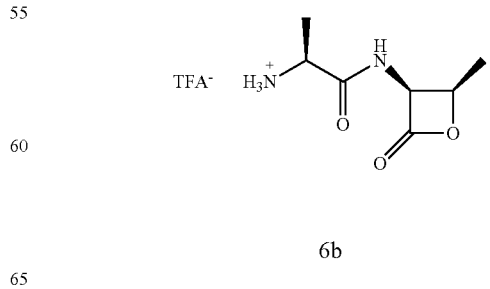

6b

Yield=35%, $^1$H NMR (500 MHz, CD₃CN): δ 1.39 (d, J=6.5 Hz, 3H), 1.51 (d, J=7.0, 3H), 4.13 (q, J=7.2 Hz, 1H), 4.85-4.92 (m, 1H), 5.43-5.49 (m, 1H), 7.57 (br, 3H), 7.98 (s, NH); HRMS-ESI: calc for C$_7$H$_{13}$N$_2$O$_3$+ (M+H)$^+$ 173.0921, found 173.0915.

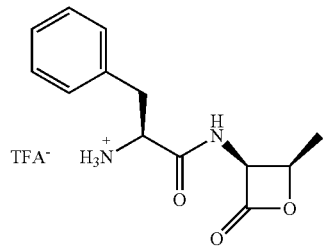 [SMILES: C[C@H]1OC(=O)[C@H]1NC(=O)[C@@H](N)Cc1ccccc1 ; "TFA-"]

7b

Yield=100%, $^1$H NMR (CD$_3$CN, 300 MHz): δ=1.35 (d, J=6.2 Hz, 3H), 2.5 (br, 3H), 3.20 (dd, J=12.8, 7.0 Hz, 2H), 4.27 (t, J=6.8 Hz, 1H), 4.84 (q, J=6.2 Hz, 1H), 5.47 (dd, J=8.4, 6.2 Hz, 1H), 7.29-7.40 (m, 5H), 8.12 (d, J=7.0, 1H); HRMS-ESI: calc for C$_{13}$H$_{17}$N$_2$O$_3$$^+$ (M+H)$^+$ 249.1234, found 249.1252.

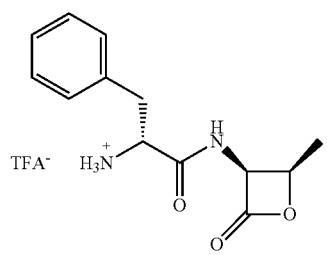 [SMILES: C[C@H]1OC(=O)[C@H]1NC(=O)[C@H](N)Cc1ccccc1 ; "TFA-"]

8b

Yield=100%, $^1$H NMR (CD$_3$CN, 300 MHz): δ=1.19 (d, J=6.6 Hz, 3H), 3.19 (d, J=7.3 Hz, 2H), 4.29 (t, J=7.3 Hz, 1H), 4.81 (quin, J=6.4 Hz, 1H), 5.50 (dd, J=7.4, 6.2 Hz, 1H), 7.30-7.41 (m, 5H), 8.04 (d, J=7.7, 1H); HRMS-ESI: calc for C$_{13}$H$_{17}$N$_2$O$_3$$^+$ (M+H)$^+$ 249.1234, found 249.1252.

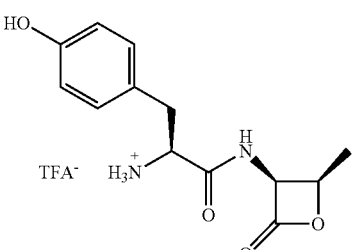

9b

Yield=48%, $^1$H NMR (500 MHz, CD$_3$CN): δ 1.38 (d, J=6.0 Hz, 3H), 2.10 (br, 3H), 3.02-3.08 (m, 1H), 3.14-3.19 (m, 1H), 4.16-4.20 (m, 1H), 4.86 (quin, J=6.0 Hz, 1H), 5.47 (dd, J=8.5, 6.0 Hz, 1H), 6.80 (d, J=8 Hz, 2H), 7.13 (d, J=8.5 Hz, 2H), 7.90-8.05 (br, 1H); HRMS-ESI: calc for C$_{13}$H$_{17}$N$_2$O$_4$$^+$ (M+H)$^+$ 265.1183, found 265.1179.

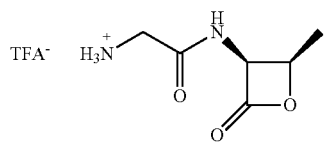

10b

Yield=48%, $^1$H NMR (500 MHz, CD$_3$CN): δ 1.44 (d, J=6.5 Hz, 3H), 2.10 (s, 2H), 4.93 (quin, J=6.5 Hz, 1H), 5.67 (dd, J=8.8, 6.0 Hz, 1H); HRMS-ESI: calc for C$_6$H$_{11}$N$_2$O$_3$$^+$ (M+H)$^+$ 159.0764, found 159.0758.

11b

Yield=96%, $^1$H NMR (500 MHz, CD$_3$CN): δ 1.04 (dd, J=8.5, 7.0 Hz, 3H), 1.40 (d, J=6.0 Hz, 3H), 2.23-2.27 (m, 1H), 3.94 (d, J=5.0 Hz, 1H), 4.88 (quin, J=6.3 Hz, 1H), 5.52 (dd, J=8.5, 6.10 Hz, 1H), 7.67 (br, 3H), 8.09 (d, J=8.5 Hz, 1H); HRMS-ESI: calc for C$_9$H$_{17}$N$_2$O$_3$$^+$ (M+H)$^+$ 201.1234, found 201.1231.

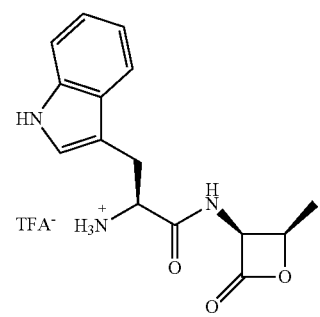 [SMILES: C[C@H]1OC(=O)[C@H]1NC(=O)[C@@H](N)Cc1c[nH]c2ccccc12]

12b

Yield=49.5%, $^1$H NMR (500 MHz, CD$_3$CN): δ 1.36 (d, J=6.5 Hz, 3H), 2.28 (br, 3H), 3.34 (m, 1H), 3.42 (m, 1H), 4.32 (dd, J=7.5, 6.0 Hz, 1H), 4.85 (quin, J=6.2 Hz, 1H), 5.49 (dd, J=8.5, 6.0 Hz, 1H), 7.10 (t, J=7.5 Hz, 1H), 7.18 (t, J=7.5 Hz, 1H), 7.27 (d, J=2.5 Hz, 2H), 7.44 (d, J=8.5 Hz, 1H), 7.68 (d, J=8.0 Hz, 1H), 8.19 (d, J=7.5 Hz, NH), 9.37 (s, 1H); HRMS-ESI: calc for C$_{15}$H$_{18}$N$_3$O$_3$$^+$ (M+H)$^+$ 288.1343, found 288.1324.

(5) Coupling of the Amino Acid-β-Lactone-Conjugates to TAMRA

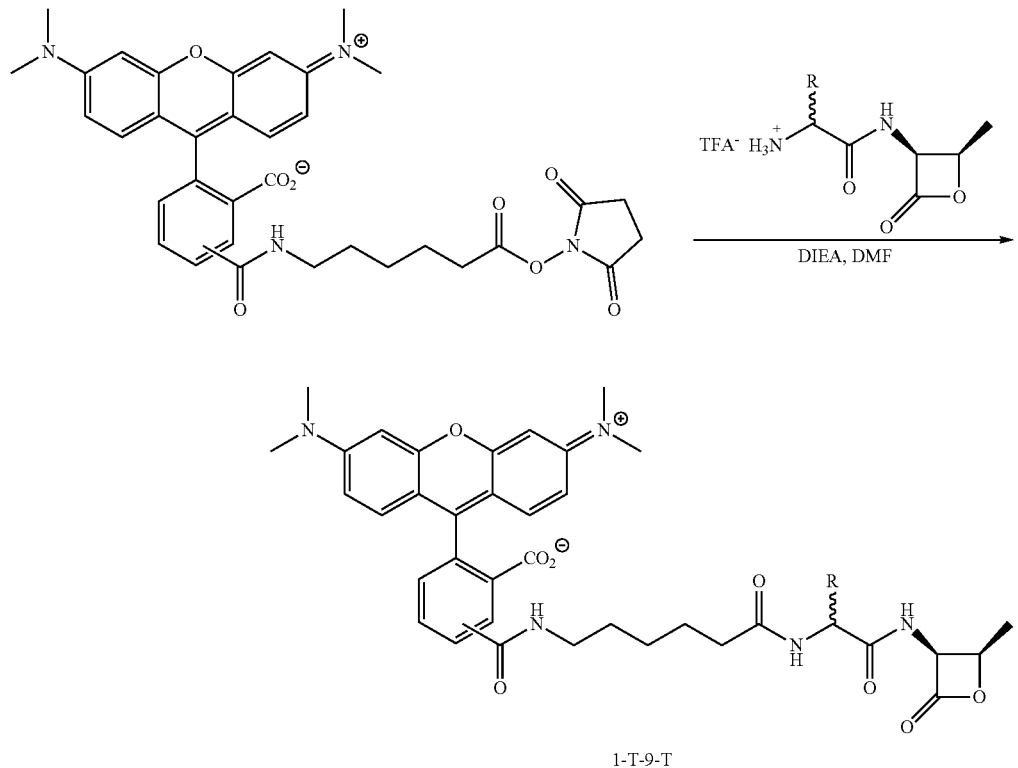

1-T-9-T

To a solution of the β-lactone amine salt (5b-12b) (0.008 mmol) in DMF (0.2 ml) at room temperature was added DIEA (0.009 mmol, 1.55 µL, 1.1 equiv) and fluorophore (0.008 mmol, 1 equiv). Once the reaction was completed (hours to days according to HPLC analysis), the solvent was evaporated and residue was purified by HPLC using the above-described conditions.

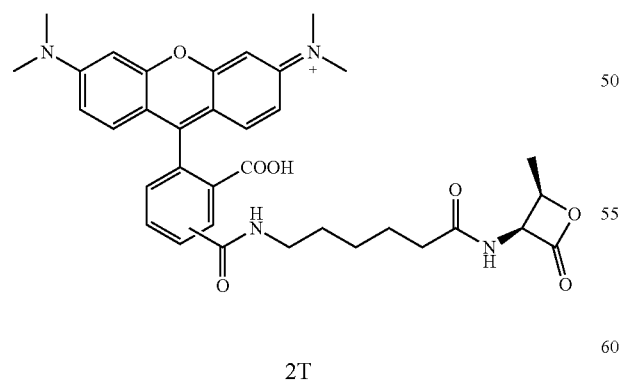

2T

Yield=48%, $^1$H NMR ((CD$_3$)$_2$CO, 500 MHz): δ 1.40 (d, J=6.5 Hz, 3H), 1.40-1.52 (m, 2H), 1.61-1.73 (m, 4H), 2.30 (m, 2H), 3.0 (s, 12H), 3.46-3.53 (m, 2H), 4.88 (quin, J=6.3 Hz, 1H), 5.67 (dd, J=13.5, 6.0 Hz, 1H), 6.50-6.53 (m, 4H), 6.60 (d, J=8.5 Hz, 2H), 7.11 (d, J=8.0 Hz, 1H), 7.31 (d, J=7.5 Hz, 1H), 7.67 (d, J=8.0 Hz, 1H), 8.20 (s, 1H), 8.29 (dt, J=8.0, 1.7 Hz, 1H), 8.42 (d, J=4.5 Hz, 1H), HRMS-ESI: calc for C$_{35}$H$_{39}$N$_4$O$_7^+$ (M+H)$^+$ 627.2813, found 627.2989.

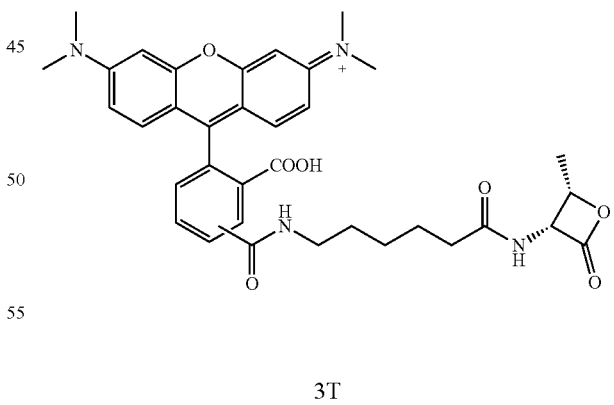

3T

Yield=5%, $^1$H NMR (CD$_3$OD, 500 MHz): δ=1.39 (d, J=6.5 Hz, 3H), 1.45-1.51 (m, 2H), 1.70-1.74 (m, 4H), 2.34 (t, J=7.3 Hz), 3.29 (s, 12H), 3.45 (t, J=7.0 Hz, 2H), 4.85 (quin, J=6.3 Hz, 1H), 5.55 (d, J=6.0 Hz, 1H), 6.94 (d, J=2.0 Hz, 2H), 7.02 (dd, J=9.5, 2.2 Hz, 2H), 7.24 (d, J=9.0 Hz, 2H), 7.38 (d, J=7.5 Hz, 1H), 8.06 (dd, J=7.0, 2.0 Hz, 1H), 8.34 (br, 1H), 8.53 (d, J=1.5 Hz, 1H). HRMS-ESI: calc for C$_{35}$H$_{39}$N$_4$O$_7^+$ (M+H)$^+$ 627.2813, found 627.2810.

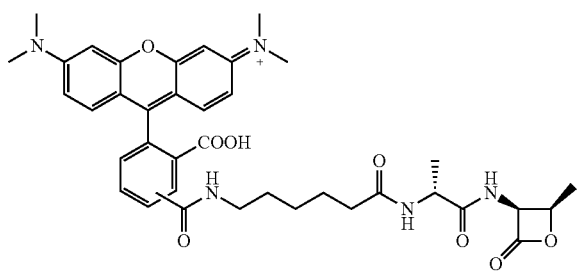

5T

Yield=14%, ¹H NMR (500 MHz, CD₃CN): δ 1.28 (d, J=7.5 Hz, 3H), 1.33 (d, J=6.0 Hz, 3H), 1.38-1.44 (m, 2H), 1.60-1.65 (m, 4H), 2.22 (t, J=7.5 Hz, 2H), 2.99 (s, 12H), 3.38-3.44 (m, 2H), 4.28-4.34 (m, 1H), 4.79 (quin, J=6.3 Hz, 1H), 5.44 (dd, J=8.6, 6.1 Hz, 1H), 6.49-6.54 (m, 4H), 6.61-6.65 (m, 2H), 6.72-6.75 (br, 1H), 7.24 (d, J=8.0 Hz, 1H), 7.38 (br, 1H), 7.49 (d, J =7.5 Hz, 1H), 8.12-8.16 (m, 1H), 8.42 (m, 1H); HRMS-ESI: calc for $C_{38}H_{44}N_5O_8^+$ (M+H)⁺ 698.3184, found 698.2365.

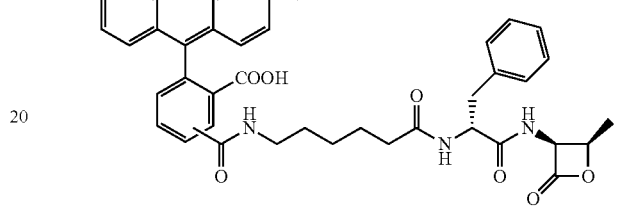

6T

Reaction time of 48 h Yield=16%, ¹H NMR (500 MHz, CD₃CN): δ 1.28 (d, J=7.0 Hz, 3H), 1.35 (d, J=6.5 Hz, 3H), 1.38-1.42 (m, 2H), 1.61-1.65 (m, 4H), 2.21 (t, J=7.3 Hz, 2H), 3.08 (s, 12H), 3.38-3.43 (m, 2H), 4.31-4.34 (m, 1H), 4.80-4.83 (m, 1H), 5.38 (d, J=6.0 Hz, 1H), 6.65-6.73 (m, 4H), 6.85 (d, J=9.1 Hz, 2H), 7.25 (d, J=8.0 Hz, 1H), 8.09 (d, J=7.5 Hz, 1H), 8.42 (s, 1H), HRMS-ESI: calc for $C_{38}H_{44}N_5O_8^+$ (M+H)⁺ 698.3184, found 698.3241.

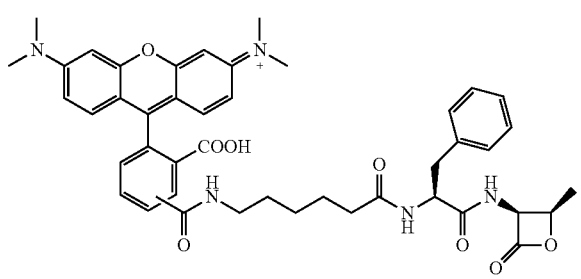

7T

Yield=17%, ¹H NMR (500 MHz, CD₃CN): δ=1.34 (d, J=6.0 Hz, 3H), 1.56 (m, 6H), 2.88 (dd, J=13.5, 5 Hz, 1H), 2.99 (s, 12H), 3.14 (dd, J=13.5, 5.0 Hz, 1H), 3.37 (q, J=6.5 Hz, 2H), 4.65 (m, 1H), 4.80 (quin, J=6.3 Hz, 1H), 5.41 (dd, J=8.5, 6.3 Hz, 1H), 6.49 (d, J=8.5 Hz, 2H), 6.52 (d, J=2.5 Hz, 1H), 6.62 (d, J=9.0 Hz, 2H), 6.72 (d, J=8.5 Hz, NH), 7.20-7.26 (m, 6H), 7.35 (m, 1H), 7.53 (d, J=8.5 Hz, NH), 8.06 (s, 1H), 8.16 (d, J=8.0 Hz, 1H), 8.39 (s, 1H); HRMS-ESI: calc for $C_{44}H_{48}N_5O_8^+$ (M+H)⁺ 774.3497, found 774.3462.

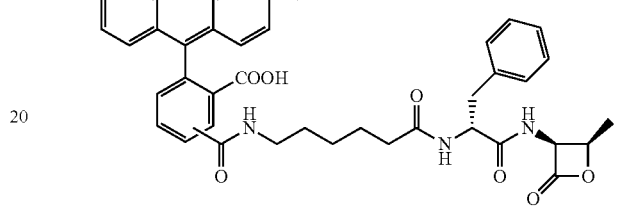

8T

Yield=9%, ¹H NMR (500 MHz, CD₃OD): δ=1.14 (d, J=6.5 Hz, 3H), 1.34 (m, 2H), 1.62 (m, 4H), 2.15 (s, 12H), 2.23 (t, J=7.5 Hz), 2.90 (dd, J=13.5, 8.5 Hz, 1H), 3.1 (dd, J=13.5, 7 Hz, 1H), 3.42 (t, J=7.0 Hz, 2H), 4.71 (m, 1H), 4.76 (m, 1H), 5.47 (d, J=6 Hz, 1H), 6.94 (d, J=2.0 Hz, 2H), 7.02 (m, 2H), 7.21-7.29 (m, 7H), 7.37 (d, J=8.0 Hz, 1H), 8.06 (d, J=8.0 Hz, 1H), 8.53 (s, 1H); HRMS-ESI: calc for $C_{44}H_{48}N_5O_8^+$ (M+H)⁺ 774.3497, found 774.6817.

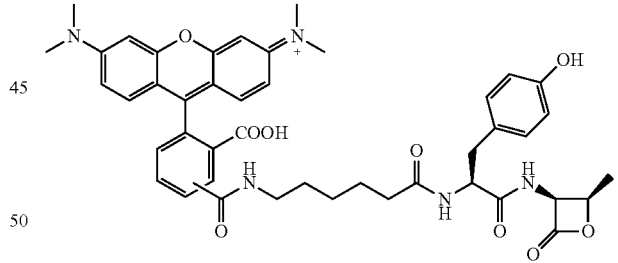

9T

Reaction time of 3 days; Yield=15%, ¹H NMR (500 MHz, CD₃CN): δ 1.35 (d, J=6.5 Hz, 3H), 1.53-1.56 (m, 4H), 1.62-1.65 (m, 2H), 2.99 (s, 12H), 2.73-3.79 (m, 1H), 3.03-3.07 (m, 1H), 3.34-3.38 (m, 2H), 4.57-4.61 (m, 1H), 4.80 (quin, J=6.3 Hz, 1H), 5.40-5.43 (m, 1H), 6.48-6.52 (m, 3H), 6.61-6.66 (m, 2H), 6.72 (d, J=8.5 Hz, 2H), 7.05 (d, J=8.0 Hz, 2H), 7.27 (d, J=8.0 Hz, 1H), 7.42 (br, 1H), 7.50-7.53 (m, 1H), 8.11 (s, 1H), 8.15-8.18 (m, 2H), 8.39 (s, 1H); HRMS-ESI: calc for $C_{44}H_{48}N_5O_9^+$ (M+H)⁺ 790.3447, found 790.3478.

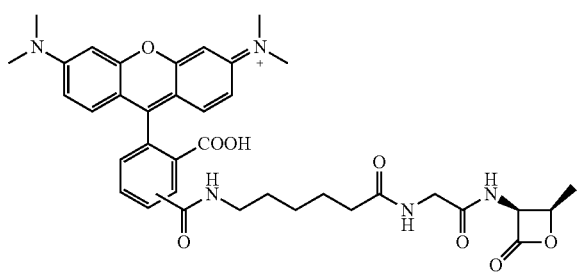

10T

Reaction time of 4 days. Yield=48%, ¹H NMR (500 MHz, CD₃CN): δ 1.35 (d, J=6.5 Hz, 3H), 1.41-1.44 (m, 2H), 1.62-1.66 (m, 4H), 2.25 (t, J=7.3 Hz, 2H), 2.99 (s, 12H), 3.39-3.43 (m, 2H), 3.82 (d, J=5.5 Hz, 2H), 4.81 (quin, J=6.3 Hz, 1H), 5.46 (dd, J=9.0, 6.0 Hz, 1H), 6.49-6.53 (m, 4H), 6.63 (d, J=8.5 Hz, 2H), 6.80 (br, 1H), 7.25 (d, J=8.0 Hz, 1H), 7.34-7.40 (br, 2H), 8.07 (s, 1H), 8.14 (d, J=8.0 Hz, 1H), 8.36 (s, 1H), HRMS-ESI: calc for $C_{37}H_{42}N_5O_8^+$ (M+H)⁺ 684.3028, found 684.3051.

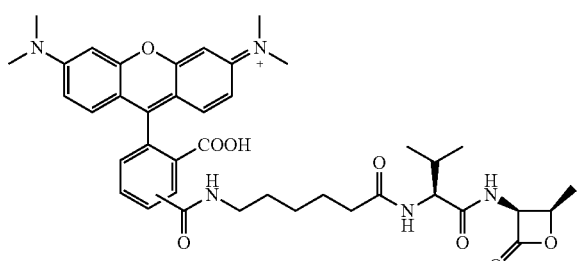

11T

Reaction time of 2 days; Yield=1%, ¹H NMR (500 MHz, DMSO-d₆): δ 0.78-0.84 (m, 6H), 1.31 (d, J=6.0 Hz, 3H), 1.51-1.55 (m, 6H), 1.92-1.97 (m, 1H), 2.19 (m, 2H), 2.92 (s, 12H), 3.35-3.40 (m, 2H), 4.14 (m, 1H), 4.81-85 (m, 1H), 5.49-5.52 (m, 1H), 6.45-6.59 (m, 4H), 6.73 (br, 1H), 7.26 (d, J=8.0 Hz, 1H), 7.92 (d, J=8.5 Hz, 1H), 8.20 (d, J=8.0, 1H), 8.42 (s, 1H), 8.79 (m, 1H), 8.86 (d, J=8.5 Hz, 1H); 9.31 (br, 1H). HRMS-ESI: calc for $C_{40}H_{48}N_5O_8^+$ (M+H)⁺ 726.3497, found 726.3449.

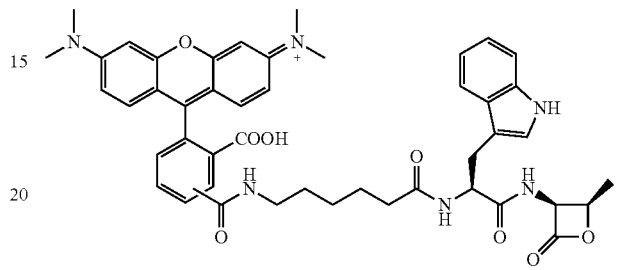

12T

Reaction time of 7 days; Yield=17%, ¹H NMR (500 MHz, DMSO-d₆): δ 1.25 (d, J=7.0 Hz, 3H), 1.41-1.44 (m, 2H), 1.54-1.61 (m, 2H), 1.64-1.69 (m, 2H), 1.97-2.01 (m, 2H), 2.06-2.08 (m, 1H), 2.68 (t, J=7.5 Hz, 2H), 2.92 (s, 12H), 3.45 (m, 2H), 3.31-3.35 (m, 1H), 3.41-3.45 (m, 1H) 4.55 (m, 1H), 4.82 (m, 1H), 5.31 (m, 2H), 5.49 (m, 1H), 6.29 (m, 1H), 6.45-6.51 (m, 4H), 6.61 (m, 1H), 7.11 (m, 1H), 7.19 (m, 1H), 7.28-7.31 (m, 2H), 8.03 (m, 1H), 8.20 (d, J=8.0 Hz, 1H), 8.24 (s, 1H), 8.42 (m, 1H), 8.80 (m, 1H), 8.95 (d, J=8.5 Hz, 1H), 10.81 (s, 1H); HRMS-ESI: calc for $C_{46}H_{49}N_6O_8^+$ (M+H)⁺ 813.3606, found 813.3575.

(6) Coupling of the Amino Acid-β-Lactone-Conjugates to BODIPY

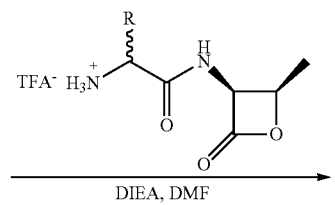

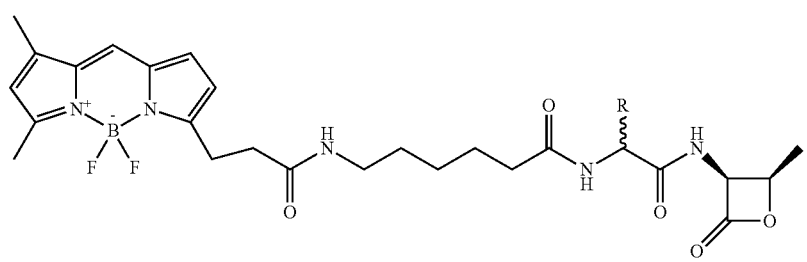

1-B-6-B

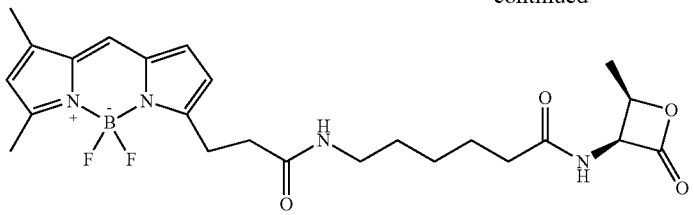

2B

Reaction time of 7 days. Yield=10%, $^1$H NMR (CD$_3$CN, 500 MHz): δ 1.28-1.32 (m, 2H), 1.36 (d, J=6.0 Hz, 3H), 1.45 (quin, J=7.3 Hz, 2H), 1.58 (quin, J=7.5 Hz, 2H), 1.97 (t, J=7.5 Hz, 2H), 2.27 (s, 3H), 2.51 (s, 3H), 3.14 (m, 4H), 4.81 (quin, J=6.3 Hz, 1H), 5.44-5.48 (m, 1H), 6.23 (s, 1H), 6.32 (d, J=4.0 Hz, 1H), 6.41 (br, NH), 7.02 (d, J=4.0 Hz, 1H), 7.09 (br, NH), 7.33 (br, NH), 7.38 (s 1H). HRMS-ESI: calc for C$_{24}$H$_{32}$BF$_2$N$_4$O$_4$$^+$ (M+H)$^+$ 489.2479, found 489.2487.

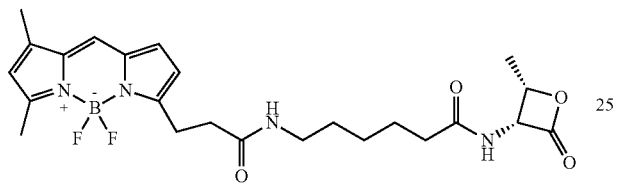

3B ((R,S)Lactone-BODIPY FL)

Reaction time of 44 hrs. Yield=25%, $^1$H NMR (CD$_2$Cl$_2$, 500 MHz): δ=1.28-1.34 (m, 2H), 1.43 (d, J=6.0 Hz, 3H), 1.45-1.50 (m, 2H), 1.60-1.70 (m, 2H), 2.24-2.27 (m, 2H), 2.28 (s, 3H), 2.55 (s, 3H), 2.60 (t, J=7.5 Hz, 2H), 3.22 (m, 4H), 4.87 (quin, J=6.3 Hz), 5.54 (dd, J=8.0, 6.0 Hz, 1H), 5.83 (br, 1H), 6.18 (s, 1H), 6.32 (d, J=4.0 Hz, 1H), 6.58 (d, J=8.0 Hz, 1H), 6.95 (d, J=4.0 Hz, 1H), 7.17 (s, 1H), HRMS-ESI: calc for C$_{24}$H$_{31}$BF$_2$N$_4$O$_4$$^+$ (M+H)$^+$ 489.2414, found 489.2478.

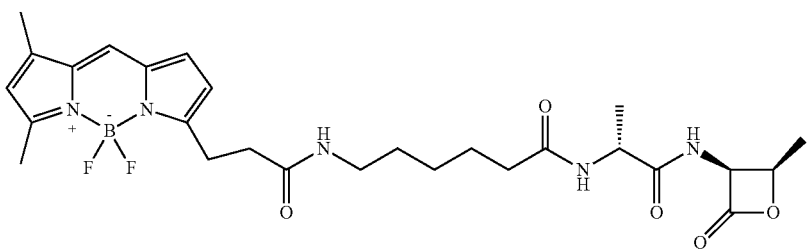

5B

Reaction time of days Yield=11%, $^1$H NMR (500 MHz, CD$_3$CN): δ 1.30 (d, J=7.5 Hz, 3H), 1.29-1.31 (m, 2H) 1.34 (d, J=6.5 Hz, 3H), 1.45 (quin, J=7.5 Hz, 2H), 1.57 (quin, J=7.5 Hz, 2H), 2.16 (t, J=7.5 Hz, 2H), 2.27 (s, 3H), 2.52 (s, 3H), 2.50-2.53 (m, 2H), 3.13 (m, 4H), 4.27 (quin, J=7.0 Hz, 1H), 4.80 (quin., J=6.3 Hz, 1H), 5.43 (dd, J=8.5, 6.2 Hz, 1H), 6.23 (s, 1H), 6.32 (d, J=4.0 Hz, 1H), 6.44 (br, NH), 6.67 (d, J=6.5 Hz, NH), 7.02 (d, J=4.0 Hz, 1H), 7.38 (s, 1H), 7.39-7.42 (br, NH); HRMS-ESI: calc for C$_{27}$H$_{36}$BF$_2$N$_5$NaO$_5$$^+$ (M+Na)$^+$ 582.2670, found 582.2685.

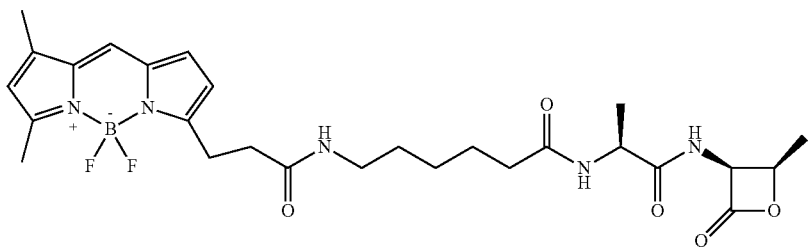

6B

Reaction time of 150 h Yield=22%, $^1$H NMR (500 MHz, CD$_3$CN): δ 1.29 (d, J=7.0 Hz, 3H), 1.28-1.32 (m, 2H) 1.36 (d, J=6.0 Hz, 3H), 1.41-1.476 (quin, J=7.5 Hz, 2H), 1.53-1.58 (quin, J=7.5 Hz, 2H), 2.17-2.21 (m, 2H), 2.27 (s, 3H), 2.51 (s, 3H), 2.50-2.53 (m, 2H), 3.11-3.17 (m, 4H), 4.29 (quin, J=7.0 Hz 1H), 4.80 (quin., J=6.5 Hz, 1H), 5.41 (dd, J=8.5, 6.0 Hz, 1H), 6.23 (s, 1H), 6.32 (d, J=3.5 Hz, 1H), 6.45 (br, NH), 6.68 (br, NH), 7.01 (d, J=3.5 Hz, 1H), 7.39 (s, 1H), 7.43 (br, NH); HRMS-ESI: calc for C$_{27}$H$_{36}$BF$_2$N$_5$NaO$_5^+$ (M+Na)$^+$ 582.2670, found 582.2631.

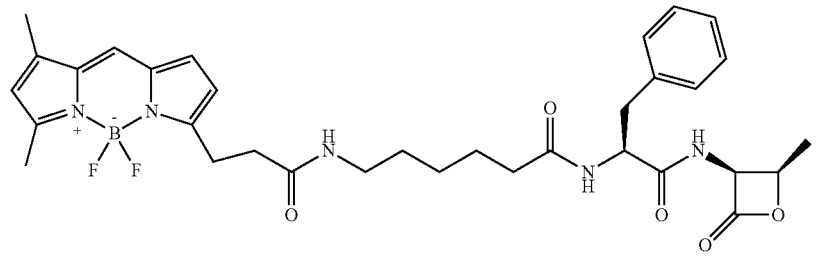

7B

Reaction time of 42 hrs. Yield=32%, $^1$H NMR (acetone-d$_6$, 500 MHz): δ=1.19-1.22 (m, 2H), 1.39 (d, J=6.5 Hz, 3H), 1.42-1.46 (m, 4H), 1.51 (quin, J=7.5 Hz, 2H), 2.30 (s, 3H), 2.52 (s, 3H), 2.57 (t, J=6.5 Hz, 2H), 3.16 (m, 3H), 3.23 (t, J=7.8 Hz, 2H), 4.71 (m, 1H), 4.84 (quin, J=6.3 Hz, 1H), 5.64 (dd, J=8.5, 6.1 Hz, 1H), 6.26 (s, 1H), 6.37 (d, J=4.0 Hz, 1H), 7.05 (d, J=4.0 Hz, 1H), 7.09 (br, NH), 7.19-7.28 (m, 6H), 7.53 (s, 1H), 8.23 (d, J=8.0, NH), HRMS-ESI: calc for C$_{33}$H$_{41}$BF$_2$N$_5$O$_5^+$ (M+H)$^+$ 636.3163, found 636.3029.

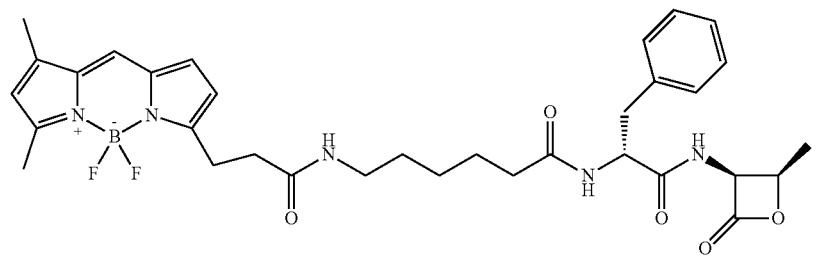

8B

Reaction time of 2 days. Yield=32%, $^1$H NMR (acetone-d$_6$, 500 MHz): δ=1.25 (d, J=6.5 Hz, 3H), 1.42-1.46 (m, 4H), 1.51 (quin, J=7.5 Hz, 2H), 2.30 (s, 3H), 2.52 (s, 3H), 2.57 (t, J=6.5 Hz, 2H), 2.91 (dd, J=14.0, 9.0 Hz), 3.16 (m, 4H), 3.23 (t, J=7.8 Hz, 2H), 4.71 (m, 1H), 4.84 (quin, J=6.3 Hz, 1H), 5.64 (dd, J=8.5, 6.1 Hz, 1H), 6.26 (s, 1H), 6.37 (d, J=4.0 Hz, 1H), 7.05 (d, J=4.0 Hz, 1H), 7.09 (br, NH), 7.19-7.28 (m, 6H), 7.53 (s, 1H), 8.23 (d, J=8.0, NH), HRMS-ESI: calc for C$_{33}$H$_{41}$BF$_2$N$_5$O$_5^+$ (M+H)$^+$ 636.3163, found 636.2720.

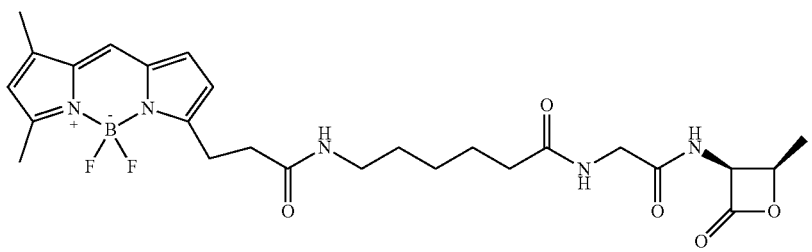

10B

Reaction time of 5 days. Yield=12%, $^1$H NMR (500 MHz, CD$_3$CN): δ 1.30-1.33 (m, 2H), 1.35 (d, J=6.0 Hz, 3H), 1.45 (quin, J=7.3 Hz, 2H), 1.58 (quin, J=7.5 Hz, 2H), 2.19 (t, J=7.5 Hz, 2H), 2.28 (s, 3H), 2.52 (s, 3H), 2.51-2.55 (m, 2H), 3.16 (m, 4H), 3.81 (dd, J=7.5, 6.0 Hz, 2H), 4.80-4.84 (m, 1H), 5.45-5.50 (m, 1H), 6.24 (d, J=6.5 Hz, 1H), 6.34 (s, 1H), 6.44 (br, NH), 6.72 (br, NH), 7.02 (s, 1H), 7.33 (br, NH), 7.39 (d, J=7.5 Hz, 1H) HRMS-ESI: calc for C$_{26}$H$_{34}$BF$_2$N$_5$NaO$_5^+$ (M+Na)$^+$ 568.2513, found 568.2497.

(7) Coupling of Amino Acid-β-Lactone-Conjugates to Fluorescein

5FL

Reaction time of 3 days. Yield=10%, $^1$H NMR (500 MHz, CD$_3$CN): δ 1.29 (d, J=6.7 Hz, 3H), 1.33 (d, J=6.4 Hz, 3H), 1.38-1.45 (m, 2H), 1.50-1.59 (m, 2H), 1.60-1.66 (m, 2H), 2.30 (t, J=7.4 Hz, 2H), 3.26-3.29 (m, 1H), 3.34 (m, 2H), 4.28-4.32 (m, 1H), 4.76 (quin, J=6.0 Hz, 1H), 5.40-5.45 (m, 1H), 6.57 (dt, J=8.6, 3.0 Hz, 2H), 6.65-6.68 (m, 2H), 6.72 (t, J=2.3 Hz, 2H), 7.28 (d, J=8.1 Hz, 1H), 7.38-7.42 (m, 1H), 7.53 (s, 1H), 8.01-8.05 (m, 1H), 8.14 (t, J=1H), 8.35 (d, J=13.0 Hz, 1H).

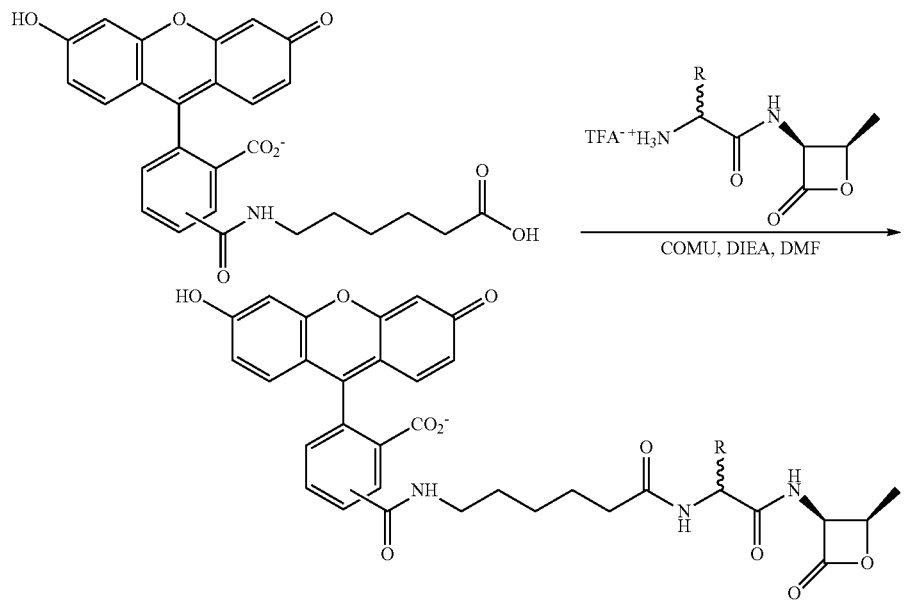

To a solution of 6-[fluorescein-5(6)-carboxamido] hexanoic acid (0.008 mmol, 3.9 mg, 1 equiv), COMU (0.009 mmol, 3.8 mg, 1.1 equiv) in DMF (0.2 ml) at 0° C., DIEA (0.009, 1.55 μL, 1.1 equiv) was added in a dry 1 dram vial. After stirring for 15 min, a pre-mixture of lactone (0.008 mmol, 1 equiv) and DIEA (0.009, 1.55 μL, 1.1 equiv) in DMF (0.1 ml) was added through syringe to the reaction vial. Once the reaction was completed (hours to days according to HPLC analysis), the solvent was evaporated and residue was purified by HPLC.

6FL

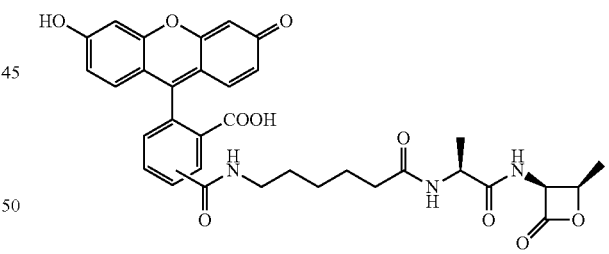

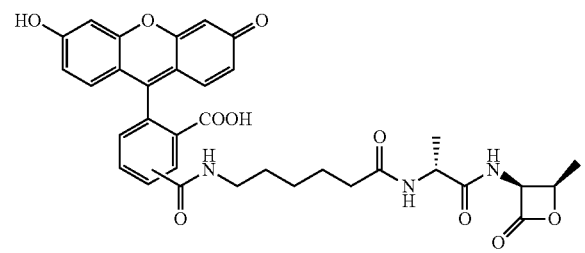

Reaction time of 64 hrs. Yield=10%, $^1$H NMR (500 MHz, DMSO-d$_6$): δ 1.16-1.20 (m, 2H), 1.27 (d, J=7.5 Hz, 3H), 1.30 (d, J=6.5 Hz, 3H), 1.42-1.45 (m, 2H), 1.51-1.54 (m, 2H), 2.21 (t, J=7.3 Hz, 2H), 3.15-3.16 (m, 2H), 4.19-4.26 (m, 1H), 4.82 (quin, J=6.0 Hz, 1H), 5.45-5.55 (m, 1H), 6.54-6.58 (m, 2H), 6.65-6.79 (m, 2H), 7.35 (d, J=8.0 Hz, 1H), 7.65 (s, 1H), 8.06 (d, J=7.5 Hz, 1H), 8.15 (d, J=8.0 Hz, 1H), 8.22 (d, J=8.0, 1H), 8.44 (s, 1H), 8.65-8.67 (m, 1H), 8.79-8.83 (m, 1H), 10.18 (br, 2H); HRMS-ESI: calc for C$_{34}$H$_{34}$N$_3$O$_{10}^+$ (M+H)$^+$ 644.2239, found 644.2196.

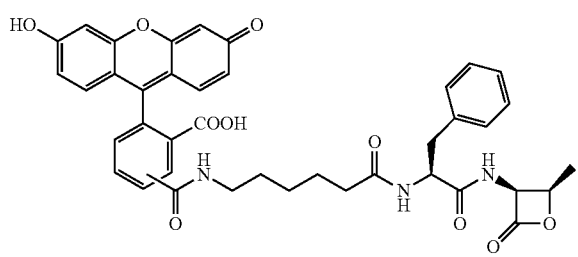

7FL

Reaction time of 22 hrs. Yield=15%, $^1$H NMR (CD$_3$OD, 500 MHz): δ=1.36 (d, J=6.3 Hz, 3H), 1.46-1.51 (m, 2H), 1.54-1.62 (m, 4H), 2.12-2.25 (m, 2H), 2.90 (m, 1H), 3.15 (m, 2H), 3.39 (t, J=7.0 Hz, 2H), 4.63 (m, 2H), 5.45 (dd, J=12.7, 5.9 Hz, 1H), 6.57 (m, 2H), 6.69 (m, 4H), 7.16-7.32 (m, 5H), 7.62 (s, 1H), 8.10 (m, 1H), 8.16 (m, 1H), 8.43 (m, 1H), 8.51 (s, 1H) calc for $C_{40}H_{38}N_3O_{10}^+$ (M+Na)$^+$ 720.2566, found 720.2552.

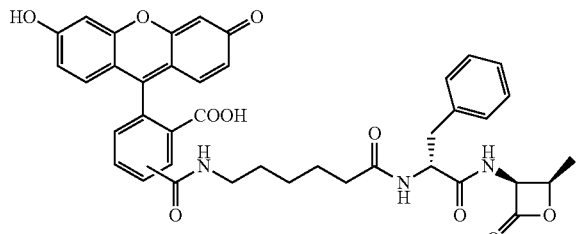

8FL

Reaction time of 1 day. Yield=15%, $^1$H NMR (CD$_3$OD, 500 MHz): δ=1.36 (d, J=6.3 Hz, 3H), 1.46-1.51 (m, 2H), 1.54-1.61 (m, 4H), 2.132 (t, J=7.2 Hz, 1H), 2.20 (t, J=7.2 Hz, 1H), 2.89 (m, 1H), 3.11 (m, 2H), 3.39 (t, J=7.0 Hz, 2H), 4.63 (m, 2H), 5.46 (q, J=6.0 Hz, 1H), 6.61 (t, J=9.5 Hz, 2H), 6.70 (s, 2H), 6.86 (m, 2H), 7.18-7.32 (m, 5H), 7.64 (s, 1H), 8.11 (m, 1H), 8.44 (s, 1H), 8.53 (s, 1H). HRMS-ESI: calc for $C_{40}H_{38}N_3O_{10}^+$ (M+Na)$^+$ 720.2566, found 720.2559.

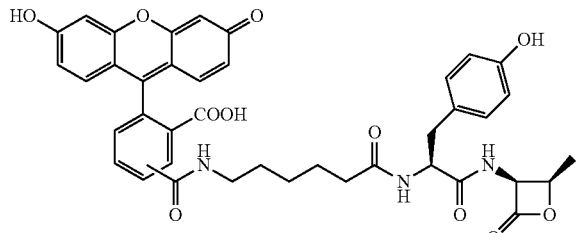

9FL

Reaction time of 1 day; Yield=6%, $^1$H NMR (500 MHz, DMSO-d$_6$): δ 1.20-1.30 (m, 9H), 1.97-2.05 (m, 2H), 2.14-2.19 (m, 2H), 3.03-3.13 (m, 2H), 3.53-3.61 (m, 2H) 4.20-4.27 (m, 1H), 4.80 (q, J=7.0 Hz, 1H), 5.34 (m, 1H) 6.50-6.68 (m, 6H), 6.98-7.02 (m, 2H), 7.34 (d, J=8.5 Hz, 1H), 7.65 (s, 1H), 8.01-8.22 (m, 3H), 8.43 (s, 1H), 8.64 (m, 1H), 8.70-8.79 (m, 1H), 8.86-8.91 (m, 1H), 9.16 (br, 1H), 10.15 (br, 2H); HRMS-ESI: calc for $C_{42}H_{39}N_4O_{10}^+$ (M+H)$^+$ 759.2661, found 644.2631.

Example 2. Biological Evaluation—PBP Labeling with β-Lactone Probes

Figure 3A:
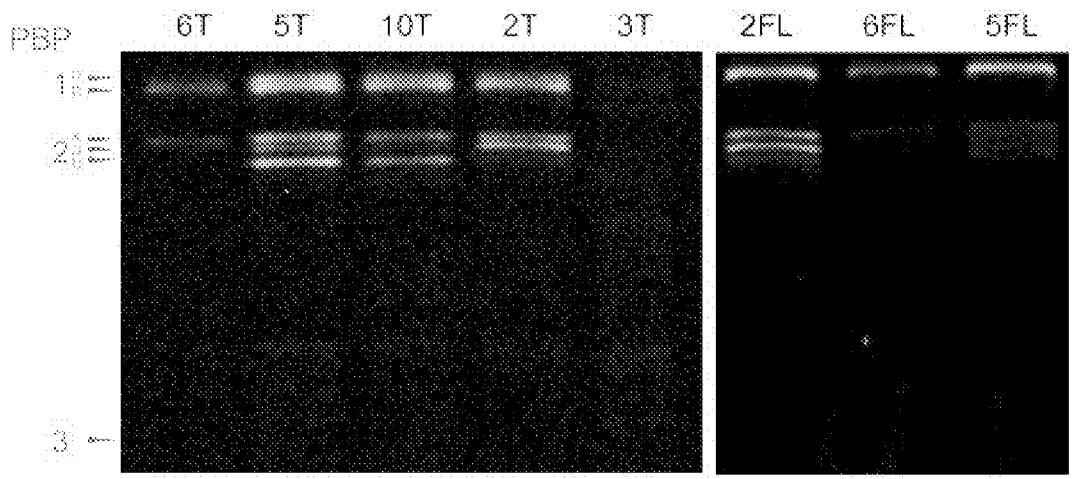
FIGS. 3a-3b show gel-based analysis of probes to examine ring geometry (2 and 3) and side chains that act as substrate mimetics (5 and 6).
Figure 3B:
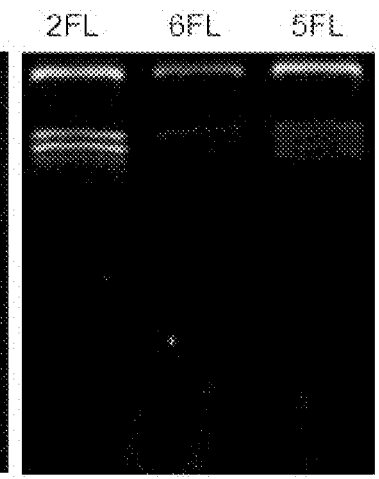

First, the importance of the cis oriented functionalities on the β-lactone was examined with compounds (2R, 3S)-β-lactone (2) and (2S, 3R)-β-lactone (3; FIG. 2b). The stereochemistry of the substituents on the lactone ring is crucial for productive labeling. While the (2R, 3S)-β-lactone (2FL and 2T) labeled most PBPs (PBP1a, PBP1b, PBP2x and PBP2a), the (2S, 3R)-β-lactone isomer labeled nothing (3T; FIG. 3a and FIG. 3b). This suggests that β-lactones that closely mimic the geometry of β-lactam antibiotics are also active-site directed. Consistent with this, lactone labeling of the PBPs is competitive with penicillin and the resulting acylated protein complex is stable as it is not displaced by incubation with Boc-FL. These results are especially intriguing given that the probes lack an ionizable group to mimic the C-terminal D-Ala residue carboxylate in the native stem peptide, which is found in all clinically relevant β-lactam antibiotics (Konaklieva, M. I. (2014) Antibiotics 3, 128-142). In addition, the selectivity of this simple scaffold for the PBPs is remarkable given the relatively large number of protein classes tagged in previous studies with β-lactone-containing molecules (Böttcher, T., et al. (2008) J. Am. Chem. Soc. 130, 14400-14401; Böttcher, T., et al. (2008) Angew. Chem. Int. Ed. Engl. 47, 4600-4603; Zeiler, E., et al. (2011) Angew. Chem. Int. Ed. Engl. 50, 11001-11004; and Wang, Z., et al. (2008) Nat. Chem. Biol. 4, 557-563).

To further confirm that the four-membered lactone ring (β-lactone) is crucial for PBP-specific labeling, several five-membered lactone scaffolds (δ-lactone) were assessed. δ-Lactone-FL (4FL) was found not to label any proteins in S. pneumoniae (data not shown). Several N-acyl homoserine lactones, δ-lactones used by bacteria in quorum sensing (Galloway, W. R. J. D., et al. (2011) Chem. Rev. 111, 28-67; and Welsh, M. A., et al. (2016) FEMS Microbiol. Rev. 40, 774-794) were also tested for PBP inhibition and found them to be inactive. This difference is likely due to a combination of both recognition events in the PBP active site and the higher ring strain energy of β-lactones in comparison to δ-lactones (23 kcal mol$^{-1}$ vs. 8 kcal mol$^{-1}$; β-lactam is 28 kcal mol$^{-1}$) (Kim, D. H., et al. (2002) Bioorg. Med. Chem. 10, 2553-2560; Houk, K. N., et al. (2008) J. Org. Chem. 73, 2674-2678; and Kishore, N., et al. (1994) Biophys. Chem. 49, 163-174). These results, in addition to the finding that when cells were treated with the β-lactones before they were conjugated to a fluorophore, none of these precursors inhibited the PBPs, indicate that the β-lactone scaffold is not labeling proteins nonspecifically. Assessment of the structurally-related compound, SQ 26,517, indicated that it is a very weak inhibitor of PBP2a, again indicating that sufficient binding interactions are essential for facile PBP targeting.

Figure 4:
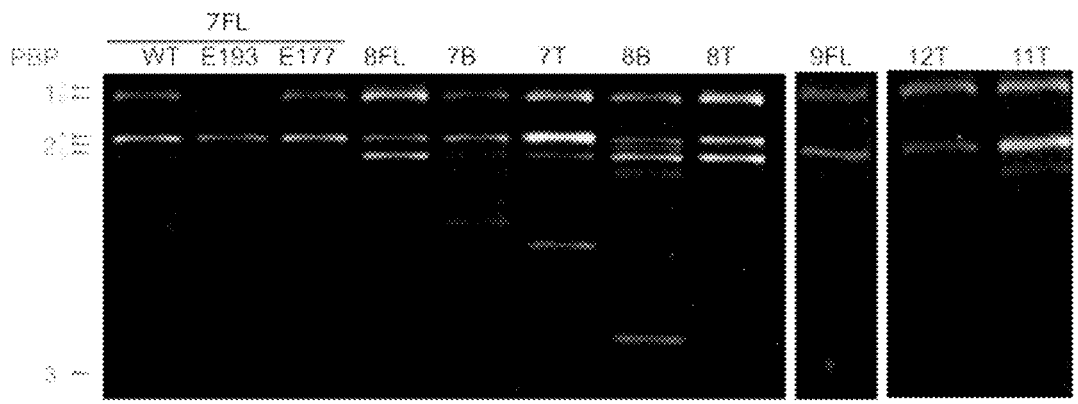
FIG. 4 shows gel-based analysis of probes containing side chains to mimic the functionalities found in β-lactam antibiotics. L-Phe-(2S, 3R)-β-lactone (7T, B and FL), D-Phe-(2S, 3R)-β-lactone (8T, B and FL) were assessed at 5 μg/ml. Probe labeling was generally identical between FL and T variants, while BODIPY often increased the number of proteins labeled, including non-PBPs (see 8B). L-Phe-(2S, 3R)-β-lactone-based probes (7) showed promise for assessment of PBP2x by use of the Δpbp1b strain. Gel-based analysis of S. pneumoniae wild-type (IU1945), E177 (Δpbp1a) and E193 (Δpbp1b) strains was performed to confirm specific labeling of PBP2x in the mutant strain. Additional hydrophobic side chains were examined including L-Tyr (9FL), L-Val (11T) and L-Trp (12T), all of which labeled PBP1b and PBP2x.
Figure 7:
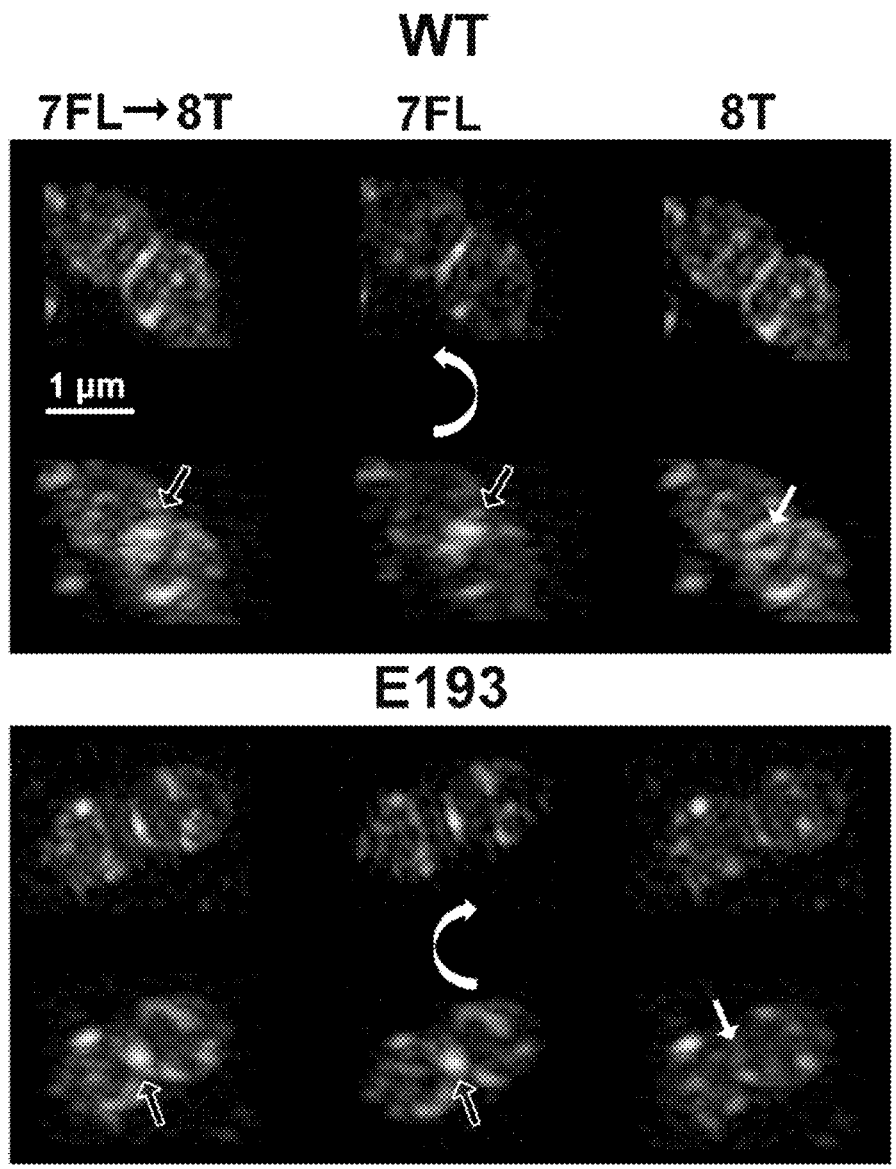
FIG. 7 shows labeling with 7FL followed by 8T reveals distinct PBP localization patterns. Cultures of wild-type and E193 cells were grown, labeled with 7FL, washed, labeled with 8T, and imaged as described in *Experimental procedures*. Each image set is two rows of images of the same cell, with the bottom row rotated relative to the top row around the indicated axis. In both strains, 8T labeling is excluded from the septum and restricted to peripheral rings when the cells are labeled first with 7FL. Empty arrows highlight central septal labeling, and solid arrows highlight the exclusion of 8T labeling from the center of the division site. These images are representative of >40 mid to late division cells for each condition from two biological replicates.

Probes designed to resemble the stem peptide were assessed. The molecule containing a D-Ala residue and TAMRA (5T) labeled all HMW PBPs, making it more general than compounds without a side chain (Gly derivative, 10T; PBP1a, PBP1b, PBP2x, PBP2b) or those that lack an amino acid diversity element when utilized at the same concentration (FIG. 3a; 2FL and 2T labeled all HMW PBPs at four-fold higher concentration, 20 µg/ml). This may indicate that a similar binding pocket is accessed by D-Ala in the probe and the natural substrate. However, the fluorescein-functionalized probe (5FL) labeled only PBP1b and PBP2x, suggesting that the fluorophore component can also influence protein labeling (FIG. 3b). Indeed, molecules functionalized with BODIPY-FL often yielded substantially different tagging profiles, even labeling non-PBP targets (FIG. 4, 7B and 8B). Importantly, all compounds generated with TAMRA or fluorescein read-out groups gave identical labeling profiles, with the exception of the L-Phe-functionalized derivatives, which tagged PBP1b and PBP2x when displaying a fluorescein and labeled PBP1b, PBP2x, PBP2b and a non-PBP when appended to TAMRA.

Evaluation of probes displaying hydrophobic side chains, several of which are found in β-lactam antibiotics, such as a phenyl in penicillin G, or hydroxyphenyl displayed on amoxicillin, was next performed. Resolution of the tagging of PBP1a and PBP1b, which migrate very closely in the gels, was accomplished by utilizing Δpbp1a and Δpbp1b strains (E177 and E193, respectively). The D-Phe derivative (8FL) tagged PBP1b, PBP2x and PBP2b, while the L-Phe and L-Tyr FL derivatives (7FL and 9FL) labeled only PBP1b and PBP2x (FIG. 4). Indeed, a large number of probes, including additional hydrophobic side chains, co-labeled PBP1b and PBP2x (L-Ala: 6T and 6FL, D-Ala: 5FL, L-Phe: 7FL, L-Tyr: 9FL, L-Val: 11T, L-Trp: 12T). Overall, PBP1b is labeled by all tested β-lactone probes and several compounds co-selectively labeled PBP1b and PBP2x. This may indicate that these proteins are tolerant of side chains with diverse size and configuration. PBP2x is a common target of the β-lactams and is often co-inhibited with PBP3 (Kocaoglu, O., et al. (2015) Antimicrob. Agents Chemother. 59, 3548-3555), which was not labeled by any of the β-lactone probes. In contrast, PBP1b is among the less frequently targeted PBPs by these antibiotics, indicating that the probe library may be accessing a different region of binding space within the PBP active sites. PBP2b, which is the least inhibited PBP with conventional β-lactam antibiotics, was labeled by three probe scaffolds (5T, 5FL 8T, 8FL, 10T). PBP1a and PBP2a labeling was only observed with probes displaying a small side chain (PBP1a: 2FL, 2T, 5FL, 5T, 5B, 10T and 10B; PBP2a: 2T, 2FL, 5T and 5FL).

Figure 8:
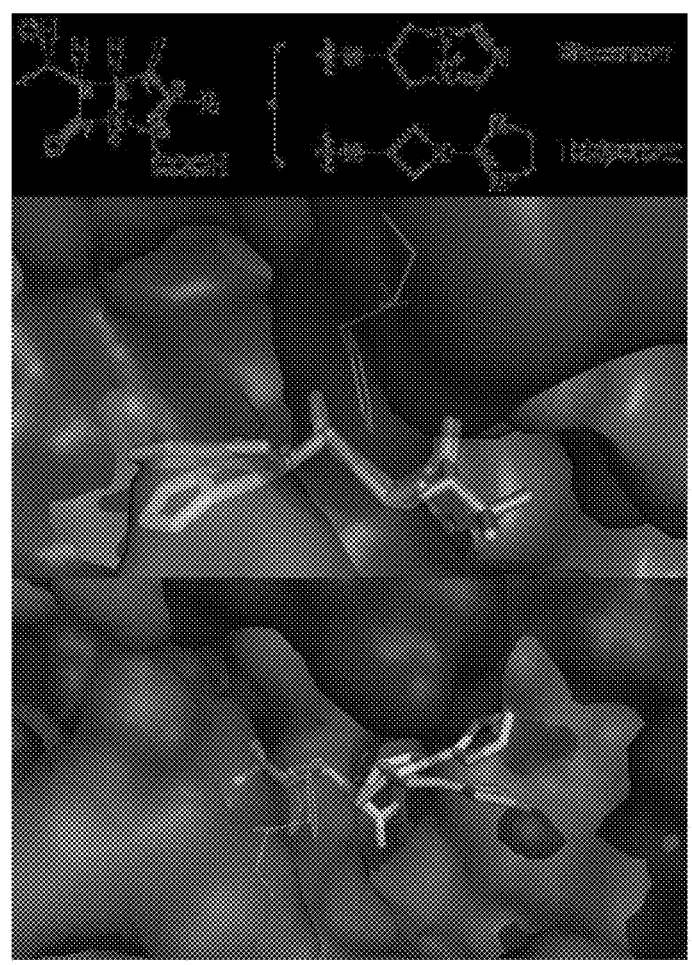
FIG. 8 shows superposition of the active site of PBP2x and PBP1a co-crystallized penem drugs. Top: chemical structures of tebipenem and biapenem; the carbapenem core is numbered. Middle: Crystal structures of PBP2x and PBP1a each separately complexed with biapenem are overlaid. Presence of bulky side chains, such as Phe577 in the active site of PBP1a, blocks the entrance. Bottom: Crystal structures of PBP2x and PBP1a each separately complexed with tebipenem are overlaid. Drugsite was used for superposition of structures.

To further examine the differences in the PBPs that may be responsible for the disparate labeling response, the structures of PBP2x and PBP1a were compared, the former being labeled by many probes and the later tagged by only a small subset. Both proteins have been co-crystallized with tebipenem or biapenem and we overlaid these structures for comparison of their active sites (FIG. 8). In PBP1a, a bulky residue can be found near C6 of the lactam core structure (i.e., F577), a position that we anticipate may be occupied by the diversity element in our probes. The presence of this large group may explain the requirement of a small side chain on the probes for productive binding. In contact, PBP2x has an open cleft at this position, which is consistent with the observed tagging by a larger diversity of probes.

Although PBP3 is inhibited by the vast majority β-lactam antibiotics (Kocaoglu, O., et al. (2015) Antimicrob. Agents Chemother. 59, 3548-3555), none of the β-lactone probes labeled this protein, the only LMW PBP in S. pneumoniae. It has been postulated that the facile inhibition of PBP3 can be partially attributed to the high catalytic efficiency of this D,D-carboxy endopeptidase as determined by the hydrolysis of the pseudo substrate N-benzoyl-D-alanylmercaptoacetic acid ($k_{cat}/K_M$=50,500 $M^{-1}s^{-1}$) (Morlot, C., et al. (2005) J Biol Chem 280, 15984-15991). In addition, although one might anticipate rapid hydrolysis of the resulting acylated protein species in this endopeptidase, previous work has shown that the deacylation rates of PBP3 and transpeptidase PBP1b, the most commonly labeled protein in these studies, are comparable when treated with [$^3$H]benzylpenicillin ($5.7\times10^{-5}$ $s^{-1}$ and $5.6\times10^{-5}$ $s^{-1}$, respectively) (Morlot, C., et al. (2005) J Biol Chem 280, 15984-15991). Thus, it is clear that catalytic efficiency nor hydrolysis of the resulting covalent species can explain the lack of PBP3 labeling with the β-lactone probes. Indeed, PBP3 and PBP2x are commonly inhibited to a similar extent by β-lactam antibiotics, a trend that was not observed in these studies. These data, along with the ability of the β-lactones to achieve PBP selectivity in the absence of a negatively charged substrate mimic, suggests that the lactone-based probes may be accessing different PBP binding space then the β-lactams.

Probe Concentration Determination

Probes were stored as DMSO solutions at −80° C. Concentrations were determined by measuring UV-Vis absorption of each solution at $\lambda_{max}$ of its corresponding fluorophore. For fluorescein-containing probes, 10× and 100× dilutions of probe was made in 0.1 M Tris.HCl (pH=8) and absorbance was read at 492 nm using NanoPhotometer P330 (IMPLEN). The average of 3 reads of the concentration that was in 0.1-0.9 range was used to calculate concentration. ($\varepsilon$=78,000 $M^{-1} \cdot cm^{-1}$). TAMRA- and BODIPY FL-containing probes were diluted in methanol, and concentrations were calculated in the same way as fluorescein probes. ($\lambda_{max}$ and $\varepsilon$ value equals 543 nm, 87,000 $M^{-1} \cdot cm^{-1}$ and 504 nm, 85,000 $M^{-1} \cdot cm^{-1}$, respectively)

S. pneumoniae Culturing and Probe Labeling

Strain IU1945, an unencapsulated derivative of serotype 2 S. pneumoniae strain D39, was grown statically in brain heart infusion (BHI) medium in 100×17 mm tubes by incubation in an atmosphere of 5% $CO_2$ at 37° C. to an $OD_{620}$ of ~0.2. For labeling experiments, overnight cultures that were still in exponential phase ($OD_{620}$=0.1-0.4) were diluted to $OD_{620}$=0.002-0.004 and grown as above. Samples with $OD_{620}$=0.15-0.20 were utilized in labeling experiments conducted as previously described (Kocaoglu, O, et al. (2013) Curr Protoc Chem Biol 5, 239), and summarized as follows: Cell pellets from 1.5 ml of S. pneumoniae cultures were harvested by centrifugation (16,100×g for 2 min at RT) and washed with phosphate buffered saline (PBS; pH 7.4). Cell pellets were resuspended in 50 μl of PBS containing 1-30 μg/ml of β-lactone probes and incubated at room temperature (RT) for 20 min unless noted otherwise on the figures. A reference sample was suspended in 50 μl of PBS containing 5 μg/ml Boc-FL and incubated for 10 min at RT. The cells were washed and resuspended in 100 μl of PBS containing 10 mg/ml of lysozyme and were incubated for 30 min at 37° C. The cells were lysed by a Branson Sonifier 250 (power setting 3, 30% duty cycle for 3×10 s intervals) or Hielscher vial tweeter UP200St (70% C, 95% A, 5% adjustment snap and 1 s SD Interval/10 s for 6×1 min intervals with 1 min cooling time in between), and membrane proteome was isolated by at 21,000×g for 15 min at 4° C. Membrane proteome was resuspended in 100 μl PBS, and the samples were homogenized by sonication (power setting 1, 10% duty cycle for 1 s). The protein concentration was measured by NanoDrop 1000 Spectrophotometer (Thermo Scientific) or NanoPhotometer P330 (IMPLEN). The protein concentration was adjusted to 2.5 mg/ml by diluting with PBS. Thirty microliters of proteome sample was dispensed into a clean 1.5-ml microcentrifuge tube and 10 μl of 4×SDS-PAGE loading buffer was added to each sample. The samples were heated for 5 min at 90-95° C. to denature the proteins then cooled down to RT. Ten to twelve microliters of sample was loaded onto a 10% SDS-PAGE gel (acrylamide:bis-acrylamide=29:1). The protein bands were separated by gel electrophoresis for 1.5 h at 180 V, 400 mA, 60 W. The gel was rinsed with distilled water three times before fluorescence scanning. The same growth and labeling procedures were utilized with mutant strains of *S. pneumoniae* E177 (Δpbp1a) and E193 (Δpbp1b)

B. subtilis Culturing and Probe Labeling

Figure 10:
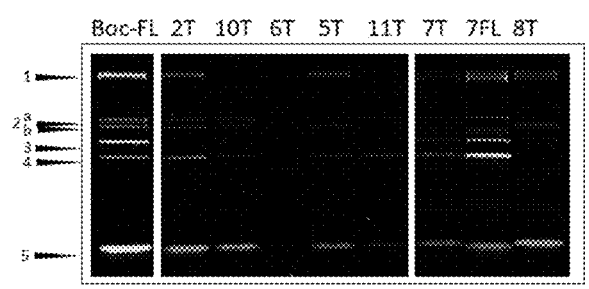
FIGS. 10a and 10b shows gel-based analysis of β-lactone probes applied to *Bacillus subtilis* PY79 cells, a rod shape Gram-positive model strain (see Example 2). Bocillin-FL was used as the control. (2S, 3R)-β-lactone (2T) labeled PBP1, PBP2a, PBP2b, PBP4 and PBP5, while 2FL labeled all the mentioned PBPs, except PBP1. Addition of a glycine residue between the lactone and fluorophore group (10T) altered the labeling profile by eliminating PBP1 and decreasing PBP4 labeling. Marked differences in selectivity were noted with alanine-functionalized compounds. The D-Ala-based probe (amino acid stereochemistry found in stem peptide; 5T) labeled PBP1, PBP2b, PBP4 and PBP5, while the L-Ala-functionalized molecule failed to tag any PBPs (6T). PBP labeling with 5FL was comparable to TAMRA probe. Changing fluorophores on (L)Ala-based probe to fluorescein and BODIPY-FL resulted in PBP labeling. 6FL probe labeled PBP1, PBP2b, PBP4 and PBP5 and 6B labeled PBP2b, PBP4 and PBP5. Addition of isopropyl group (11T) reduced the targeted proteins to PBP4 and PBP5. Probes containing side chains to mimic the functionalities found in β-lactam antibiotics, L-Phe-(2S, 3R)-β-lactone (7T and FL), D-Phe-(2S, 3R)-β-lactone (8T), were also assessed. 7T labeled PBP1, PBP3, PBP4 and PBP5, while 8T labeled PBP1, PBP2b and PBP5. PBP labeling with 7FL and 8FL is comparable to the TAMRA probes. All probes were assessed at 5 μg/ml.
Figure 10:
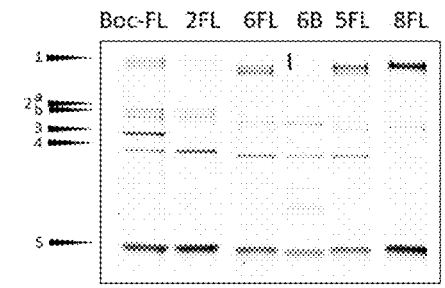

Bacillus subtilis strain PY79, was grown in Luria Bertani (LB) medium in 100×17 mm tubes by incubation at 37° C., shaking at 200 rpm. For labeling experiments, overnight cultures were diluted to $OD_{600}$=0.01-0.05 and grown as above. Samples with $OD_{600}$=0.35-0.40 were utilized in labeling experiments conducted as previously described (Kocaoglu, O, et al. (2013) *Curr Protoc Chem Biol* 5, 239), and summarized as follows: Cell pellets from 1.0 ml of *B. subtilis* cultures were harvested by centrifugation (8,000×g for 2 min at RT) and washed with phosphate buffered saline (PBS; pH 7.4). Cell pellets were resuspended in 50 μl of PBS containing 5 μg/ml of β-lactone probes and incubated at room temperature (RT) for 20 min unless noted otherwise on the figures. A reference sample was suspended in 50 μl of PBS containing 5 μg/ml Boc-FL and incubated for 10 min at RT. The cells were washed and resuspended in 100 μl of PBS containing 10 mg/ml of lysozyme and were incubated for 30 min at 37° C. The cells were lysed by a Branson Sonifier 250 (power setting 3, 30% duty cycle for 3×10 s intervals) or Hielscher vial tweeter UP200St (70% C, 95% A, 5% adjustment snap and 1 s SD Interval/10 s for 6×1 min intervals with 1 min cooling time in between), and membrane proteome was isolated by at 21,000×g for 15 min at 4° C. Membrane proteome was resuspended in 100 μl PBS, and the samples were homogenized by sonication (power setting 1, 10% duty cycle for 1 s). The protein concentration was measured by NanoDrop 1000 Spectrophotometer (Thermo Scientific) or NanoPhotometer P330 (IMPLEN). The protein concentration was adjusted to 4.0 mg/ml by diluting with PBS. Thirty microliters of proteome sample was dispensed into a clean 1.5-ml microcentrifuge tube and 10 μl of 4×SDS-PAGE loading buffer was added to each sample. The samples were heated for 5 min at 90-95° C. to denature the proteins then cooled down to RT. Ten to twelve microliters of sample was loaded onto a 10% SDS-PAGE gel (acrylamide:bis-acrylamide=29:1). The protein bands were separated by gel electrophoresis for 1.5 h at 180 V, 400 mA, 60 W. The gel was rinsed with distilled water three times before fluorescence scanning (method description for FIGS. 10a and 10b).

Sodium Dodecyl Sulfate-Polyacrylamide Gel Electrophoresis (SDS-PAGE)

The protocol for SDS-PAGE gel preparation was previously described (Kocaoglu, O, et al. (2013) *Curr Protoc Chem Biol* 5, 239). Briefly, polyacrylamide gels were composed of 10% resolving gel (10.5 ml of 1.5 M Tris-HCl buffer pH 8.8, 10.5 ml of acrylamide:bis-acrylamide 29:1 (40% solution), 21 ml of $H_2O$, 140 μl of 10% APS, 15 μl of tetramethylethylenediamine (TEMED)) and 4.5% stacking gel (2.5 ml of 0.5 M Tris-HCl buffer pH 6.8, 1.125 ml of acrylamide:bis-acrylamide 29:1 (40% solution), 6.375 ml of $H_2O$, 30 μl of 10% APS, 10 μl of TEMED). Running parameters were 180 V, 400 mA, and 60 W for 1.5 h. Experiments to examine competition of acyl homoserine lactones or p-toluenesulfonic acid salts of the β-lactones with Boc-FL were performed with acrylamide:bis-acrylamide ratio of 37.5:1.

In-Gel Fluorescence Detection

After SDS-PAGE, labeled proteins were visualized at 50-μm resolution in gels using a Typhoon 9210 gel scanner (Amersham Biosciences) with 580-nm bandpass filter for TAMRA, 526-nm short-pass filter for fluorescein and BODIPY FL, and 670-nm bandpass filter for BODIPY 650/665. All gel images were analyzed using ImageJ software (National Institutes of Health). The background signal of the gel images was subtracted, and the brightness and contrast were adjusted to optimize the signal-to-noise ratio (all operations were performed over the entire gel uniformly).

Competition Assays of Boc-FL and p-Toluenesulfonic Acid Salts of the β-Lactones for *S. pneumoniae* IU1945 PBPs Cells from 1.5 ml of culture were harvested by centrifugation (16,100×g for 2 min at RT) and washed with 1 ml of PBS, pH 7.4. Cell pellets were resuspended in 50 μl of PBS containing 5, 10, and 20 μg/ml of β-lactone p-toluenesulfonic salts and incubated for 40 min at RT. Cells were pelleted and washed in 1 ml of PBS. Next, the cells were resuspended in 50 μl of PBS containing 5 μg/ml Boc-FL and incubated for 10 min at RT. Finally, the cells were resuspended in 100 μl PBS containing 1 or 10 mg/ml lysozyme and incubated for 30 min at 37° C. Cells were lysed and sample preparation for SDS-PAGE gel-based analysis was performed as described.

Competition Assays of Boc-FL and N-Acylated L-Homoserine Lactones for *S. pneumoniae* IU1945 PBPs Cells from 1.5 ml of culture were harvested by centrifugation (16,100×g for 2 min at RT) and washed with 1 ml of PBS, pH 7.4. Cell pellets were resuspended in 50 μl of PBS containing 5-50 μg/ml of N-(β-ketocaproyl)-L-HSL, N-butyryl-L-HSL, N-3-oxo-dodecanoyl-L-HSL, and N-3-hydroxyoctanoyl-L-HSL (Cayman Chemical Company) and incubated for 30 min at RT. Cells were pelleted and washed in 1 ml of PBS. Next, the cells were resuspended in 50 μl of PBS containing 5 μg/ml Boc-FL and incubated for 10 min at RT. Finally, the cells were resuspended in 100 μl PBS containing 1 mg/ml lysozyme and incubated for 30 min at 37° C. Cells were lysed and sample preparation for SDS-PAGE gel-based analysis was performed as described.

Example 3. PBP Imaging in *S. pneumoniae* with β-Lactone Probes

PBP2x is one of the individually essential class B HMW PBPs in *S. pneumoniae* and is involved in septal PG synthesis (Tsui, H. C., et al. (2014) *Mol. Microbiol.* 94, 21-40; Land, A. D., et al. (2013) *Mol. Microbiol.* 90, 939-955; Berg, K. H., et al. (2013) *J. Bacteriol.* 195, 4342-4354; Peters, K., et al. (2014) *Mol. Microbiol.* 92, 733-755; and Philippe, J., et al. (2014) *Microb. Drug Resist.* 20, 215-221). Point and mosaic mutations in the conserved motifs of PBP2x have been associated with resistance to β-lactam antibiotics; therefore, it is an important target for antibacterial agents (Hakenbeck, R., et al. (2012) *Future Microbiol.* 7, 395-410; Nagai, K., et al. (2002) *Antimicrob Agents Ch* 46, 1273-1280; and Maurer, P., et al. (2012) *Microbial drug resistance* 18, 314-321). PBP2x localization has recently been observed using epitope tags or optimized GFP fusion constructs (Fleurie, A., et al. (2014) *PloS Genet.* 10, e1004275; Tsui, H. C., et al. (2014) *Mol. Microbiol.* 94, 21-40; Land, A. D., et al. (2013) *Mol. Microbiol.* 90, 939-955; and Peters, K., et al. (2014) *Mol. Microbiol.* 92, 733-755). These findings were highly suggestive of PBP2x localization at the septa of dividing *S. pneumoniae* cells and corroborated its role in septal PG machinery. Still, it has not been elucidated when and where this protein is active during the division process. A PBP2x-selective activity-based probe could address this challenge by displaying only the active forms of this essential PBP in live *S. pneumoniae*. Although a probe that labels only PBP2x was not identified for imaging in the wild-type strain, several compounds that label only PBP2x and PBP1b were uncovered, the latter of which can be deleted to yield a strain that is phenotypically indistinguishable from the wild-type organism (Land, A. D., et al. (2011) *J. Bacteriol.* 193, 4166-4179). Thus, the Δpbp1b mutant, referred to here as E193, provides the ideal platform in which to image PBP2x during the course of cell division.

Figure 5:
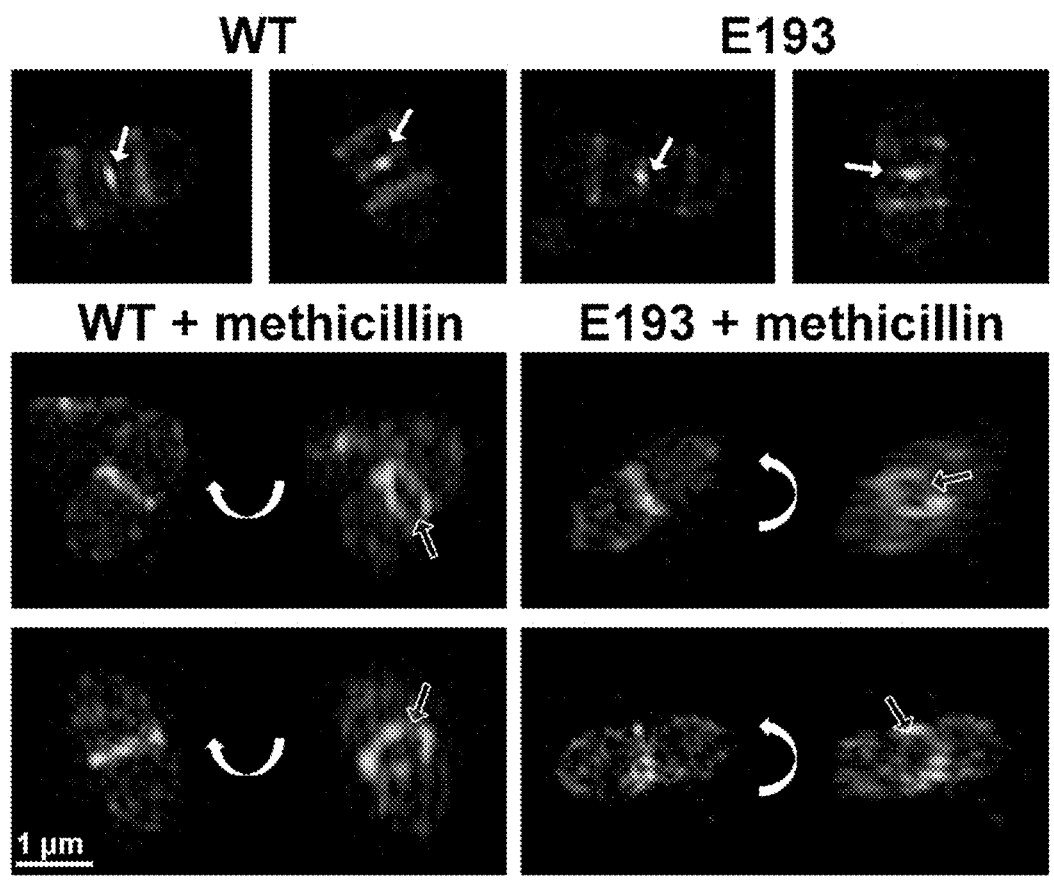
FIG. 5 shows 7FL labeling of PBP2x with or without PBP1b and a PBP2x-inhibiting concentration of methicillin. Duplicate cultures of wild-type and E193 cells were grown and pre-treated with methicillin (0.1 μg mL$^{-1}$) for 20 min, and then all cultures were labeled with 7FL. Each image in the top row of images is a separate cell, while the bottom two rows consist of pairs of images of the same cell, but one image has been rotated around the axis indicated by the arrow. 7FL labeling does not change in the absence of PBP1b, and methicillin-treated cells are elongated and lack septal labeling compared to the untreated controls. Solid arrows point to central septal labeling, and empty arrows highlight empty division site rings after methicillin pretreatment. These images are representative of >40 mid to late division cells for each condition from two biological replicates.
Figure 9:
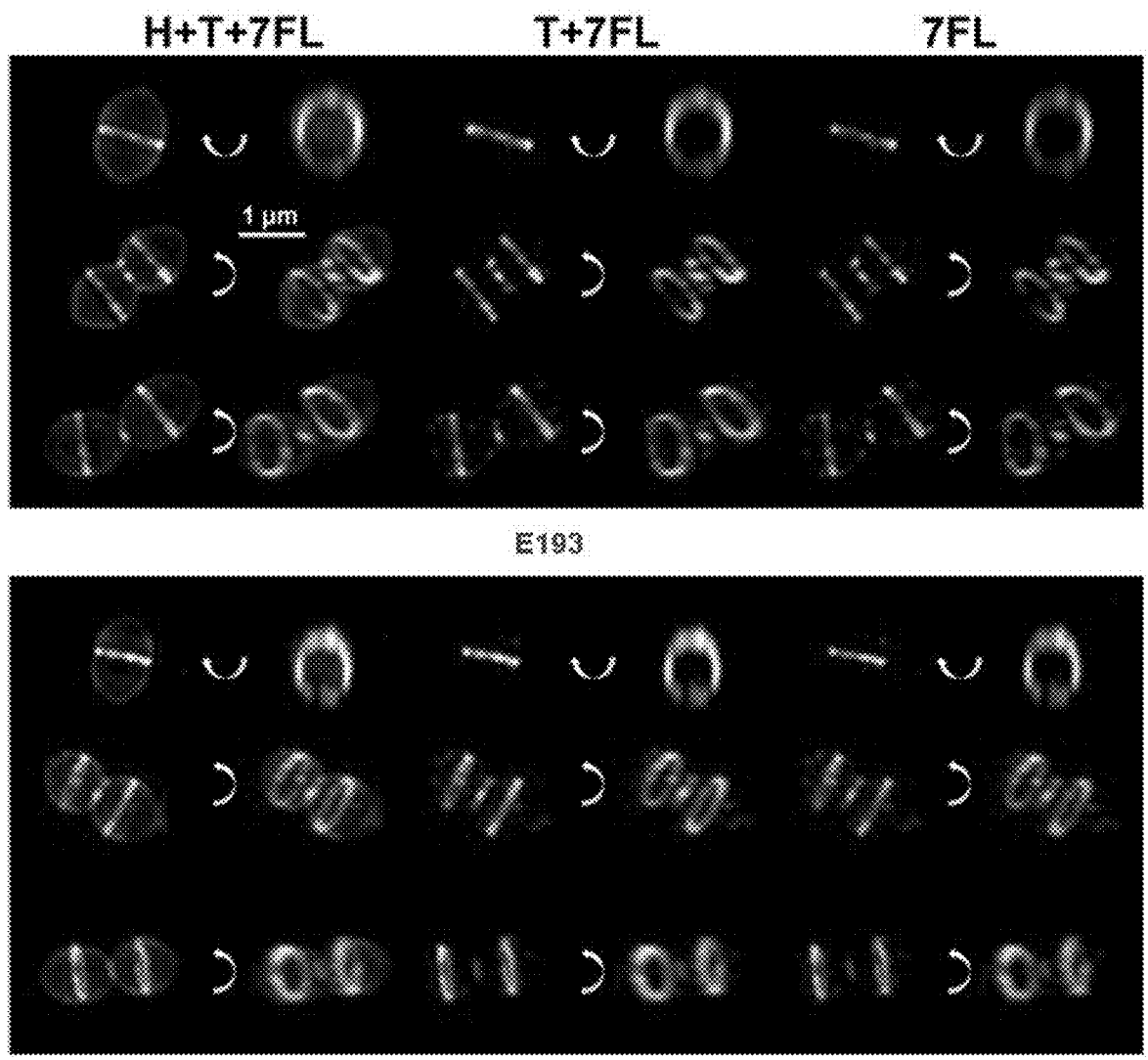
FIG. 9 shows 7FL labeling co-localizes with regions of new cell wall synthesis. Wild type (IU1945) and Δpbp1b (E193) cells were labeled for several generations with the FDAA 7-hydroxycoumarin-3-carboxylic acid 3-amino-D-alanine (HADA, H, pseudo-colored blue), then for 5 minutes with the FDAA tetramethylrhodamine 3-amino-D-alanine (TADA, T, pseudo-colored red), and finally with (2S,3R)-β-lactone-L-Phe-fluorescein (7FL, pseudo-colored green) as detailed in *Experimental Procedures*. Each row has 6 views of the same cell, with one image in each pair rotated around the indicated axis. New cell wall synthesis and 7FL labeling co-localize at all stages of division. These images are representative of >40 cells at all stages of division for each condition from 2 biological replicates.

Probe 2S,3R-β-lactone-L-Phe-fluorescein (7FL) was utilized in imaging studies to examine the activity of PBP2x during the course of cell division (FIG. 5). These images showed that PBP2x localized at the division septum as a ring during early-to-mid divisional cells. In mid-to-late divisional cells, it localized to both the constricting septal ring and to a separate site at the center of the ring itself, as well as the equators of daughter cells, before ultimately constricting down to a single point at the division site shortly before cell separation. This indicates that subpopulations of active PBP2x demonstrate different localization patterns compared to one another during a single constriction event, which correlates well with recent reports of PBP2x localization (Tsui, H. C., et al. (2014) *Mol. Microbiol.* 94, 21-40; and Land, A. D., et al. (2013) *Mol. Microbiol.* 90, 939-955), as well as newly synthesized cell wall labeled by FDAAs (FIG. 9). Immunolabeling of PBP2x and PBP1a of pneumococcus showed that PBP2x has a different position than PBP1a in the constricting septum of mid-to-late divisional cells (Tsui, H. C., et al. (2014) *Mol. Microbiol.* 94, 21-40; and Land, A. D., et al. (2013) *Mol. Microbiol.* 90, 939-955). Although both PBP2x and PBP1a localized to the septum in dividing cells at different stages, PBP2x concentrated to the septa and PBP1a remained as a larger ring at later stages of cell division. Results from 7FL-labeled PBP2x in *S. pneumoniae* strains IU1945 and E193 shows that PBP2x is active when it is localized to the center of the division site at mid-to-late division stage. Previous work using FDAAs, immunofluorescent staining and PBP2x-fusion proteins also demonstrated that PBP2x is present in the center of the septa late in division, but could not distinguish whether all of PBP2x was at this center point or if some of the protein remained in the septal ring because the FDAAs are incorporated by multiple PBPs, highlighting a critical strength of a PBP-selective, activity-based imaging strategy (Zhao, G., et al. (1999) *Antimicrob. Agents Chemother.* 43, 1124-1128; and Tsui, H.-C. T., et al. (2014) *Mol. Microbiol.* 94, 21-40).

To confirm that the observed patterns were due exclusively to labeling of PBP2x, cells were pretreated with methicillin, which specifically inhibits PBP2x in *S. pneumoniae* (Land, A. D., et al. (2013) *Mol. Microbiol.* 90, 939-955). Gel-based analysis confirmed that PBP2x labeling is dramatically decreased following methicillin treatment. 3D-SIM imaging of cells labeled with 7FL after pre-treatment with a Pbp2x-inhibiting concentration of methicillin (FIG. 5) revealed elongated cells with a labeled ring at the division site, but with minimal or no constriction evident. Importantly, >98% of methicillin-treated late division cells (≈41 cells examined) in both the wild-type and Δpbp1b strains displayed empty septal rings, in contrast with untreated controls from both strains that showed central septal labeling in 85% of wild-type and 73% of Δpbp1b cells (≈41 cells examined). This indicates a lack of active PBP2x due to methicillin inhibition, which aligns with previous results (Houk, K. N., et al. (2008) *J. Org. Chem.* 73, 2674-2678) and strongly supports the conclusion that septal 7FL labeling is due exclusively to binding of PBP2x. In E193 cells pretreated with methicillin, any labeling at the division site is likely due to remaining uninhibited PBP2x, since a small amount of PBP2x activity remains after treatment.

Application of β-Lactone Probes to *S. pneumoniae* Cells

*S. pneumoniae* IU1945, E177 (Δpbp1a) and E193 (Δpbp1b) cells were grown in Becton-Dickinson brain heart infusion (BHI) broth at 37° C. in an atmosphere of 5% $CO_2$ to $OD_{620}$ 0.2. Cells from 1 mL of culture were centrifuged at 16,100×g for 2 min at RT and washed with PBS (pH 7.4). The cells were resuspended in 50 μL of PBS containing 1-20 μg $mL^{-1}$ of different β-lactone probes or 5 μg $mL^{-1}$ of Boc-FL. After incubation for 20 min with β-lactone probes or 10 min with Boc-FL at RT, the cells were washed and resuspended in 100 μL of PBS containing 10 mg $mL^{-1}$ of lysozyme. The cells were incubated for 30 min at 37° C. and then lysed by sonification. The membrane proteome was isolated by centrifugation at 4° C. and then resuspended in 100 μL PBS, Protein concentration was determined by NanoPhotometer and adjusted at 2.5 mg $mL^{-1}$. Following the addition of 10 μL of 4×SDS-PAGE loading buffer to 30 μL of proteome, the sample was heated 5 min at 90-95° C., cooled to RT, and run on a 10% SDSPAGE, and labeled proteins were visualized in gel using a Typhoon 9500 gel scanner (GE Healthcare). All gel images were analyzed using ImageJ software (NIH).

For imaging experiments, the cells were washed to remove excess probe after incubation period and resuspended in 50 μL of PBS containing 10 μg $mL^{-1}$ of FM-4-64 or TMA-DPH (Molecular Probes). Following 2 min of incubation at RT, the cells were washed and resuspended in 50 μL of PBS. For fluorescence imaging, 5 μL of cell suspension was spotted onto a clean slide and covered with a poly-L-lysine treated coverslip.

3D-SIM of Lactone and FDAA Labeled Cells

Cells from an overnight culture were diluted to $OD_{620}$ 0.02 in 2 ml of fresh BHI prewarmed to 37° C. and incubated at 37° C. in an atmosphere of 5% $CO_2$. At $OD_{620}$ 0.2, 1.5 ml of culture was added to a microfuge tube and centrifuged at room temperature for 5 min at 16000×g. The supernatant was discarded, the pellet was resuspended in 1 ml room temperature PBS, and the culture was centrifuged a second time. The supernatant was discarded and the pellet was resuspended in either 50 μl of PBS with 5 μg $mL^{-1}$ 7FL or 100 μl PBS with 5 μg $mL^{-1}$ 8T. The cells were incubated for 20 min at room temperature in the dark. After incubation the cells were spun and washed with 1 ml of PBS (7FL) or 1 ml of PBS containing 50 mM glucose (8T). The cells were spun a second time and washed with 200 μl of PBS (7FL) or 200 μl of PBS with 50 mM glucose (8T), and finally spun a third time and resuspended in 100 μl of cold (4° C.) GTE buffer (50 mM glucose, 20 mM Tris pH 7.5, 1 mM EDTA). The cells were spun down at 4° C., the supernatant was discarded, and the pellet was resuspended in 15 μl of Vectashield Hardest Antifade (Vector Labs) and kept on ice. 1.2 μl of cells in antifade was pipetted onto a clean coverslip, applied to a slide, and imaged via 3D-SIM. 3D-SIM was performed using the OMX 3D-SIM super-resolution system located in the Indiana University Bloomington Light Microscopy Imaging Center (www.indiana.edu/~lmic/microscopes/index.html#OMX). The system used is equipped with four Photometrics Cascade II EMCCD cameras that allow simultaneous imaging of up to four colors, and is controlled by DV-OMX software, with image processing by Applied Precision softWoRx 6.0.0 software. Exposure times and % T settings for DAPI, Alexa 488, and Alexa 568 images were 5 ms and 100% for all three channels.

For pre-treatment with methicillin followed by lactone probe labeling, duplicate 2 ml cultures of each strain were created and incubated as described above. At $OD_{620}$ 0.12, methicillin was added to a final concentration of 0.1 μg mL$^{-1}$ to one culture for each strain, and the strains were placed back in the incubator. After 20 min, all cultures were harvested, labeled, and imaged as described above.

For labeling of cells with both lactone probes, the following changes were made: After a 20 min incubation with 7FL, the cells were spun down and washed once in 1 ml of PBS. The cells were spun again and resuspended in 100 μl of 8T in PBS at 5 μg mL$^{-1}$. The cells were incubated for 20 min at room temperature in the dark, and then washed and imaged as described above for 8T labeling.

For labeling of cells with FDAAs and lactone probes, the following changes were made: after diluting cells from an overnight culture to $OD_{620}$ 0.02 in 2 ml of fresh BHI, 0.5 μl of the FDAA HADA (125 μm final, stock is 500 mM in DMSO) was added to the culture and the culture was incubated at 37° C. in an atmosphere of 5% $CO_2$. At $OD_{620}$ 0.2, 500 μl of culture was added to a microfuge tube and centrifuged at room temperature for 5 min at 16000×g. The supernatant was discarded, and the pellet was resuspended in 250 μl of prewarmed BHI containing the FDAA TADA (500 μM final, stock is 500 mM in DMSO). The cells were incubated at 37° C. for 5 min, cooled on dry ice for exactly 20 seconds, and spun down in the cold (4° C.) for 2.5 min at 16000×g. The supernatant was discarded and the pellet was resuspended in 200 μl cold (4° C.) PBS. The cells were spun and washed once more with cold PBS, and then spun down a third time. The pellet was resuspended in 50 μl room temperature PBS with 5 μg mL$^{-1}$ 7FL, and the cells were labeled, washed, and imaged as described above.

Methicillin Pre-Treatment Controls.

Cells from 1.5 ml of *S. pneumoniae* IU1945 and E193 cultures at exponential phase ($OD_{620}$~0.2) were harvested by centrifugation (16,100×g for 2 min at RT) and washed with 1 ml of PBS, pH 7.4. Cell pellets were resuspended in 50 μl of PBS containing 0.1 μg/ml of methicillin and incubated for 30 min at RT. Cells were pelleted and washed in 1 ml of PBS. Next, the cells were resuspended in 50 μl of PBS containing 1 or 5 μg/ml of lac-L-Phe-FL or 5 μg/ml Boc-FL (as control) and incubated for 20 min at RT (10 min at RT for Boc-FL). Finally, the cells were resuspended in 100 μl PBS containing 1 or 10 mg/ml lysozyme and incubated for 30 min at 37° C. Cells were lysed and sample preparation for SDS-PAGE gel-based analysis was performed as described.

Figure 6:
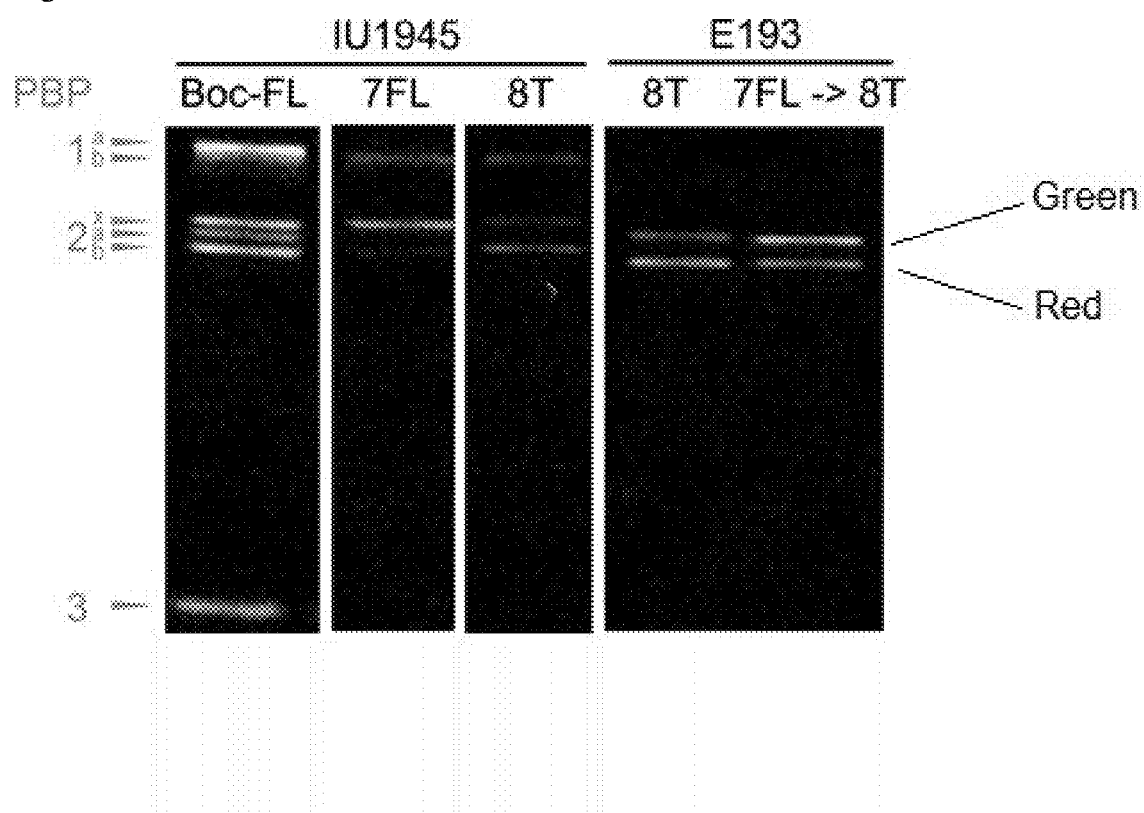
FIG. 6 shows dual labeling with (2S,3R)-β-lactone-L-Phe-fluorescein (7FL) followed by (2S, 3R)-β-lactone-D-Phe-TAMRA (8T) enables separate visualization of the activity of PBP2x (green) and PBP2b (red). Both probes were used at 5 μg/mL for 20 minutes.

Example 4. Dual Labeling Enables Visualization of Essential Proteins, PBP2x and PBP2b PBP2b, the other essential pneumococcal PBP which acts as a transpeptidase, is known to mediate peripheral PG synthesis in this microorganism (Massidda, O., et al. (2013) *Environ. Microbiol.* 15, 3133-3157; and Berg, K. H., et al. (2013) *J Bacteriol* 195, 4342-4354). Similar to PBP2x, it is a primary penicillin-resistance determinant (Grebe, T., et al. (1996) *Antimicrob Agents Ch* 40, 829-834; and Krauss, J., et al. (1996) *Microb Drug Resist* 2, 183-186). In previous work, PBP2b has been shown to follow a different localization pattern than FtsZ and remains at division septa after FtsZ reappears at the equators of daughter cells (Tsui, H. C., et al. (2014) *Mol. Microbiol.* 94, 21-40). Along the same line with PBP2x activity-based labeling, the enzymatic activity of PBP2b was assessed throughout the bacterial cell cycle and division, using lactone probes. To accomplish this goal 8T was used, which labels PBP1b, PBP2x and PBP2b (FIG. 6). When utilized alone, this probe yields a nearly identical labeling pattern as seen for 7FL (FIG. 5), due to their shared targets. 8T labels the division site as a single ring in early divisional cells, and labels the center of the division site, the constricting divisional ring, and the new equatorial rings of the future daughter cell in mid to late divisional cells. Finally, it constricts down to a single point at the division site just before the cells separate. Pre-treatment with a PBP2x-inhibiting concentration of methicillin produced elongated cells with 8T-labeled divisional rings with minimal evidence of constriction. Importantly, >98% of late divisional cells treated with methicillin (≈41 cells examined) in both the wild-type and Δpbp1b strains showed empty septal rings. Compared to the untreated strains where late divisional cells showed 8T central septal labeling in 80.5% (wild-type) and 75.6% (Δpbp1b) of cells (≈41 cells examined), this mirrors the results seen for 7FL, and reinforces the idea that PBP2x alone is localized to the center of the constricting division site.

In order to target PBP2b specifically, 8T was utilized on cells first labeled with 7FL. Results of gel based studies indicate that this combination successfully tags PBP2x and PBP2b, individually, in the Δpbp1b mutant (FIG. 6). 3D-SIM imaging of dual labeled cells revealed that 7FL displayed a septal and peripheral labeling pattern similar to the single labeling results seen in FIG. 5, as expected. However, after pre-treatment with 7FL, labeling of 8T was excluded from the center of the division site in >83% of wild-type and Δpbp1b cells (≈41 cells examined). Instead, it was restricted to the outer peripheral ring around the division site and the equatorial rings of future daughter cells, which have not yet begun to constrict. These results correlate very well with previous work (Tsui, H.-C., et al., 2016, *Mol. Microbiol.*, 100, 1039-1065) that demonstrated that PBP2b localization remained separate from and external to PBP2x during constriction, and it has been shown that active PBP2b follows this pattern as well, and ruled out the possibility that methicillin treatment disrupts PBP2b localization. Importantly, this study is the first to demonstrate co-localization of specifically labeled PBPs confirmed to be enzymatically active, and our results agree well with previous reports on PBP localization in *S. pneumoniae*. (19, 49, 50, 54, 59)

PBP2x and PBP2b localize to a single ring in early division, but during mid to late division PBP2b remains with the constricting outer ring while PBP2x moves to the center of the division site, patterns which reflect previously proposed roles for PBP2x and PBP2b in septal and peripheral cell wall synthesis. Interestingly, not all of PBP2x transitions to this central septal localization, as 7FL labeling revealed at least some PBP2x remains in the outer constricting ring. This indicates that differentially localized subpopulations of PBP2x exist, further emphasizing the need to understand how PBP dynamics are regulated. PBP2x has previously been demonstrated to interact with the serine-threonine kinase StkP, and the protein GpsB has recently been show to modulate septal closure and PBP2x migration, but the exact mechanism behind PBP2x localization remains unclear. Given that the 7FL probe is capable of specifically labeling PBP2x, it may be an effective way to monitor changes in PBP2x localization in future experiments to examine the mechanisms behind PBP dynamics.

However, there remained a possibility that pre-treatment with methicillin could indirectly disrupt the localization of PBP2b, since it causes cell elongation and abolishes constriction due to inhibition of PBP2x activity. Fortunately, by labeling the Δpbp1b strain with 7FL followed by 8T, PBP2b and PBP2x colocalize as a single ring in early division, but during mid to late division, the central septal site is labeled by 7FL (PBP2x) while 8T labeling (PBP2b) remains at the outer division ring, confirming that PBP2b and PBP2x display distinct patterns of localization during constriction. These results correlate well with previous reports on PBP localization in *S. pneumoniae* (Dargis, M., et al. (1994) *Antimicrob Agents Ch* 38, 973-980; Houk, K. N., et al. (2008) *J. Org. Chem.* 73, 2674-2678), but this study is the first to demonstrate that pattern using labeled PBPs confirmed to be enzymatically active.

Dual-Labeling Experiments

*S. pneumoniae* E193 (Δpbp1b) cells were grown in BHI broth at 37° C. in an atmosphere of 5% $CO_2$ to reach an $OD_{620}$ of 0.2-0.25. Cells from 1.5 ml of culture were harvested by centrifugation (16,100×g for 2 min at RT) and washed with 1 ml of PBS, pH 7.4. Cell pellets were resuspended in 50 μl of PBS containing 5 μg/ml lactone-L-Phe-FL (7FL) and incubated at RT for 20 min. Cells were then washed with 1 ml PBS prior to suspension in 50 μl of 5 μg/ml solution of Lac-D-Phe-TAMRA (8T) in PBS. After incubation for 20 min at RT, cells were washed and resuspended in 100 μl of PBS containing 10 mg/ml of lysozyme. Cell lysis and sample preparation for SDS PAGE was followed as described earlier.

Example 5 Preparation of the Compound 7-FL-Click

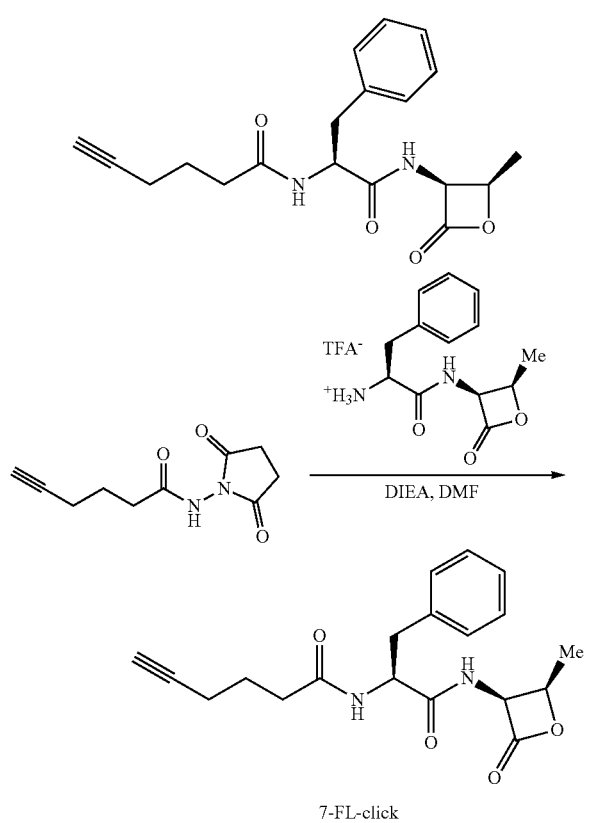

7-FL-click

To a solution of the β-lactone amine salt (0.143 mmol, 1.05 equiv) in DMF (0.7 mL) at room temperature was added NHS-5-hexynoic acid (0.136 mmol, 1 equiv) in DMF (0.7 mL) and DIEA was added dropwise (0.816 mmol, 6 equiv). The reaction was allowed to stir at room temperature under Argon (1 atm) until the reaction was complete (hours to days according to TLC). Once the reaction was completed, the solvent was evaporated, and the resulting oil was placed under high vacuum overnight. After drying, the crude material was dry loaded onto silica gel and purified by flash-column chromatography using ethanol:DCM (1:10) with 5% acetic acid. TLC conditions were the same as column conditions and potassium permanganate stain was used to visualize products (Rf~0.7). Semi-pure fractions were then purified by HPLC using an Agilent 1200 HPLC using a reverse-phase column (Agilent Eclipse XDB-C18, 5 μm, 9.4×250 mm) detected by diode array detector (200-600 nm). Gradients consisted of 30-100% B (A: $H_2O$, 0.1% FA; B: $CH_3CN$, 0.1% FA) over 23 minutes. Product had a retention time of 9.33 minutes. 7-FL-click: Yield=Yield not quantified. $^1$H NMR (400 MHz, $CDCl_3$): δ=1.35 (d, J=6.3 Hz, 3H), 1.75-1.85 (m, 2H), 1.99 (t, J=2.6 Hz, 1H), 2.11-2.27 (m, 2H), 2.34 (t, J=7.3 Hz, 2H), 3.07-3.19 (m, 2H), 4.67 (q, J=7.3 Hz, 1H), 4.85 (p, J=6.3 Hz, 1H), 5.52 (dd, J=8.4, 6.0 Hz, 1H), 5.96 (d, J=7.4 Hz, 1H), 6.83 (d, J=8.4 Hz, 1H), 7.20-7.27 (m, 2H), 7.31-7.39 (m, 3H). HRMS-ESI: calc for $C_{19}H_{23}N_2O_4^+$ $(M+H)^+$ 343.1658, found 343.1676.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

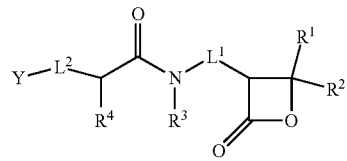

or a salt thereof, wherein:

$R^1$ is H, $(C_1-C_6)$alkyl, $(C_1-C_6)$alkoxyl, aryl, heteroaryl, or 4-8 membered heterocycle; wherein the $(C_1-C_6)$alkyl is optionally substituted with one or more groups independently selected from halo, —$OR^a$, —CN, —$NO_2$, -oxo-, —$N(R^a)_2$, —$CO_2R^a$, aryl, heteroaryl, or 4-8 membered heterocycle, wherein any aryl, heteroaryl, and 4-8 membered heterocycle is optionally substituted with one or more groups independently selected from halo, —$OR^a$, —CN, —$NO_2$, -oxo-, —$N(R^a)_2$, or —$CO_2R^a$;

$R^2$ is H or $(C_1-C_6)$alkyl;

$R^3$ is H or $(C_1-C_6)$alkyl;

$R^4$ is

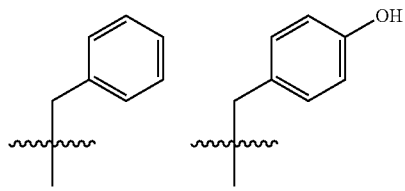

-continued

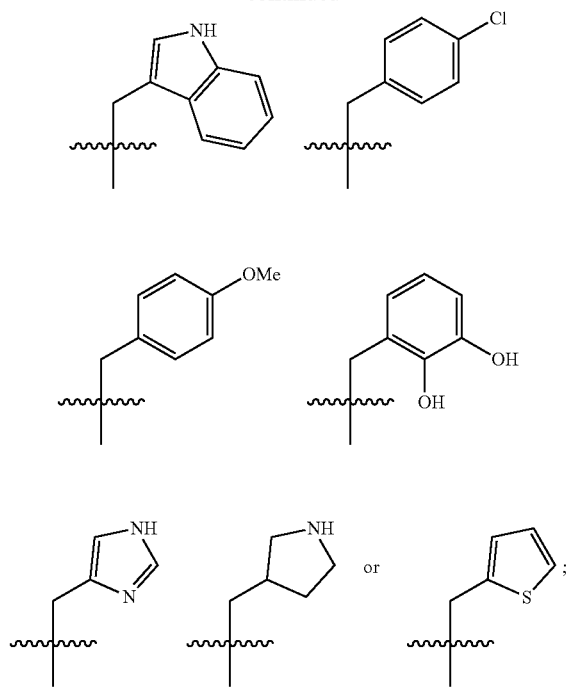

L¹ is absent or (C₁-C₄)alkylene;

L² is absent or a linking group;

Y is (C₂-C₆)alkynyl, or Y comprises a core structure selected from the group consisting of rhodol, rhodamine, carboxytetramethylrhodamine, and rosamine; and each $R^a$ is independently hydrogen or $C_{1-4}$ alkyl; or two $R^a$ groups taken together with the nitrogen to which they are attached form pyrrolidinyl, piperidinyl, piperazinyl or morpholinyl.

2. The compound or salt of claim 1, wherein L² is —C(=O)NH(CH₂)₃CH₂— or —C(=O)NH(CH₂)₅C(=O)NH—.

3. The compound or salt of claim 1, wherein Y is (C₂-C₆)alkynyl.

4. The compound or salt of claim 1, wherein Y comprises a core structure selected from the group consisting of rhodol, rhodamine, carboxytetramethylrhodamine, and rosamine, and an analog thereof.

5. The compound or salt of claim 1, wherein Y is

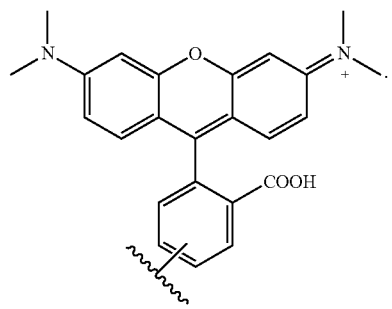

6. A compound selected from the group consisting of:

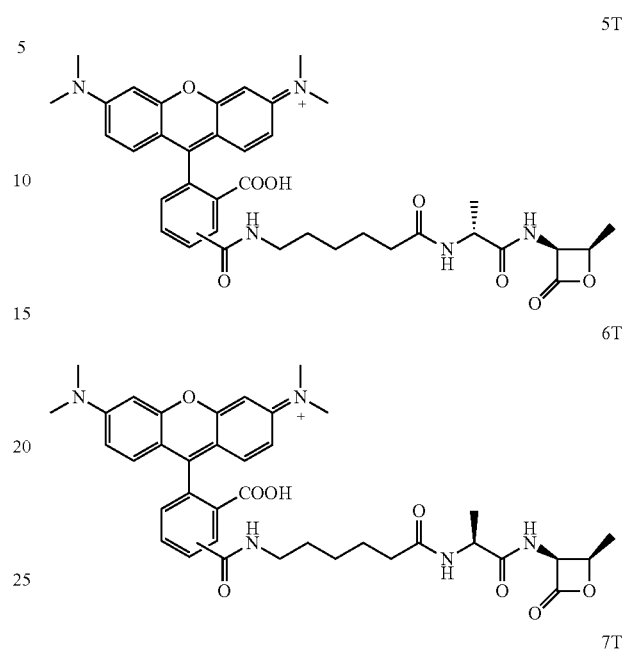

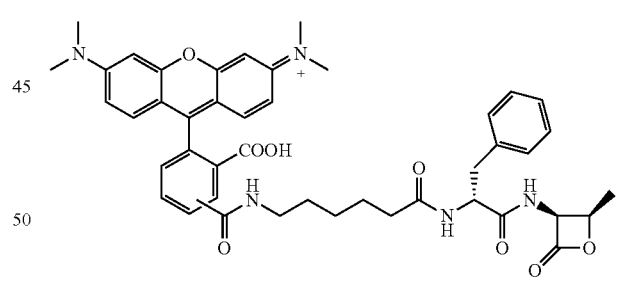

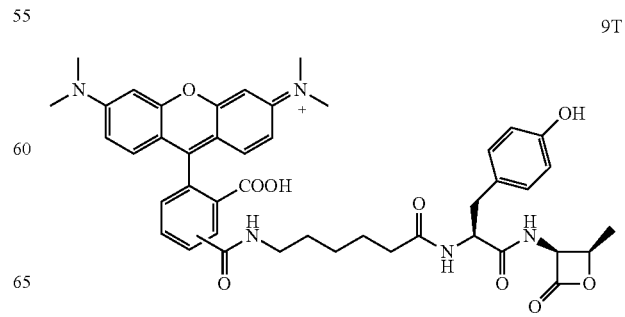

-continued

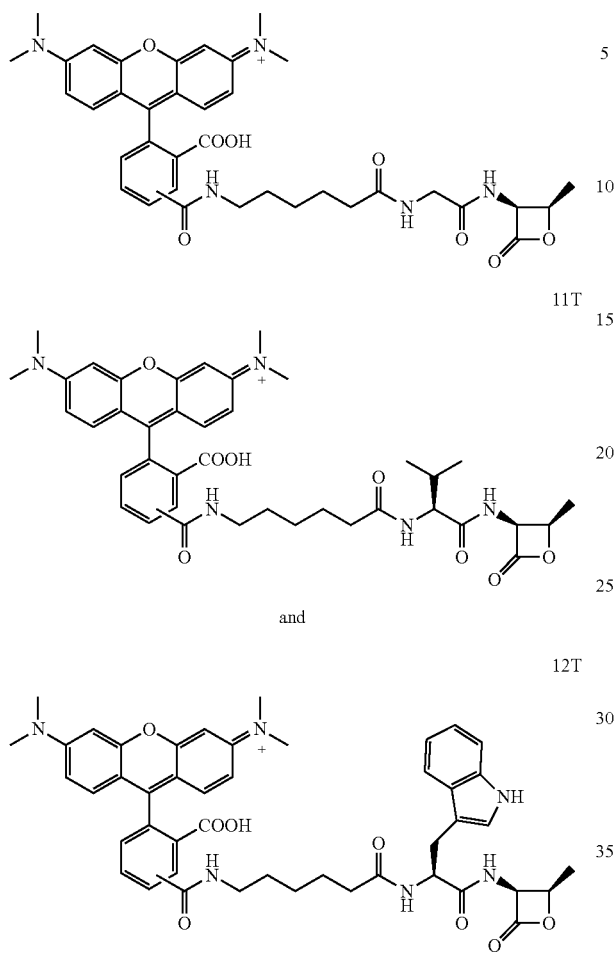

or a salt thereof.

7. A composition comprising a compound of formula I as described in claim 1, or a salt thereof, and an excipient.

8. A kit comprising:
1) a compound of formula I as described in claim 1, or a salt thereof;
2) instructions for contacting one or more penicillin-binding protein (PBPs) with the compound to provide one or more labeled PBPs; and
3) instructions for detecting the labeled PBPs.

9. The compound of claim 1, wherein the group

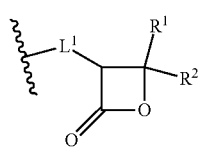

is selected from the group consisting of:

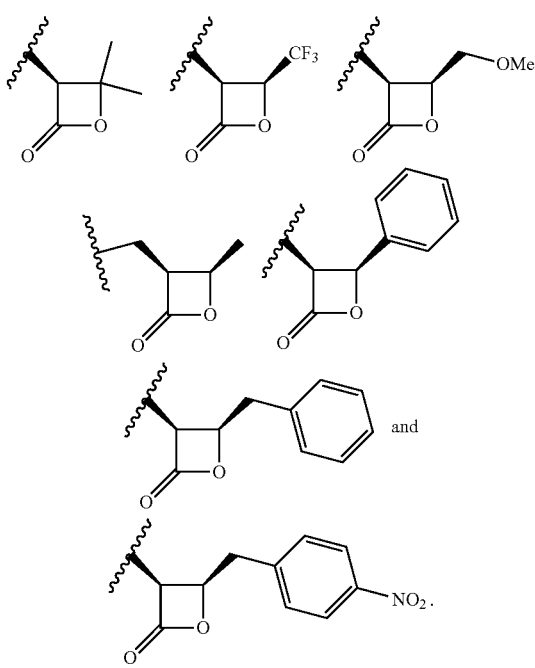

10. The compound of claim 1, wherein the group

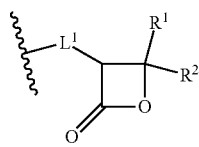

is selected from the group consisting of:

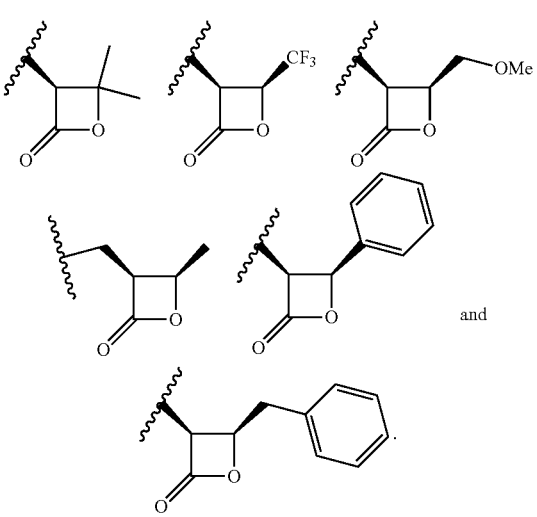

* * * * *